(12) United States Patent
Schteingart et al.

(10) Patent No.: US 9,334,305 B2
(45) Date of Patent: *May 10, 2016

(54) SYNTHETIC PEPTIDE AMIDES AND DIMERS THEREOF

(71) Applicant: Cara Therapeutics, Inc., Shelton, CT (US)

(72) Inventors: Claudio D. Schteingart, San Diego, CA (US); Frédérique Menzaghi, Rye, NY (US); Guangcheng Jiang, San Diego, CA (US); Roberta Vezza Alexander, San Diego, CA (US); Javier Sueiras-Diaz, La Jolla, CA (US); Robert H. Spencer, New Hope, PA (US); Derek T. Chalmers, Riverside, CT (US); Zhiyong Luo, New City, NY (US)

(73) Assignee: Cara Therapeutics, Inc., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/959,931

(22) Filed: Aug. 6, 2013

(65) Prior Publication Data

US 2014/0357579 A1 Dec. 4, 2014

Related U.S. Application Data

(63) Continuation of application No. 12/913,363, filed on Oct. 27, 2010, now Pat. No. 8,536,131, which is a continuation of application No. 11/938,776, filed on Nov. 12, 2007, now Pat. No. 7,842,662.

(60) Provisional application No. 60/858,120, filed on Nov. 10, 2006, provisional application No. 60/858,121, filed on Nov. 10, 2006, provisional application No. 60/858,123, filed on Nov. 10, 2006, provisional application No. 60/928,527, filed on May 10, 2007, provisional application No. 60/928,551, filed on May 10, 2007, provisional application No. 60/928,557, filed on May 10, 2007.

(51) Int. Cl.
*C07K 5/107* (2006.01)
*C07K 5/117* (2006.01)
*C07K 5/103* (2006.01)
*A61K 38/00* (2006.01)

(52) U.S. Cl.
CPC .............. *C07K 5/1024* (2013.01); *C07K 5/1005* (2013.01); *C07K 5/1008* (2013.01); *C07K 5/1016* (2013.01); *A61K 38/00* (2013.01)

(58) Field of Classification Search
CPC .................. A61K 38/07; C07K 5/00–5/126
See application file for complete search history.

(56) References Cited

U.S. PATENT DOCUMENTS

| 5,965,701 | A | * | 10/1999 | Junien | C07K 5/1027 |
| | | | | | 530/330 |
| 6,191,103 | B1 | | 2/2001 | Shohet et al. | |
| 6,780,846 | B1 | | 8/2004 | O'Mahony et al. | |
| 6,984,719 | B1 | | 1/2006 | Chemtob et al. | |
| 7,244,573 | B2 | | 7/2007 | Carman et al. | |
| 7,348,162 | B2 | | 3/2008 | Saris et al. | |
| 7,402,564 | B1 | | 7/2008 | Schteingart et al. | |
| 7,842,662 | B2 | | 11/2010 | Schteingart et al. | |
| 2005/0113294 | A1 | | 5/2005 | Dolle | |
| 2006/0229252 | A1 | | 10/2006 | Falla et al. | |

FOREIGN PATENT DOCUMENTS

| DE | 43 10643 A1 | 4/1993 |
| EP | 0 249 169 B1 | 6/1987 |
| EP | 0 334 244 A2 | 3/1989 |
| EP | 0 342 962 B1 | 5/1989 |
| EP | 0 361 977 A2 | 9/1989 |
| EP | 0 505 680 B1 | 1/1992 |
| EP | 0 517 589 B1 | 12/1996 |
| EP | 0 503 301 B1 | 11/1997 |
| WO | 8808429 A1 | 11/1988 |
| WO | 9421242 A1 | 9/1994 |
| WO | 9500546 A1 | 1/1995 |
| WO | 9522557 A1 | 8/1995 |
| WO | 9602267 A1 | 2/1996 |

(Continued)

OTHER PUBLICATIONS

Aggarwal et al. "Synthesis and Screening of a Random Dimeric Library Using the One-Bead-One-Dimer Combinatorial Approach," Bioconjugate Chemistry, 2006, 17, 335-340.*
Mollica et al. "Synthesis and biological evaluation of new biphalin analogues with non-hydrazine linkers," Bioorganic & Medicinal Chemistry Letters 2005, 15, 2471-2475.*
Portoghese "From Models to Molecules: Opioid Receptor Dimers, Bivalent Ligands, and Selective Opioid Receptor Probes," J. Medicinal Chemistry, 2001, 44, 2259-2269.*
Bentley, G.A. et al., Evidence for an action of morphine and the enkephalins on sensory nerve endings in the mouse peritoneum, Br. J. Pharmac., 73:325-332 (1981).

(Continued)

*Primary Examiner* — Christina Bradley
(74) *Attorney, Agent, or Firm* — Algis Anilionis; F. Chau & Associates, LLC

(57) ABSTRACT

The invention relates to synthetic peptide amide ligands of the kappa opioid receptor and particularly to agonists of the kappa opioid receptor that exhibit low $P_{450}$ CYP inhibition and low penetration into the brain. The synthetic peptide amides of the invention conform to the structure:

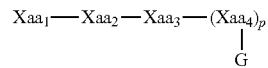

The compounds are useful in the prophylaxis and treatment of pain and inflammation associated with a variety of diseases and conditions.

38 Claims, 10 Drawing Sheets

(56) References Cited

FOREIGN PATENT DOCUMENTS

| WO | 9707130 | A1 | 2/1997 |
|---|---|---|---|
| WO | 9709995 | A1 | 3/1997 |
| WO | 9808492 | A1 | 3/1998 |
| WO | 9808868 | A1 | 3/1998 |
| WO | 9921877 | A1 | 5/1999 |
| WO | 9932510 | A1 | 7/1999 |
| WO | 03011896 | A1 | 2/2003 |
| WO | 2006058539 | A2 | 6/2006 |
| WO | 2006058539 | A3 | 6/2006 |

OTHER PUBLICATIONS

Diop, Laurent et al., Peripheral k-opioid receptors mediate the antinociceptive effect of fetodozine on the duodenal pain reflex in rat, European Journal of Pharmacology 271, pp. 65-71 (1994).

Iyer, S. et al., Characterization and Biological Significance of Immunosuppressive Peptide D2702.75-84 (E→V) Binding Protein, J. Biol. Chem., vol. 273, No. 5, pp. 2692-2697 (1998).

Junien and Riviere, Review article: the hypersensitive gut—peripheral kappa agonists as a new pharmacological approach, Alimentary Pharmacology and Therapeutics, 9:117-126 (1995).

Lamb, J.R. et al., Influence of antigen structure on the activation and induction of unresponsiveness in cloned human T lymphocytes, Immunology, 57, pp. 331-335 (1986).

Ostergaard, S. et al., Novel avidin and streptavidin binding sequences found in synthetic peptide libraries, FEBS Letters, 362, pp. 306-308 (1995).

Riviere, Pierre J.M. et al., Fedotozine Reverses Ileus Induced by Surgery or Peritonitis: Action at Peripheral K-Opioid Receptors, Gastroenterology 104:724-731 (1993).

Samson, Isabelle et al., Screening a Random Pentapeptide Library, Composed of 14 D-Amino Acids, against the COOH-terminal Sequence of Fructose-1,6-bisphosphate Aldolase from Trypanosoma brucei, The Journal of Biological Chemistry, vol. 272, No. 17, Issue Apr. 25, pp. 11378-11383 (1997).

Schröder, E., Synthese des all-D-Val5-Angiotensin II-Asp1-β-amids, J. Liebigs Ann Chem, pp. 241—(1966).

Seo, Jeong Kon et al., A Peptide with Unique Receptor Specificity, Jimmunol, pp. 1895-1901 (1997).

Vanderah, T.W. et al., Mediation of Swim-Stress Antinociception by the Opioid Delta2 Receptor in the Mousel, J. Pharm. Exper. Therapeutics, vol. 262:1 (1992).

Vogler, Von K. et al., Synthese von All-D-Val5-Angiotensin II-Aspl-β-Amid1), Helv Chim Acta, 48:6:152, pp. 1407-1414 (1965).

Vonvoigtlander, P.F. et al., U-50,488: A Selective and Structurally Novel Non-Mu (Kappa) Opioid Agonist, J. Pharm. Exper. Therapeutics, 224:7-12 (1983).

Wang, X. et al., Applications of topologically segregated bilayer beads in 'one-bead one-compound' combinatorial libraries, J. Peptide Res. 65, pp. 130-138 (2005).

Wisniewski, K. et al., Long Acting, Selective, Peripheral Kappa Agonists, J. Peptide Sci., 6 supp:S189 (2000) (Abstract).

Wisniewski, K. et al., Long Acting, Selective, Peripheral Kappa Agonists, Posters:1 Bioactive, P358 (Poster).

Wisniewski, K. et al., Long Acting, Selective, Peripheral Kappa Agonists, Peptides 2000:Proc. of 36th Eur Peptide Symp. (J. Martinez & J.A. Fehrentz, eds.) Editions EDK, pp. 775-776 (2001) (Mini-publication).

Vippagunta, "Crystalline solids," Adv. Drug Delivery Rev., 2001, 48 3-26.

Byrn et al. Solid State Chemistry of Drugs, 2 Ed. 1999 "Hydrates and Solvates" pp. 233-247.

Testa, "Prodrug research: futile or fertile?" Biochemical Pharmacology, 2004, 68, 2097-2106.

\* cited by examiner

SYNTHETIC PEPTIDE AMIDES AND DIMERS THEREOF

RELATED APPLICATIONS

This application claims priority to U.S. provisional application Ser. Nos. 60/858,120; 60/858,121; and 60/858,123 filed Nov. 10, 2006, and to U.S. provisional applications Ser. Nos. 60/928,527; 60/928,551, and 60/928,557 filed May 10, 2007, each of which are expressly incorporated herein by reference in their entireties.

FIELD OF THE INVENTION

The invention relates to synthetic peptide amides incorporating D-amino acids in the peptide chain and more particularly to such synthetic peptide amides that are kappa opioid receptor agonists, and methods for their use as prophylactic and therapeutic agents.

BACKGROUND

Kappa opioid receptors have been suggested as targets for intervention for treatment or prevention of a wide array of diseases and conditions by administration of kappa opioid receptor agonists. See for example, Jolivalt et al., *Diabetologia,* 49(11):2775-85; Epub Aug. 19, 2006), describing efficacy of asimadoline, a kappa receptor agonist in rodent diabetic neuropathy; and Bileviciute-Ljungar et al., *Eur. J. Pharm.* 494:139-46 (2004) describing the efficacy of kappa agonist U-50,488 in the rat chronic constriction injury (CCI) model of neuropathic pain and the blocking of its effects by the opioid antagonist, naloxone. These observations support the use of kappa opioid receptor agonists for treatment of diabetic, viral and chemotherapy-induced neuropathic pain. The use of kappa receptor agonists for treatment or prevention of visceral pain including gynecological conditions such as dysmenorrheal cramps and endometriosis has also been reviewed. See for instance, Riviere, *Br. J. Pharmacol.* 141: 1331-4 (2004).

Kappa opioid receptor agonists have also been proposed for the treatment of pain, including hyperalgesia. Hyperalgesia is believed to be caused by changes in the milieu of the peripheral sensory terminal occur secondary to local tissue damage. Tissue damage (e.g., abrasions, burns) and inflammation can produce significant increases in the excitability of polymodal nociceptors (C fibers) and high threshold mechanoreceptors (Handwerker et al. (1991) *Proceeding of the VI$^{th}$ World Congress on Pain,* Bond et al., eds., Elsevier Science Publishers BV, pp. 59-70; Schaible et al. (1993) *Pain* 55:5-54). This increased excitability and exaggerated responses of sensory afferents is believed to underlie hyperalgesia, where the pain response is the result of an exaggerated response to a stimulus. The importance of the hyperalgesic state in the post-injury pain state has been repeatedly demonstrated and appears to account for a major proportion of the post-injury/inflammatory pain state. See for example, Woold et al. (1993) *Anesthesia and Analgesia* 77:362-79; Dubner et al. (1994) In, *Textbook of Pain,* Melzack et al., eds., Churchill-Livingstone, London, pp. 225-242.

Kappa opioid receptors have been suggested as targets for the prevention and treatment of cardiovascular disease. See for example, Wu et al. "Cardioprotection of Preconditioning by Metabolic Inhibition in the Rat Ventricular Myocyte—Involvement of kappa Opioid Receptor" (1999) *Circulation Res* vol. 84: pp. 1388-1395. See also Yu et al. "Anti-Arrythmic Effect of kappa Opioid Receptor Stimulation in the Perfused Rat Heart: Involvement of a cAMP-Dependent Pathway" (1999) *J Mol Cell Cardiol.* vol. 31(10): pp. 1809-1819.

It has also been found that development or progression of these diseases and conditions involving neurodegeneration or neuronal cell death can be prevented, or at least slowed, by treatment with kappa opioid receptor agonists. This improved outcome is believed to be due to neuroprotection by the kappa opioid receptor agonists. See for instance, Kaushik et al. "Neuroprotection in Glaucoma" (2003) *J. Postgraduate Medicine* vol. 49 (1): pp. 90-95.

The presence of kappa opioid receptors on immune cells (Bidlak et al., (2000) *Clin. Diag. Lab. Immunol.* 7(5):719-723) has been implicated in the inhibitory action of a kappa opioid receptor agonist, which has been shown to suppress HIV-1 expression. See Peterson P K et al., *Biochem Pharmacol.* 2001, 61(19):1145-51.

Walker, *Adv. Exp. Med. Biol.* 521:148-60 (2003) appraised the anti-inflammatory properties of kappa agonists for treatment of osteoarthritis, rheumatoid arthritis, inflammatory bowel disease and eczema. Bileviciute-Ljungar et al., *Rheumatology* 45:295-302 (2006) describe the reduction of pain and degeneration in Freund's adjuvant-induced arthritis by the kappa agonist U-50,488.

Wikstrom et al., *J. Am. Soc. Nephrol.* 16:3742-7 (2005) describes the use of the kappa agonist, TRK-820 for treatment of uremic and opiate-induced pruritus, and Ko et al., *J. Pharmacol. Exp. Ther.* 305:173-9 (2003) describe the efficacy of U-50,488 in morphine-induced pruritus in the monkey.

Application of peripheral opioids including kappa agonists for treatment of gastrointestinal diseases has also been extensively reviewed. See for example, Lembo, *Diges. Dis.* 24:91-8 (2006) for a discussion of use of opioids in treatment of digestive disorders, including irritable bowel syndrome (IBS), ileus, and functional dyspepsia.

Ophthalmic disorders, including ocular inflammation and glaucoma have also been shown to be addressable by kappa opioids. See Potter et al., *J. Pharmacol. Exp. Ther.* 309:548-53 (2004), describing the role of the potent kappa opioid receptor agonist, bremazocine in reduction of intraocular pressure and blocking of this effect by norbinaltorphimine (norBNI), the prototypical kappa opioid receptor antagonist; and Dortch-Carnes et al., *CNS Drug Rev.* 11(2):195-212 (2005). U.S. Pat. No. 6,191,126 to Gamache discloses the use of kappa opioid agonists to treat ocular pain. Otic pain has also been shown to be treatable by administration of kappa opioid agonists. See U.S. Pat. No. 6,174,878 also to Gamache.

Kappa opioid agonists increase the renal excretion of water and decrease urinary sodium excretion (i.e., produce a selective water diuresis, also referred to as aquaresis). Many, but not all, investigators attribute this effect to a suppression of vasopressin secretion from the pituitary. Studies comparing centrally acting and purportedly peripherally selective kappa opioids have led to the conclusion that kappa opioid receptors within the blood-brain barrier are responsible for mediating this effect. Other investigators have proposed to treat hyponatremia with nociceptin peptides or charged peptide conjugates that act peripherally at the nociceptin receptor, which is related to but distinct from the kappa opioid receptor. See: D. R. Kapusta, Life Sci., 60:15-21, 1997; U.S. Pat. No. 5,840,696 and U.S. Patent Appl. No. 20060052284.

SUMMARY OF THE INVENTION

The present invention provides synthetic peptide amides of formula I:

$$\text{Xaa}_1 - \text{Xaa}_2 - \text{Xaa}_3 - (\text{Xaa}_4)_p$$
$$|$$
$$G$$

Formula I and stereoisomers, mixtures of stereoisomers, prodrugs, pharmaceutically acceptable salts, hydrates, solvates, acid salt hydrates N-oxides and isomorphic crystalline forms thereof.

In formula I, each $Xaa_1$ is independently chosen from the following D-amino acids: (A)(A')D-phenylalanine, (A)(A') α-methyl-D-phenylalanine, D-tyrosine, D-1,2,3,4-tetra-hydroisoquinoline-3carboxylic acid, D-tert-leucine, D-neopentylglycine, D-phenylglycine, D-homo-phenylalanine, and β-(E)D-alanine, wherein each (A) and each (A') are phenyl ring substituents independently chosen from —H, —F, —Cl, —NO$_2$, —CH$_3$, —CF$_3$, —CN, —CONH$_2$, and wherein each (E) is independently chosen from cyclobutyl, cyclopentyl, cyclohexyl, pyridyl, thienyl and thiazolyl. Each $Xaa_2$ is independently chosen from (A)(A')D phenylalanine, 3,4-dichloro-D-phenylalanine, (A)(A')(α-Me)D-phenylalanine, D-1-naphthylalanine, D-2-naphthylalanine, D-tyrosine, (E)D-alanine, and D-tryptophan. Each $Xaa_3$ is independently chosen from D-norleucine, D-phenylalanine, (E)-D-alanine, D-leucine, α-MeD-leucine, D-homoleucine, D-valine, and D-methionine. Each $Xaa_4$ is independently chosen from (B)$_2$D-arginine, (B)$_2$D-norarginine, (B)$_2$D-homoarginine, ζ-(B)D-homolysine, D-2,3-diaminopropionic acid, ε-(B)D-lysine, ε-(B)$_2$-D-lysine, D-aminomethylphenylalanine, amidino-D-aminomethyl-phenylalanine, γ-(B)$_2$D-α,γ-diaminobutyric acid, δ-(B)$_2$α-(B')D-ornithine, D-2-amino-3(4-piperidyl)-propionic acid, D-2-amino-3(2-aminopyrrolidyl) propionic acid, D-α-amino-β-amidino-propionic acid, α-amino-4-piperidineacetic acid, cis-α,4-diaminocyclo-hexane acetic acid, trans-α,4-diaminocyclohexaneacetic acid, cis-α-amino-4-methyl-aminocyclo-hexane acetic acid, trans-α-amino-4-methylaminocyclohexane acetic acid, α-amino-1-amidino-4-piperidineacetic acid, cis-α-amino-4-guanidino-cyclohexane acetic acid, and trans-α-amino-4-guanidinocyclohexane acetic acid, wherein each (B) is independently chosen from —H and C$_1$-C$_4$ alkyl, and (B') is —H or (α-Me); and p is zero or 1.

The moiety G is selected from one of the following moieties (i)-(iv):

(i) G is

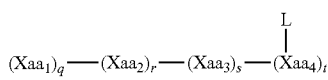

wherein p, q, r, s and t are each independently zero or 1, provided that at least one of s and t are 1. The moiety L is a linker chosen from ε-D-Lys, ε-Lys, δ-D-Orn, δ-Orn, γ-aminobutyric acid, 8-aminooctanoic acid, 11-amino-undecanoic acid, 8-amino-3,6-dioxaoctanoic acid, 4-amino-4-carboxylic piperidine and (D-Lys-Gly lactam)$_2$, (ii) G is

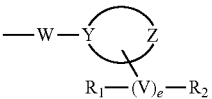

wherein p is 1, and $Xaa_3$-$Xaa_4$- is chosen from D-norleucine-(B)$_2$D-arginine-, D-leucine-δ-(B)$_2$α-(B')D-ornithine-, and a-methyl-D-leucine-δ(B)$_2$-α(B')D-ornithine-; and the moiety

is an optionally substituted 4 to 8-membered heterocyclic ring moiety wherein all ring heteroatoms in said ring moiety are nitrogen atoms; wherein Y and Z are each independently carbon or nitrogen atoms; provided that when such ring moiety is a six, seven or eight-membered ring, Y and Z are separated by at least two ring atoms, and provided that when such ring moiety has a single heteroatom which is nitrogen, then such ring moiety is non-aromatic.

(iii) G is

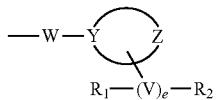

wherein p is 1; and the moiety

is an optionally substituted 4 to 8-membered heterocyclic ring moiety wherein Y is a carbon or a nitrogen atom and Z is carbon, nitrogen, oxygen, sulfur, sulfoxide, or sulfonyl; provided that when such ring moiety is a six, seven or eight-membered ring, Y and Z are separated by at least two ring atoms, provided that when such ring moiety is non-aromatic and Z is a carbon or a nitrogen atom, then such ring moiety includes at least one sulfur or oxygen ring heteroatom; and provided further that when such ring moiety is aromatic, then Y is a carbon atom.

(iv) G is

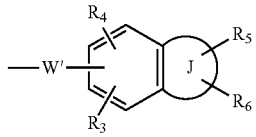

wherein J is a 5-, 6-, or 7-membered heterocyclic ring moiety comprising 1, 2, or 3 heteroatoms in the ring wherein $R_3$ and $R_4$ are each independently selected from $C_1$-$C_3$ alkyl, halo, —OH, —CF$_3$, —NH$_2$, —COOH and amidino; and $R_5$ and $R_6$ are each independently selected from $C_1$-$C_3$ alkyl, oxo, halo, —OH, —CF$_3$, —NH$_2$, —COOH and amidino.

The moiety W' is chosen from one of the following three options: null; —NH—(CH$_2$)$_b$— with b equal to zero, 1, 2, 3, 4, 5, or 6; and —NH—(CH$_2$)$_c$—O— with c equal to 2 or 3.

The moiety V represents C$_1$-C$_6$ alkyl, and the operator, e is either zero or 1, wherein when e is zero, then V is null and, R$_1$ and R$_2$ are directly bonded to the same or different ring atoms. The groups R$_1$ and R$_2$ can be any one of (a), (b), (c) or (d) as follows:

(a) R$_1$ is H, OH, halo, CF$_3$, —NH$_2$, —COOH, C$_1$-C$_6$ alkyl, amidino, C$_1$-C$_6$ alkyl-substituted amidino, aryl, optionally substituted heterocyclyl, Pro-amide, Pro, Gly, Ala, Val, Leu, Ile, Lys, Arg, Orn, Ser, Thr, CN, CONH$_2$, COR', SO$_2$R', CONR'R", NHCOR', OR', or SO$_2$NR'R"; wherein said optionally substituted heterocyclyl is optionally singly or doubly substituted with substituents independently selected from the group consisting of C$_1$-C$_6$ alkyl, —C$_1$-C$_6$ alkoxy, oxo, —OH, —Cl, —F, —NH$_2$, —NO$_2$, —CN, —COOH, and amidino; wherein R' and R" are each independently H, C$_1$-C$_8$ alkyl, aryl, heterocyclyl or R' and R" are combined to form a 4- to 8-membered ring, which ring is optionally substituted singly or doubly with substituents independently selected from the group consisting of C$_1$-C$_6$ alkyl, —C$_1$-C$_6$ alkoxy, —OH, —Cl, —F, —NH$_2$, —NO$_2$, —CN, and —COOH, amidino; and R$_2$ is H, amidino, singly or doubly C$_1$-C$_6$ alkyl-substituted amidino, —CN, —CONH$_2$, —CONR'R", —NHCOR', —SO$_2$NR'R", or —COOH; or (b) R$_1$ and R$_2$ taken together can form an optionally substituted 4- to 9-membered heterocyclic monocyclic or bicyclic ring moiety which is bonded to a single ring atom of the Y and Z-containing ring moiety; or (c) R$_1$ and R$_2$ taken together with a single ring atom of the Y and Z-containing ring moiety can form an optionally substituted 4- to 8-membered heterocyclic ring moiety to form a spiro structure; or (d) R$_1$ and R$_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety.

Each of the aforementioned optionally substituted 4- to 9-membered heterocyclic ring moieties that include R$_1$ and R$_2$ is optionally singly or doubly substituted with substituents independently chosen from C$_1$-C$_6$ alkyl, —C$_1$-C$_6$ alkoxy, optionally substituted phenyl (as defined above), oxo, —OH, —Cl, —F, —NH$_2$, —NO$_2$, —CN, —COOH, and amidino.

The above formula I definitions are subject to the following three provisos:

(1) That when the Y and Z-containing ring moiety is a six or seven membered ring comprising a single ring heteroatom and when one of Y and Z is C and the other of Y and Z is N, and e is zero, then R$_1$ is not OH, and R$_1$ and R$_2$ are not both H;

(2) That when the Y and Z-containing ring moiety is a six membered ring comprising two ring heteroatoms, both Y and Z are nitrogen atoms, W is null, and the moiety —V$_e$(R$_1$)(R$_2$) is attached to Z, then —V$_e$(R$_1$)(R$_2$) is chosen from amidino, C$_1$-C$_6$ alkyl-substituted amidino, dihydroimidazole, —CH$_2$COOH, and —CH$_2$C(O)NH$_2$; and (3) That if the Y and Z-containing ring moiety is a six membered ring comprising a sulfur or an oxygen ring heteroatom, or if the Y and Z-containing ring moiety is a non-aromatic six membered ring that includes two ring heteroatoms, wherein both Y and Z are nitrogen atoms and W is null, or if the Y and Z-containing ring moiety is a six-membered aromatic ring that includes a single ring heteroatom, which heteroatom is a nitrogen atom, then, when e is zero, R$_1$ and R$_2$ are not both hydrogen.

The invention also provides a selective kappa opioid receptor agonist (interchangeably referred to herein as a kappa receptor agonist or simply as a kappa agonist) which is a synthetic peptide amide of the invention, as described above.

The invention also provides a pharmaceutical composition, which includes a synthetic peptide amide of the invention and a pharmaceutically acceptable diluent, excipient or carrier.

Also provided is a method of treating or preventing a kappa opioid receptor-associated disease or condition in a mammal. The method includes administering to the mammal a composition that includes an effective amount of a synthetic peptide amide of the invention. The invention also provides uses of the synthetic peptide amides of the invention for the preparation of medicaments and pharmaceutical compositions useful for the treatment of a kappa opioid receptor-associated disease or condition in a mammal.

The invention further provides a method of treating or preventing a kappa opioid receptor-associated disease or condition in a mammal, wherein a synthetic peptide amide of the invention is co-administered with a reduced dose of a mu opioid agonist analgesic compound to produce a therapeutic analgesic effect, the mu opioid agonist analgesic compound having an associated side effect, (especially respiratory depression, sedation, euphoria, antidiuresis, nausea, vomiting, constipation, and physical tolerance, dependence, and addiction). The reduced dose of the mu opioid agonist analgesic compound administered by this method has lower associated side effects than the side effects associated with the dose of the compound necessary to achieve the same therapeutic analgesic effect when administered alone.

The invention also provides a method of treating or preventing peripheral hyperalgesia, wherein the method includes topically applying or locally administering to a mammal in need of the treatment, an effective amount of a composition that includes an anti-hyperalgesically-effective amount of a synthetic peptide amide of the invention in a vehicle formulated for topical application or local administration.

The invention also provides a method of treating or preventing hyponatremia or hypokalemia, and thereby treating or preventing a disease or condition associated with hyponatremia or hypokalemia, such as congestive heart failure, liver cirrhosis, nephrotic syndrome, hypertension, or edema, and preferably where increased vasopressin secretion is associated with said disease or disorder, wherein the method includes administering to a mammal an aquaretically effective amount of a synthetic peptide amide of the invention in a pharmaceutically acceptable diluent, excipient or carrier.

25% piperidine, DMF; d) Fmoc-D-Orn(Boc)-OH, DIC, HOBt, DMF; e) Fmoc-D-Leu-OH, DIC, HOBt, DMF; f) Fmoc-D-Phe-OH, DIC, HOBt, DMF; g) Boc-D-Phe-OH, DIC, HOBt, DMF; h) TFA/TIS/H2O (95:2.5:2.5).

Figure 3:
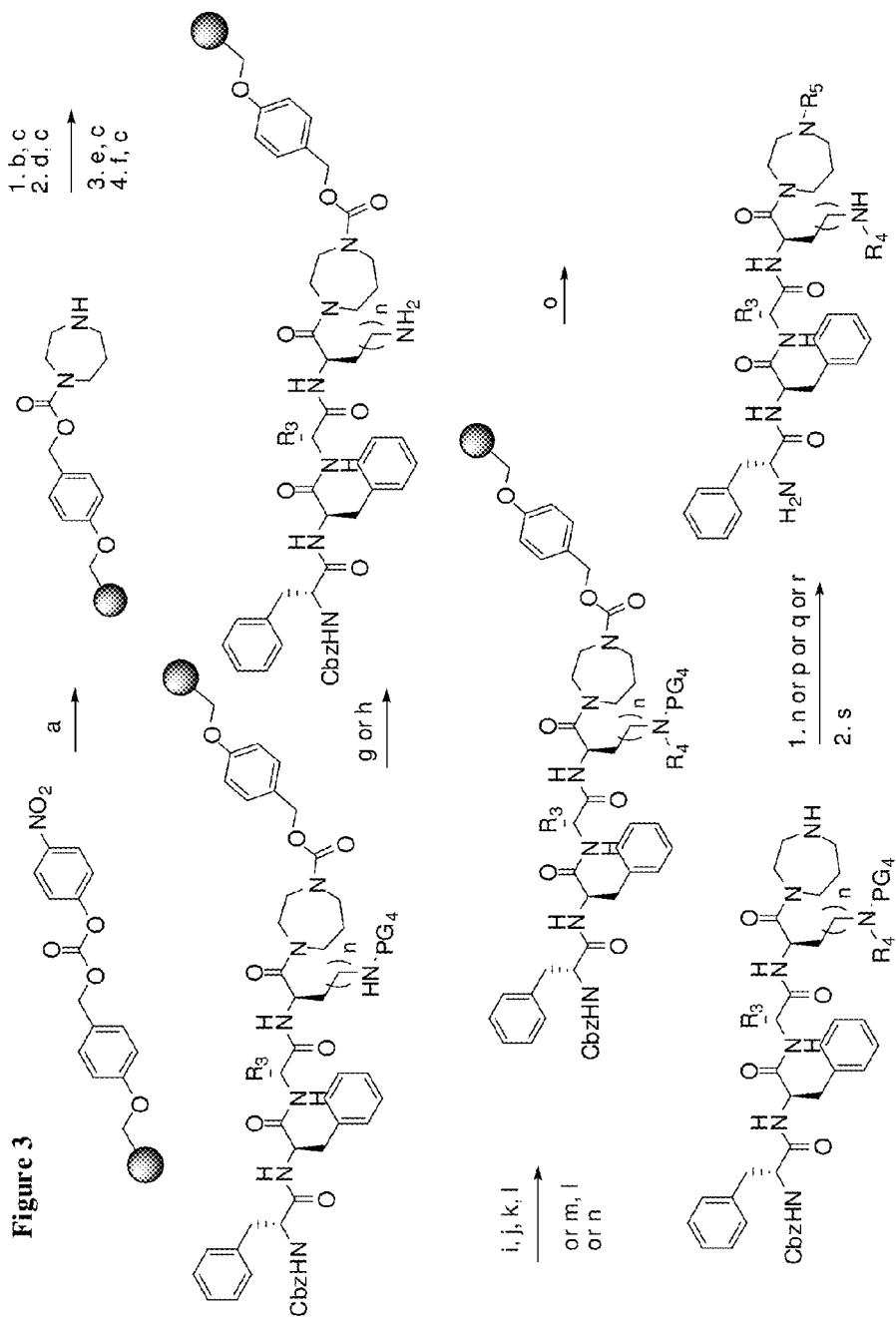

FIG. 3: Shows the general scheme used in the synthesis of tetrapeptide homopiperazine derivatives such as compound (11). Steps a-s were carried out with the following reactants or conditions: a) homopiperazine, DCM; b) Fmoc-D-Dap (ivDde)-OH or Fmoc-D-Dab(ivDde)-OH or Fmoc-D-Orn (Aloc)-OH or Fmoc-D-Orn(Z)-OH or Fmoc-D-Lys(Dde)-OH or Fmoc-D-Arg(Pbf)-OH, DIC, HOBt, DMF; c) 25% piperidine in DMF; d) Fmoc-D-Leu-OH or Fmoc-D-Nle-OH, DIC, HOBt, DMF; e) Fmoc-D-Phe-OH, DIC, HOBt, DMF; f) Z-D-Phe-OH, DIC, HOBt, DMF; n=0-3; R3=iPr, nPr; PG4=ivDde, Dde, Aloc, Z, Pbf in case of D-Arg; g) 4% hydrazine in DMF; h) Pd(PPh3)4, CHCl3/AcOH/NMM; i) O-NBS-Cl, collidine, NMP; j) dimethylsulfate, DBU, NMR; k) mercaptoethanol, DBU, NMP; l) Z-OSu, DMF; m) acetone, AcOH, NaBH(OAc)3, TMOF; n) 1H-pyrazole-1-carboxamidine, DIEA, DMF; n=0-3; R3=iPr, nPr; R4=H, Me, iPr, amidino; PG4=Z, H if R4 is amidino; o) 50% TFA/DCM; p) S-Methyl-N-methylisothiourea hydroiodide, DIEA, DMF; q) 2-methylthio-2-imidazoline hydroiodide, DIEA, DMF; r) iodoethane, DIEA, DMF; s) TMSOTf/TFA/m-cresol (2:7:1); n=0-3; R3=iPr, nPr; R4=H, Me, iPr, amidino; R5=H, Et, amidino, 4,5-dihydro-1H-imidazol-2-yl, N-methylcarbamimidoyl.

Figure 4:
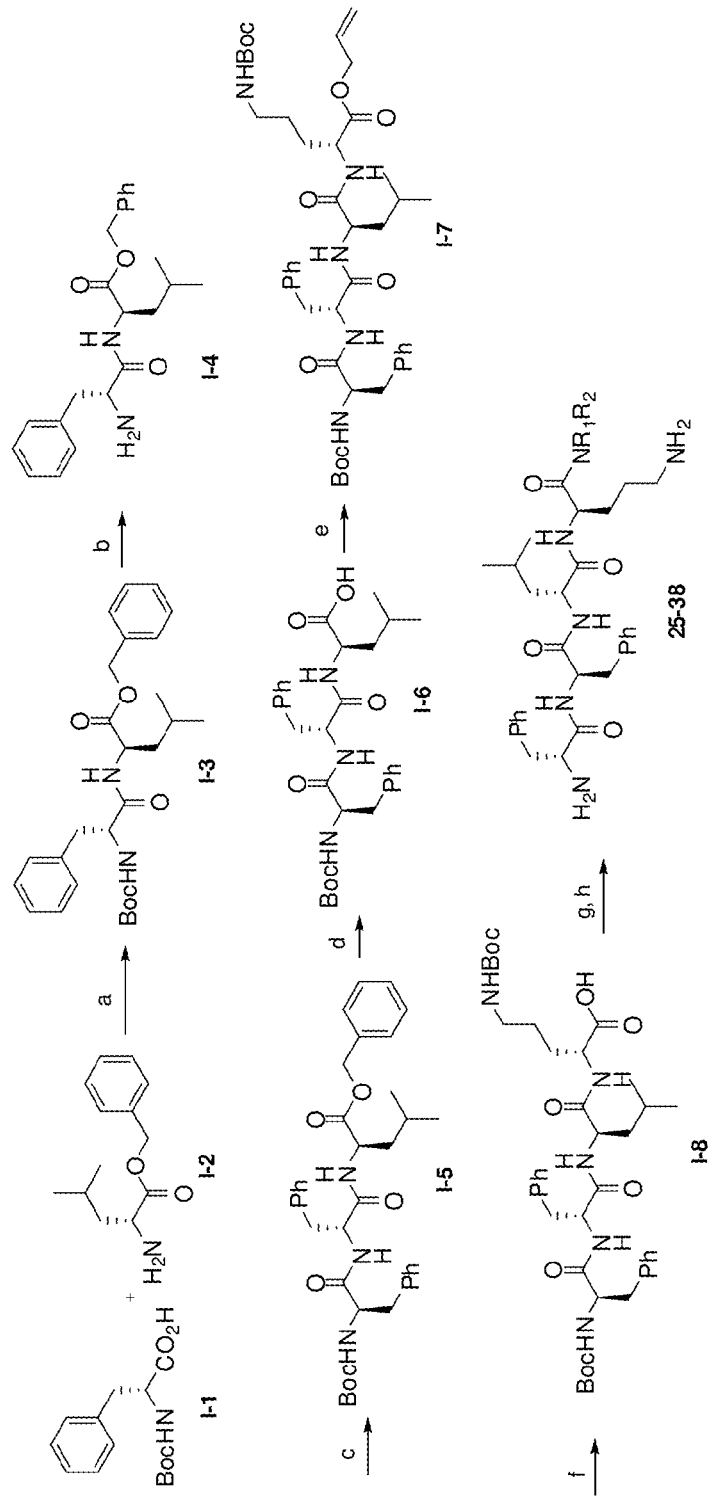

FIG. 4: Shows the general scheme used in the synthesis of compounds (25)-(38). Steps a-h were carried out with the following reactants or conditions: a) EDC, HOBt, DIEA, THF; b) TFA, DCM; c) Boc-D-Phe-OH, EDC, HOBt, DIEA; d) H$_2$, Pd/C; e) H-D-Lys(Boc)-OAll, TBTU, DIEA, DMF; f) Pd(PPh$_3$)$_4$, pyrrolidine; g) amine HNR$_1$R$_2$, HBTU, DMF; h) HCl, dioxane.

Figure 5:
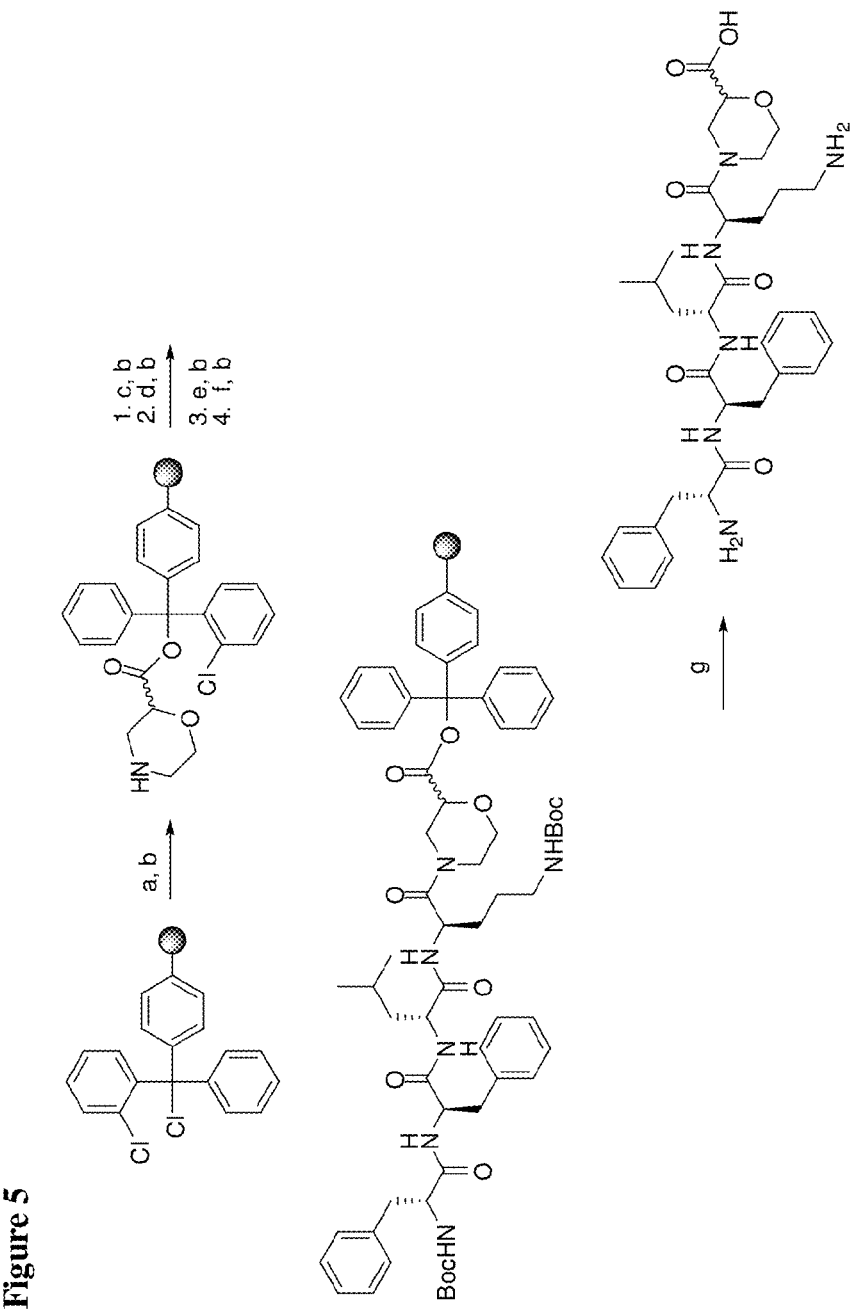

FIG. 5: Shows the general scheme used in the synthesis of compound (40): D-Phe-D-Phe-D-Leu-D-Orn-[ε-Lys(D-Orn-D-Leu-H)]-H (SEQ ID NO: 1). Steps a-i were carried out with the following reactants or conditions: a) Fmoc-L-Lys(Dde)-OH, DIEA, DCM; b) 25% piperidine/DMF; c) Fmoc-D-Orn (Boc)-OH, PyBOP, DIEA, DMF; d) Boc-D-Leu-OH, PyBOP, DIEA, DMF; e) 4% hydrazine, DMF; f) Fmoc-D-Leu-OH, PyBOP, DIEA, DMF; g) Fmoc-D-Phe-OH, PyBOP, DIEA, DMF; h) Boc-D-Phe-OH, PyBOP, DIEA, DMF; i) TFA/TIS/H2O (95:2.5:2.5).

Figure 6:
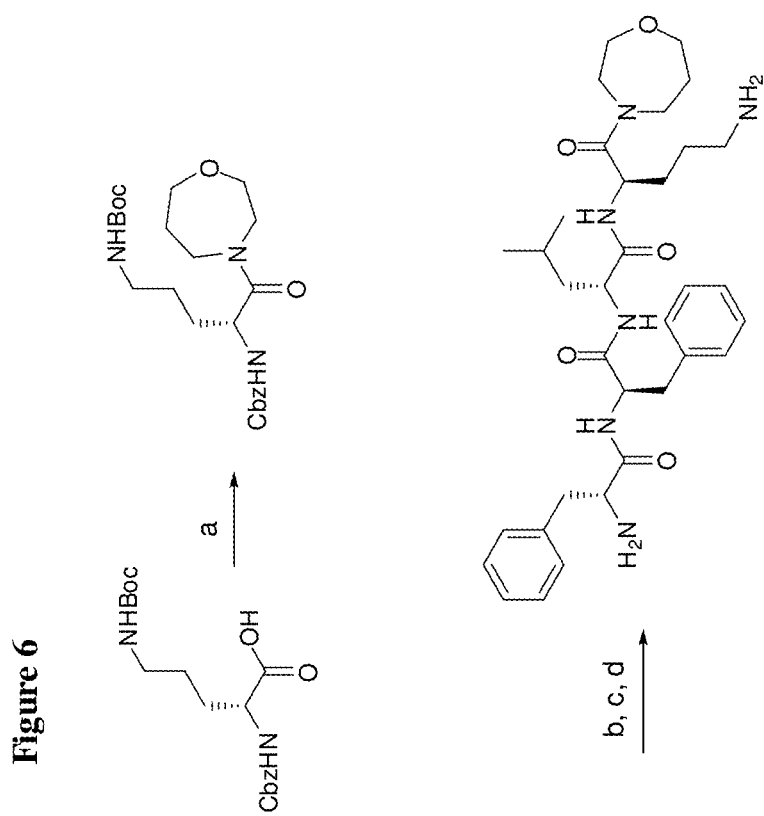

FIG. 6: Shows the general scheme used in the synthesis of compound (51): 1N,4N-bis-(D-Phe-D-Phe-D-Leu-D-Nar)-4amino-4carboxylic piperidine (SEQ ID NO: 6). Steps a-k were carried out with the following reactants or conditions: a) 35% piperidine, DMF; b) N-Boc-(4-Fmoc-amino)piperidine-4-carboxylic acid, PyBOP, DIEA, DMF; c) 30% TFA/DCM; d) Boc-D-Dab(Fmoc)-OH, PyBOP, DIEA, DMF; e) Boc-D-Leu-OH, PyBOP, DIEA, DMF; f) Boc-D-Phe-OH, PyBOP, DIEA, DMF; g) Boc-D-Phe-OH, PyBOP, DIEA, DMF; h) 2% DBU/DMF; i) 1H-pyrazole-1-carboxamidine, DIEA, DMF; j) copper acetate, pyridine, DBU, DMF/water; k) 95% TFA/water.

Figure 7:
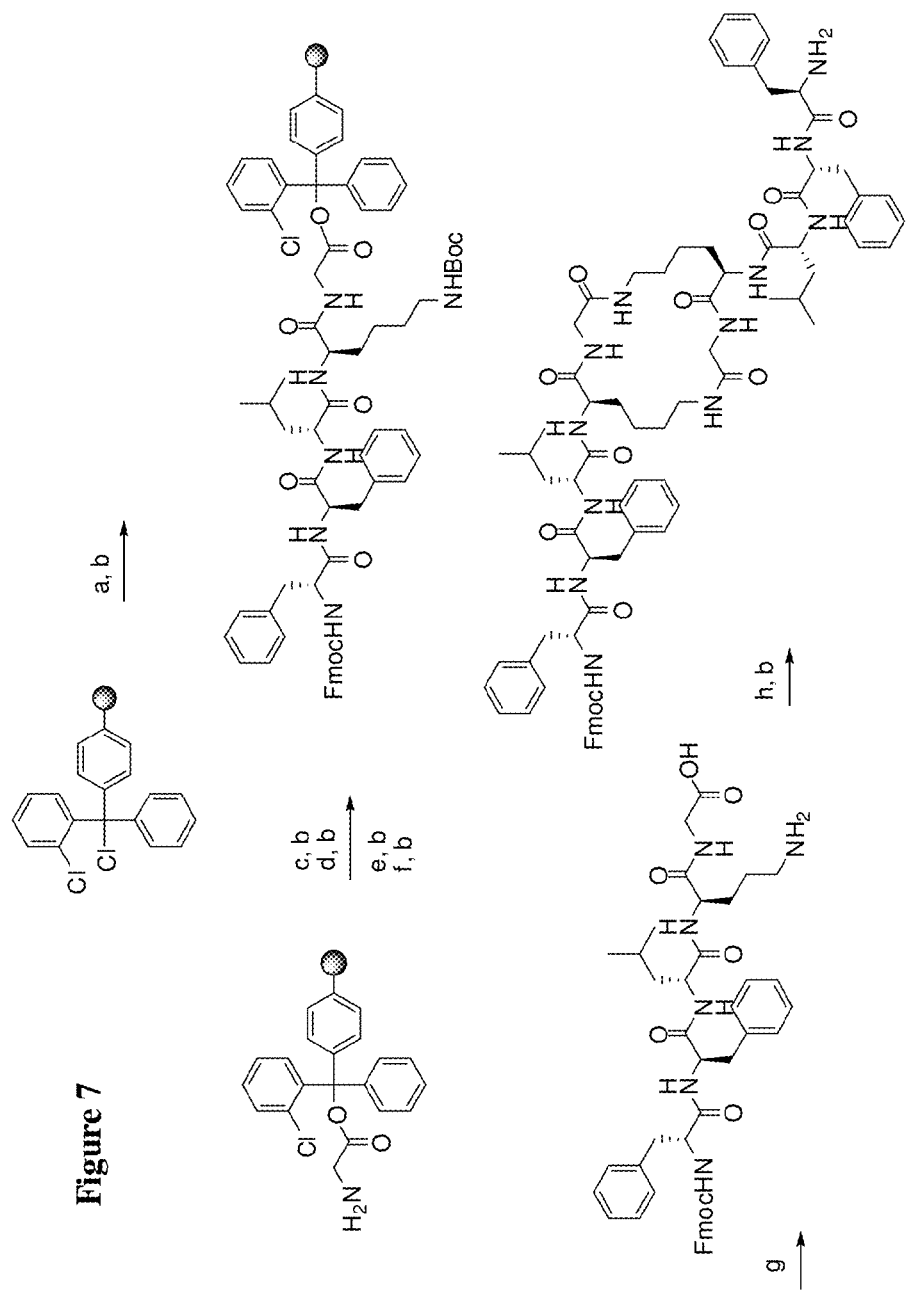
Figure 8:
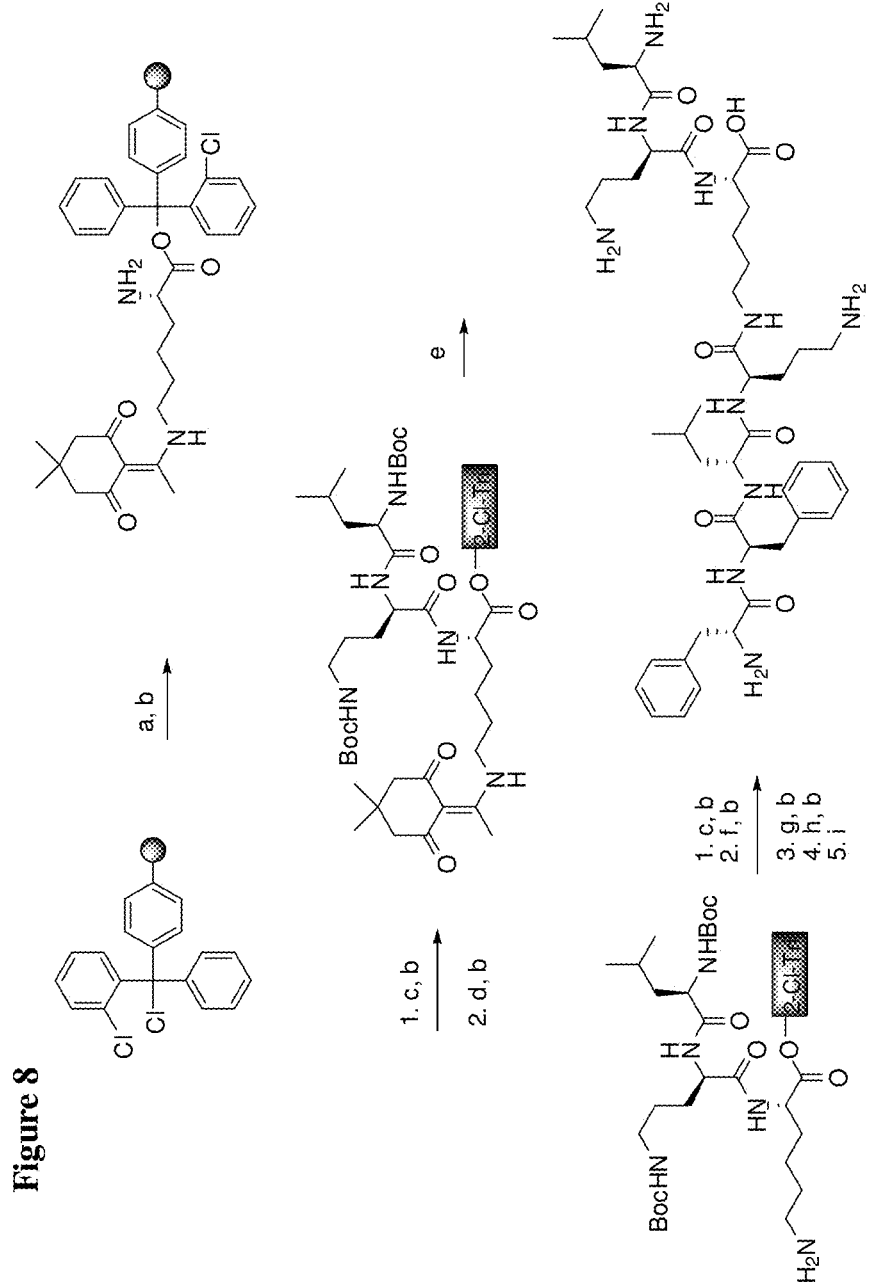

FIG. 7: Shows the general scheme used in the synthesis of compound (52): D-Phe-D-Phe-D-Leu-(D-Lys-GlyLactam)$_2$-D-Leu-D-Phe-D-Phe. Steps a-h were carried out with the following reactants or conditions: a) Fmoc-Glycine, DIEA, DCM; b) 25% piperidine/DMF; c) Fmoc-D-Lys(Boc)-OH, PyBOP, DIEA, DMF; d) Fmoc-D-Leu-OH, PyBOP, DIEA, DMF; e) Fmoc-D-Phe-OH, PyBOP, DIEA, DMF; f) Boc-D-Phe-OH, PyBOP, DIEA, DMF; g) TFA/TIS/H2O; h) PyBOP, DIEA, DMF;

FIG. 8: Shows the general scheme used in the synthesis of compound (53): D-Phe-D-Phe-D-Leu-D-Orn-[R/S-2-carboxymorpholine]-OH (SEQ ID NO: 1). Steps a-g were carried out with the following reactants or conditions: a) Fmoc-morpholine-2-carboxylic acid, DIEA, DCM; b) 25% piperidine/DMF; c) Fmoc-D-Orn(Boc)-OH, DIC, HOBt, DMF; d) Fmoc-D-Leu-OH, DIC, HOBt, DMF; e) Fmoc-D-Phe-OH, DIC, HOBt, DMF; f) Boc-D-Phe-OH, DIC, HOBt, DMF; g) TFA/TIS/H2O (95:2.5:2.5).

Figure 9:
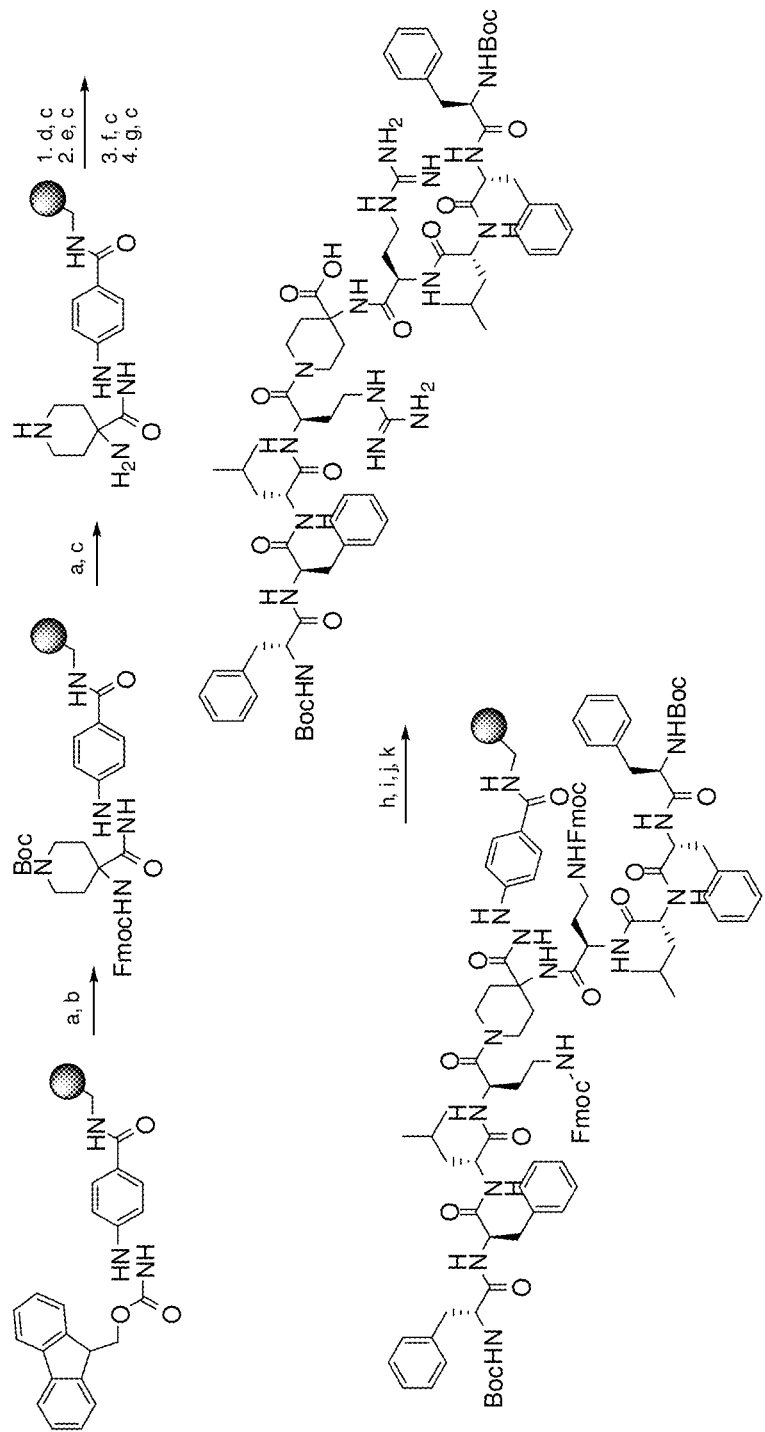

FIG. 9: Shows the general scheme used in the synthesis of compound (55): D-Phe-D-Phe-D-Leu-D-Orn-N(homomorpholine) (SEQ ID NO: 1). Steps a-d were carried out with the following reactants or conditions: a) homomorpholine, EDC, HOBt, THF; b) H2, Pd/C, MeOH; c) Boc-D-Phe-D-Phe-D-Leu-OH, EDC, HOBt, THF; d) TFA, DCM.

Figure 10:
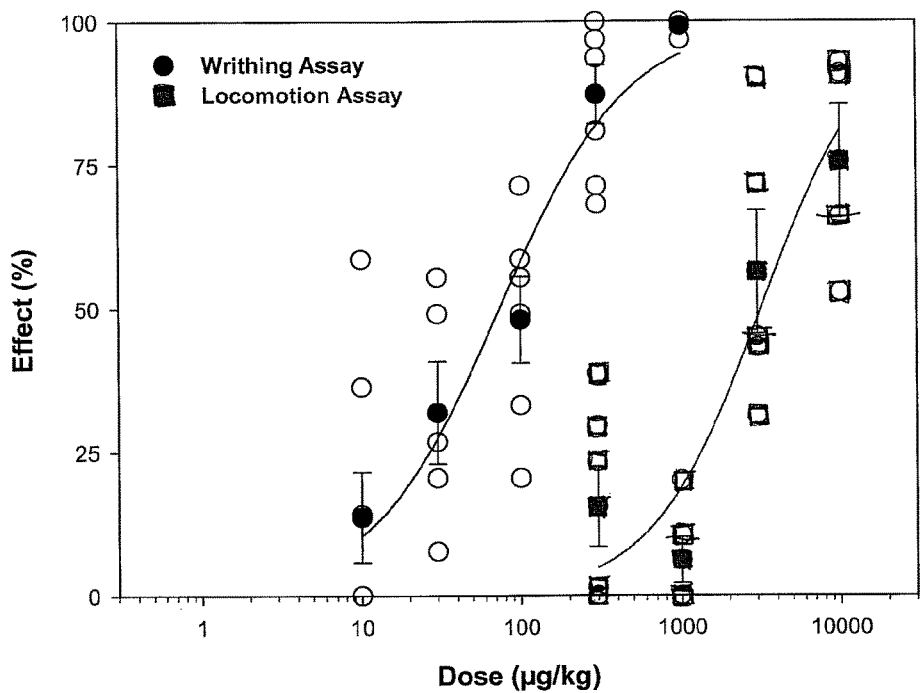

FIG. 10: Dose response curves for compound (17) in IRC mice in the acetic acid-induced writhing assay (open circles) and the mean (closed circles) and error bars; and in the locomotion assay (open squares) and the mean (closed squares) and error bars.

Figure 11:
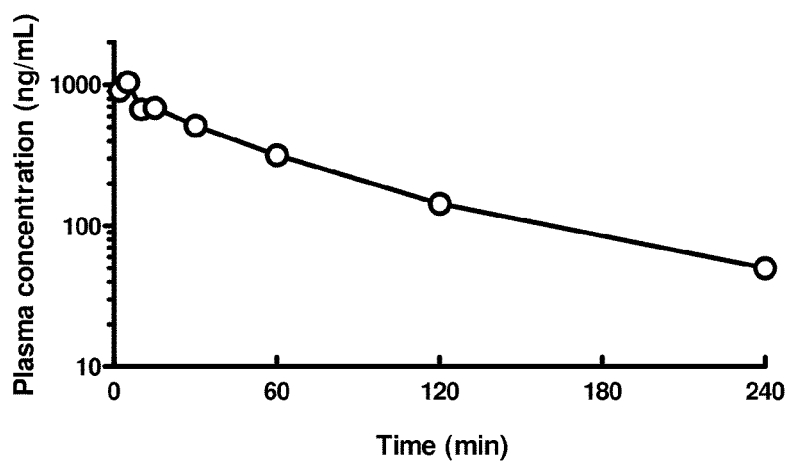

FIG. 11: Plasma concentrations after intravenous administration of a single bolus of compound (19) to cynomolgus monkeys. Plasma was sampled at 2, 5, 10, 15, 30, 60, 120, and 240 minutes post injection.

DETAILED DESCRIPTION

As used throughout this specification, the term "synthetic peptide amide" means a compound of the invention conforming to formula I, or a stereoisomer, mixture of stereoisomers, prodrug, pharmaceutically acceptable salt, hydrate, solvate, acid salt hydrate, N-oxide or isomorphic crystalline form thereof. The designations $Xaa_1$, $Xaa_2$, $Xaa_3$, and $Xaa_4$ represent D-amino acids in the synthetic peptide amides of the invention. Stereoisomers of the synthetic peptide amides of the invention conforming to formula I are limited to those compounds having amino acids in the D-configuration where so specified in Formula I. Stereoisomers of the synthetic peptide amides of the invention include compounds having either a D- or L-configuration at chiral centers other than the alpha carbons of the four amino acids at $Xaa_1$, $Xaa_2$, $Xaa_3$, and $Xaa_4$. The term 'mixtures of stereoisomers' refer to mixtures of such stereoisomers of the invention. As used herein 'racemates' refers to mixtures of stereoisomers having equal proportions of compounds with D- and L-configuration at one or more of the chiral centers other than the alpha carbons of $Xaa_1$, $Xaa_2$, $Xaa_3$, and $Xaa_4$ without varying the chirality of the alpha carbons of $Xaa_1$, $Xaa_2$, $Xaa_3$, and $Xaa_4$.

The nomenclature used to define peptides herein is specified by Schroder & Lubke, *The Peptides*, Academic Press, 1965, wherein, in accordance with conventional representation, the N-terminus appears to the left and the C-terminus to the right. Where an amino acid residue has isomeric forms, both the L-isomer form and the D-isomer form of the amino acid are intended to be covered unless otherwise indicated. Amino acids are commonly identified herein by the standard three-letter code. The D-isomer of an amino acid is specified by the prefix "D-" as in "D-Phe" which represents D-phenylalanine, the D-isomer of phenylalanine. Similarly, the L-isomer is specified by the prefix "L-" as in "L-Phe." Peptides are represented herein according to the usual convention as amino acid sequences from left to right: N-terminus to C-terminus, unless otherwise specified.

As used herein, D-Arg represents D-arginine, D-Har represents D-homoarginine, which has a side chain one methylene group longer than D-Arg, and D-Nar represents D-norarginine, which has a side chain one methylene group shorter than D-Arg. Similarly, D-Leu means D-leucine, D-Nle means D-norleucine, and D-Hle represents D-homoleucine. D-Ala means D-alanine, D-Tyr means D-tyrosine, D-Trp means D-tryptophan, and D-Tic means D-1,2,3,4-tetrahydroisoquinoline-3carboxylic acid. D-Val means D-valine and D-Met means D-methionine. D-Pro means D-proline, Pro-amide means the D- or L-form of proline amide. D-Pro amide represents D-proline with an amide formed at its carboxy moiety wherein the amide nitrogen may be alkyl substituted, as in —$NR_aR_b$, wherein $R_a$ and $R_b$ are each independently a $C_1$-$C_6$ alkyl group, or one of $R_a$ and $R_b$ is —H. Gly means glycine, D-Ile means D-isoleucine, D-Ser means D-serine, and D-Thr means D-threonine. (E)D-Ala means the D-isomer of alanine which is substituted by the substituent (E) on the β-carbon. Examples of such substituent (E) groups include cyclobutyl, cyclopentyl, cyclohexyl, pyridyl, thienyl and thiazoyl. Thus, cyclopentyl-D-Ala means the D-isomer of alanine which is substituted by cyclopentyl on the β-carbon. Similarly, D-Ala(2-thienyl) and (2-thienyl)D-Ala are interchangeable and both mean the D-isomer of alanine substituted at the β-carbon with thienyl that is attached at the 2-ring position.

As used herein, D-Nal means the D-isomer of alanine substituted by naphthyl on the β-carbon. D-2Nal means naphthyl substituted D-alanine wherein the attachment to naphthalene is at the 2-position on the ring structure and D-1Nal means naphthyl-substituted D-alanine wherein the attachment to naphthalene is at the 1-position on the ring structure. By (A)(A')D-Phe is meant D-phenylalanine substituted on the phenyl ring with one or two substituents independently chosen from halo, nitro, methyl, halomethyl (such as, for example, trifluoromethyl), perhalomethyl, cyano and carboxamide. By D-(4-F)Phe is meant D-phenylalanine which is fluoro-substituted in the 4-position of the phenyl ring. By D-(2-F)Phe is meant D-phenylalanine which is fluoro-substituted in the 2-position of the phenyl ring. By D-(4-Cl)Phe is meant D-phenylalanine which is chloro substituted in the 4-phenyl ring position. By (α-Me)D-Phe is meant D-phenylalanine which is methyl substituted at the alpha carbon. By (α-Me)D-Leu is meant D-leucine which is methyl substituted at the alpha carbon.

The designations $(B)_2$D-Arg, $(B)_2$D-Nar, and $(B)_2$D-Har represent D-arginine, D-norarginine and D-homoarginine, respectively, each having two substituent (B) groups on the side chain. D-Lys means D-lysine and D-Hlys means D-homolysine. ζ-(B)D-Hlys, ε-(B)D-Lys, and ε-$(B)_2$-D-Lys represent D-homolysine and D-lysine each having the side chain amino group substituted with one or two substituent (B) groups, as indicated. D-Orn means D-ornithine and δ-(B)α-(B')D-Orn means D-ornithine substituted with (B') at the alpha carbon and substituted with (B) at the side chain δ-amino group.

D-Dap means D-2,3-diaminopropionic acid. D-Dbu represents the D-isomer of alpha, gamma-diamino butyric acid and $(B)_2$D-Dbu represents alpha, gamma-diamino butyric acid which is substituted with two substituent (B) groups at the gamma amino group. Unless otherwise stated, each of the (B) groups of such doubly substituted residues are independently chosen from H— and $C_1$-$C_4$-alkyl. As used herein, D-Amf means D-($NH_2CH_2$-)Phe, i.e., the D-isomer of phenylalanine substituted with aminomethyl on its phenyl ring and D-4Amf represents the particular D-Amf in which the aminomethyl is attached at the 4-position of the ring. D-Gmf means D-Amf (amidino) which represents D-Phe wherein the phenyl ring is substituted with —$CH_2NHC(NH)NH_2$. Amd represents amidino, —$C(NH)NH_2$, and the designations (Amd)D-Amf and D-Amf(Amd) are also interchangeably used for D-Gmf. The designations Ily and Ior are respectively used to mean isopropyl Lys and isopropyl Orn, wherein the side chain amino group is alkylated with an isopropyl group.

Alkyl means an alkane radical which can be a straight, branched, and cyclic alkyl group such as, but not limited to, methyl, ethyl, propyl, isopropyl, cyclopropyl, butyl, t-butyl, sec-butyl, pentyl, cyclopentyl, hexyl, cyclohexyl, cyclohexylethyl. $C_1$ to $C_8$ alkyl refers to alkyl groups having between one and eight carbon atoms. Similarly, $C_1$-$C_6$ alkyl refers to alkyl groups having between one and six carbon atoms. Likewise, $C_1$-$C_4$ alkyl refers to alkyl groups having between one and four carbon atoms. By lower alkyl is meant $C_1$-$C_6$ alkyl. Me, Et, Pr, Ipr, Bu, and Pn are interchangeably used to represent the common alkyl groups: methyl, ethyl, propyl, isopropyl, butyl, and pentyl, respectively. Although the linkage for an alkyl group is typically at one end of an alkyl chain, the linkage may be elsewhere in the chain, e.g. 3-pentyl which may also be referred to as ethylpropyl, or 1-ethylprop-1-yl. Alkyl-substituted, such as $C_1$ to $C_6$ alkyl-substituted amidino, indicates that the relevant moiety is substituted with one or more alkyl groups.

Where a specified moiety is null, the moiety is absent and if such moiety is indicated to be attached to two other moieties, such two other moieties are connected by one covalent bond. Where a connecting moiety is shown herein as attached to a ring at any position on the ring, and attached to two other moieties, such as $R_1$ and $R_2$, in the case where the connecting moiety is specified to be null, then the $R_1$ and $R_2$ moieties can each be independently attached to any position on the ring.

The terms "heterocycle", "heterocyclic ring" and "heterocyclyl" are used interchangeably herein and refer to a ring or ring moiety having at least one non-carbon ring atom, also called a heteroatom, which may be a nitrogen, a sulfur, or an oxygen atom. Where a ring is specified as having a certain number of members, the number defines the number of ring atoms without reference to any substituents or hydrogen atoms bonded to the ring atoms. Heterocycles, heterocyclic rings and heterocyclyl moieties can include multiple heteroatoms independently selected from nitrogen, sulfur, or oxygen atom in the ring. Rings may be substituted at any available position. For example, but without limitation, 6- and 7-membered rings are often substituted in the 4-ring position and 5-membered rings are commonly substituted in the 3-position, wherein the ring is attached to the peptide amide chain at the 1-ring position.

The term 'saturated' refers to an absence of double or triple bonds and the use of the term in connection with rings describes rings having no double or triple bonds within the ring, but does not preclude double or triple bonds from being present in substituents attached to the ring. The term "non-aromatic" refers in the context of a particular ring to an absence of aromaticity in that ring, but does not preclude the presence of double bonds within the ring, including double bonds which are part of an aromatic ring fused to the ring in question. Nor is a ring atom of a saturated heterocyclic ring moiety precluded from being double-bonded to a non-ring atom, such as for instance a ring sulfur atom being double-bonded to an oxygen atom substituent. As used herein, heterocycles, heterocyclic rings and heterocyclyl moieties also include saturated, partially unsaturated and heteroaromatic rings and fused bicyclic ring structures unless otherwise specified. A heterocycle, heterocyclic ring or heterocyclyl moiety can be fused to a second ring, which can be a saturated, partially unsaturated, or aromatic ring, which ring can be a heterocycle or a carbocycle. Where indicated, two substituents can be optionally taken together to form an additional ring. Rings may be substituted at any available position. A heterocycle, heterocyclic ring and heterocyclyl moiety can, where indicted, be optionally substituted at one or more ring positions with one or more independently selected substituents, such as for instance, $C_1$-$C_6$ alkyl, $C_3$-$C_8$ cycloalkyl, $C_1$-$C_6$ alkoxy, halo $C_1$-$C_6$ alkyl, optionally substituted phenyl, aryl, heterocyclyl, oxo, —OH, —Cl, —F, —$NH_2$, —$NO_2$, —CN, —COOH and amidino. Suitable optional substituents of the phenyl substituent include for instance, but without limitation, one or more groups selected from $C_1$-$C_3$ alkyl, $C_1$-$C_3$ alkoxy, halo $C_1$-$C_3$ alkyl, oxo, —OH, —Cl, —F, —$NH_2$, —$NO_2$, —CN, —COOH and amidino.

D-Phe and substituted D-Phe are examples of a suitable amino acid for residue $Xaa_1$ in Formula I. The phenyl ring can be substituted at any of the 2-, 3- and/or 4-positions. Particular examples of permitted substitutions include, for instance, chlorine or fluorine at the 2- or 4-positions. Also the alpha-carbon atom may be methylated. Other equivalent residues which represent conservative changes to D-Phe can also be used. These include D-Ala(cyclopentyl), D-Ala(thienyl), D-Tyr and D-Tic. The residue at the second position, $Xaa_2$ can also be D-Phe or substituted D-Phe with such substitutions including a substituent on the 4-position carbon of the phenyl ring, or on both the 3- and 4-positions. Alternatively, $Xaa_2$ can be D-Trp, D-Tyr or D-alanine substituted by naphthyl. The third position residue, $Xaa_3$ can be any non-polar amino acid residue, such as for instance, D-Nle, D-Leu, ($\alpha$-Me)D-Leu, D-Hle, D-Met or D-Val. However, D-Ala(cyclopropyl, cyclobutyl, cyclopentyl or cyclohexyl) or D-Phe can also be used as $Xaa_3$. The fourth position residue $Xaa_4$ can be any positively charged amino acid residue, such as for instance, D-Arg and D-Har, which can be optionally substituted with lower alkyl groups, such as one or two ethyl groups. Alternatively, D-Nar and any other equivalent residues can be used, such as, for instance, D-Lys or D-Orn (either of which can be ω-amino group alkylated, for example by methyl or isopropyl groups, or methylated at the α-carbon group). Moreover, D-Dbu, D-4-Amf (which can be optionally substituted with amidino), and D-Hlys are also suitable amino acids at this position.

Compounds of the invention contain one or more chiral centers, each of which has two possible three-dimensional spatial arrangements (configurations) of the four substituents around the central carbon atom. These are known as stereoisomers, and more specifically as enantiomers (all chiral centers inverted) or diastereoisomers (two or more chiral centers, at least one chiral center remaining the same). In a specific embodiment of the invention, the amino acids which make up the tetrapeptide backbone, $Xaa_1Xaa_2Xaa_3Xaa_4$ are specified to be D-amino acids i.e., the opposite configuration to those generally found in mammals. Reference to stereoisomers of the synthetic peptide amides of the invention concerns chiral centers other than the alpha carbons of the D-amino acids which make up $Xaa_1$-$Xaa_4$. Thus, stereoisomers of synthetic peptide amides that are embodiments of the invention wherein each of $Xaa_1$-$Xaa_4$ are specified to be D-amino acids, do not include L-amino acids or racemic mixtures of the amino acids at these positions. Similarly, reference to racemates herein concerns a center other than the alpha carbons of the D-amino acids which make up $Xaa_1$-$Xaa_4$. Chiral centers in the synthetic peptide amides of the invention for which a stereoisomer may take either the R or S configuration include chiral centers in the moiety attached to the carboxy-terminus of $Xaa_4$, and also chiral centers in any amino acid side chain substituents of $Xaa_1$-$Xaa_4$.

The synthetic peptide amides of the invention described herein (also interchangeably referred to as synthetic peptide amide compounds, compounds of the invention, compound (number), or simply "the compounds") can be used or prepared in alternate forms. For example, many amino-containing compounds can be used or prepared as an acid salt. Often such salts improve isolation and handling properties of the compound. For example, depending on the reagents, reaction conditions and the like, compounds such as the synthetic peptide amides described herein can be used or prepared, for example, as the hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic synthetic peptide amides of the present invention may exist as zwitterions. All forms of these synthetic peptide amide compounds, including free acid, free base and zwitterions, are contemplated to be within the scope of the present invention. It is well known in the art that compounds containing both amino and carboxyl groups often exist in equilibrium with their zwitterionic forms. Thus, for any compound described herein that contains, for example, both amino and carboxyl groups, it will also be understood to include the corresponding zwitterion.

In one embodiment, the present invention provides synthetic peptide amides having the formula:

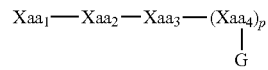

and a stereoisomers, mixture of stereoisomers, prodrugs, pharmaceutically acceptable salts, hydrates, solvates, acid salt hydrates, N-oxides and isomorphic crystalline forms thereof, wherein each $Xaa_1$ is independently chosen from (A)(A')D-phenylalanine, (A)(A')($\alpha$-Me)D-phenylalanine, D-tyrosine, D-1,2,3,4-tetrahydroisoquinoline-3carboxylic acid, D-phenylglycine, D-neopentylglycine, D-phenylglycine, D-homophenylalanine, and β-(E)D-Ala, wherein (A) and (A') are each phenyl ring substituents independently chosen from —H, —F, —Cl, —$NO_2$, —$CH_3$, —$CF_3$, —CN, —$CONH_2$, and wherein each (E) is independently chosen from cyclobutyl, cyclopentyl, cyclohexyl, pyridyl, thienyl and thiazolyl. Each $Xaa_2$ is independently chosen from (A)(A')D-phenylalanine, (A)(A')($\alpha$-Me)D-phenylalanine, naphthyl-1-D-alanine, naphthyl-2-D-alanine, D-tyrosine, (E)D-alanine, and D-tryptophan. Each $Xaa_3$ is independently chosen from D-norleucine, D-phenylalanine, (E)D-alanine, D-leucine, ($\alpha$-Me)D-leucine, D-homoleucine, D-valine, and D-methionine. Each $Xaa_4$ is independently chosen from $(B)_2$D-arginine, $(B)_2$D-norarginine, $(B)_2$D-homoarginine, ζ-(B)D-homolysine, D-2,3-diaminopropionic acid, ε-(B)D-lysine, ε-$(B)_2$-D-lysine, D-($NH_2CH_2$-)phenylalanine, amidino-D-($NH_2CH_2$-) phenylalanine, γ-$(B)_2$D-diamino butyric acid, δ-$(B)_2$α-(B')D-ornithine, D-2-amino-3(4-piperidyl) propionic acid, D-2-amino-3(2-aminopyrrolidyl)propionic acid, D-α-amino-β-amidino-propionic acid, α-amino-4-piperidineacetic acid, cis-α,4-diaminocyclohexane acetic acid, trans-α,4-diaminocyclohexaneacetic acid, cis-α-amino-4-methyl-aminocyclo-hexane acetic acid, trans-α-amino-4-methylaminocyclohexane acetic acid, α-amino-1-amidino-4-piperidineacetic acid, cis-α-amino-4-guanidinocyclohexane acetic acid, and trans-α-amino-4-guanidinocyclohexane acetic acid, wherein each (B) is independently selected from the group consisting of —H and $C_1$-$C_4$ alkyl, and (B') is —H or (α-Me); and p is zero or 1.

In another embodiment G is selected from one of the following four moieties:

(i) G is

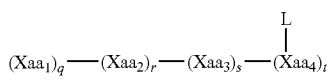

wherein p, q, r, s and t are each independently zero or 1, provided that at least one of s and t are 1; and L is a linker chosen from ε-D-lysine, ε-lysine, δ-D-ornithine, δ-ornithine, γ-amino-butyric acid, 8-aminooctanoic acid, 11-amino-undecanoic acid, 8-amino-3,6-dioxa-octanoic acid, 4-amino-4-carboxylic piperidine and (D-Lys-Gly lactam)$_2$. The synthetic peptide amides of this embodiment are also herein interchangeably referred to as 'dimers,' 'dimeric structures' or 'synthetic peptide amide dimers' since they include two synthetic peptide amide components joined by the linking moiety, L.

(ii) G is

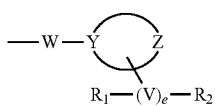

wherein p is 1; $Xaa_3$-$Xaa_4$- is chosen from D-Nle-(B)$_2$D-arginine-, D-leucine-δ-(B)$_2$α-(B')D-ornithine-, and (α-Me) D-leucine-δ(B)$_2$-α(B')D-ornithine-; and the Y- and Z-containing ring moiety,

is an optionally substituted 4 to 8-membered heterocyclic ring moiety wherein all ring heteroatoms in said ring moiety are nitrogen atoms; wherein Y and Z are each independently a carbon atom or a nitrogen atom; provided that when such ring moiety is a six, seven or eight-membered ring, Y and Z are separated by at least two ring atoms; and provided that when such ring moiety has a single heteroatom which is a nitrogen atom, then such ring moiety is non-aromatic.

(iii) G is

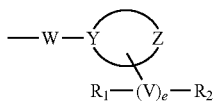

wherein p is 1;
and the moiety

is an optionally substituted 4 to 8-membered heterocyclic ring moiety wherein Y is C or N and Z is a carbon atom, a nitrogen atom, an oxygen atom, a sulfur atom, a sulfoxide group, or a sulfonyl group; provided that when such ring moiety is a six-, seven- or eight-membered ring, Y and Z are separated by at least two ring atoms; provided that when such ring moiety is non-aromatic and Z is a carbon atom or a nitrogen atom then such ring moiety comprises at least one sulfur or oxygen ring heteroatom; and provided further that when such ring moiety is aromatic, then Y is a carbon atom; and (iv) G is

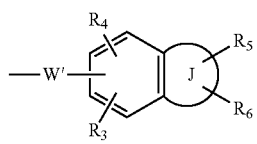

wherein J is a 5-, 6-, or 7-membered heterocyclic ring moiety comprising 1, 2, or 3 heteroatoms in the ring, wherein $R_3$ and $R_4$ are each independently selected from $C_1$-$C_3$ alkyl, halo, —OH, —CF$_3$, —NH$_2$, —COOH and amidino; and $R_5$ and $R_6$ are each independently chosen from $C_1$-$C_3$ alkyl, oxo, halo, —OH, —CF$_3$, —NH$_2$, —COOH and amidino; wherein W' is chosen from:
null;
—NH—(CH$_2$)$_b$— with b equal to zero, 1, 2, 3, 4, 5, or 6; and
—NH—(CH$_2$)$_c$—O— with c equal to 2 or 3.

In another embodiment, V is $C_1$-$C_6$ alkyl, and e is zero or 1, wherein when e is zero, then V is null and, $R_1$ and $R_2$ are directly bonded to the same or different ring atoms; wherein (a) $R_1$ is —H, —OH, halo, CF$_3$, —NH$_2$, —COOH, $C_1$-$C_6$ alkyl, amidino, $C_1$-$C_6$ alkyl-substituted amidino, aryl, optionally substituted heterocyclyl, Pro-amide, Pro, Gly, Ala, Val, Leu, Ile, Lys, Arg, Orn, Ser, Thr, CN, CONH$_2$, COR', SO$_2$R', CONR'R", NHCOR', OR', or SO$_2$NR'R"; wherein said optionally substituted heterocyclyl is optionally singly or doubly substituted with substituents independently selected from the group consisting of $C_1$-$C_6$ alkyl, —$C_1$-$C_6$ alkoxy, oxo, —OH, —Cl, —F, —NH$_2$, —NO$_2$, —CN, —COOH, and amidino; wherein R' and R" are each independently —H, $C_1$-$C_8$ alkyl, aryl, heterocyclyl or R' and R" are combined to form a 4- to 8-membered ring, which ring is optionally substituted singly or doubly with substituents independently selected from the group consisting of $C_1$-$C_6$ alkyl, —$C_1$-$C_6$ alkoxy, —OH, —Cl, —F, —NH$_2$, —NO$_2$, —CN, and —COOH, amidino; and $R_2$ is H, amidino, singly or doubly $C_1$-$C_6$ alkyl-substituted amidino, —CN, —CONH$_2$, —CONR'R", —NHCOR', —SO$_2$NR'R", or —COOH; or (b) $R_1$ and $R_2$ taken together can form an optionally substituted 4- to 9-membered heterocyclic monocyclic or bicyclic ring moiety which is bonded to a single ring atom of the Y and Z-containing ring moiety; or (c) $R_1$ and $R_2$ taken together with a single ring atom of the Y and Z-containing ring moiety can form an optionally substituted 4- to 8-membered heterocyclic ring moiety to form a spiro structure; or (d) $R_1$ and $R_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety; and wherein each of said optionally substituted 4- to 9-membered heterocyclic ring moieties comprising $R_1$ and $R_2$ is optionally singly or doubly substituted with substituents independently selected from the group consisting of $C_1$-$C_6$ alkyl, —$C_1$-$C_6$ alkoxy, optionally substituted phenyl, oxo, —OH, —Cl, —F, —$NH_2$, —$NO_2$, —CN, —COOH, and amidino;

provided that when the Y and Z-containing ring moiety is a six or seven membered ring comprising a single ring heteroatom and when one of Y and Z is C and the other of Y and Z is N, and e is zero, then $R_1$ is not —OH, and $R_1$ and $R_2$ are not both —H; provided further that when the Y and Z-containing ring moiety is a non-aromatic six membered ring comprising two ring heteroatoms, both Y and Z are N, W is null, and —$V_e$($R_1$)($R_2$) is attached to Z, then —$V_e$($R_1$)($R_2$) is selected from the group consisting of amidino, $C_1$-$C_6$ alkyl-substituted amidino, dihydroimidazole, —$CH_2COOH$, and —$CH_2C(O)NH_2$; and lastly, provided that if the Y and Z-containing ring moiety is a six membered ring comprising an S or O ring heteroatom, or if the Y and Z-containing ring moiety is a six membered ring comprising two ring heteroatoms, wherein both Y and Z are N and W is null, or if the Y and Z-containing ring moiety is a six membered aromatic ring comprising a single ring heteroatom, which heteroatom is N, then, when e is zero, $R_1$ and $R_2$ are not both —H.

Also provided in another embodiment are synthetic peptide amides having the formula:

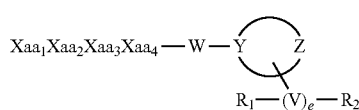

and stereoisomers, mixtures of stereoisomers, racemates, prodrugs, pharmaceutically acceptable salts, hydrates, solvates, acid salt hydrates, N-oxides and isomorphic crystalline forms thereof; wherein $Xaa_1$ is chosen from (A)(A')D-Phe, (α-Me)D-Phe, D-Tyr, D-Tic, D-phenylglycine, D homophenylalanine, and β-(E)D-Ala, wherein (A) and (A') are each phenyl ring substituents independently chosen from —H, —F, —Cl, —$NO_2$, —$CH_3$, —$CF_3$, —CN, and $CONH_2$, and (E) is chosen from cyclobutyl, cyclopentyl, cyclohexyl, pyridyl, thienyl and thiazolyl. $Xaa_2$ is chosen from (A)(A')D-Phe, (α-Me)D-Phe, D-1Nal, D-2Nal, D-Tyr, (E)D-Ala and D-Trp; and $Xaa_3$-$Xaa_4$- is chosen from f D-Nle-(B)$_2$D-Arg-, D-Leu-θ-(B)$_2$α-(B')D-Orn-, and (α-Me)D-Leu-δ(B)$_2$-α(B')D-Orn-; wherein each (B) is independently chosen from —H and $C_1$-$C_4$ alkyl, and (B') is —H or (α-Me). W in the above formula is chosen from one of the following three options:

(i) Null, provided that when W is null, Y is N; or
(ii) —N—($CH_2$)$_b$ with b equal to zero, 1, 2, 3, 4, 5, or 6; or
(iii) —N—($CH_2$)$_c$—O— with c equal to 2, or 3, provided that Y is a carbon atom.

In one embodiment the Y- and Z-containing moiety in the above formula is an optionally substituted 4-8 membered saturated mono- or dinitrogen heterocyclic ring moiety, in which no ring atom other than Y and Z is a heteroatom, Y is C or N, Z is C or N, and at least one of Y and Z is N, and provided that in the case of a 4 or 5 membered heterocyclic ring, either Y or Z is C, and in the case of a dinitrogen heterocycle, Y and Z are separated by two or more ring carbon atoms.

In another embodiment, when the Y- and Z-containing ring moiety is a saturated six-membered ring that includes only two ring heteroatoms which are both N and W is null, then Z is not N.

In another embodiment the moiety V is $C_1$-$C_6$ alkyl, and e is zero or 1, wherein when e is zero, then V is null and, $R_1$ and $R_2$ are directly bonded to the same or different ring atoms. $R_1$ is H, OH, —$NH_2$, —COOH, $C_1$-$C_6$ alkyl, amidino, $C_1$-$C_6$ alkyl-substituted amidino, dihydroimidazole, Pro-amide, Pro, Gly, Ala, Val, Leu, Ile, Lys, Arg, Orn, Ser, Thr, CN, $CONH_2$, CONR'R", NHCOR', or $SO_2$NR'R", wherein R' and R" are each independently H, or $C_1$-$C_8$ alkyl, or R' and R" are combined to form a 4- to 8-membered ring which ring is optionally substituted singly or doubly with substituents independently chosen from $C_1$-$C_6$ alkyl, —OH, —Cl, —F, —$NH_2$, —$NO_2$, —CN, and —COOH, amidino; and $R_2$ is H, amidino, singly or doubly $C_1$-$C_6$ alkyl-substituted amidino, —CN, —$CONH_2$, —CONR'R", —NHCOR', —$SO_2$NR'R", or —COOH.

In one embodiment, formula I is subject to two provisos: (i) when the Y and Z-containing ring moiety is a six or seven membered ring and when one of Y and Z is C and e is zero, then $R_1$ is not OH, and $R_1$ and $R_2$ are not both H; and (ii) when the Y and Z-containing ring moiety is a six membered ring, both Y and Z are N and W is null, then —(V)$_e$$R_1$$R_2$ is attached to a ring atom other than Z; and if e is zero, then $R_1$ and $R_2$ are not both —H.

In certain embodiments the synthetic peptide amides of the invention have the formula:

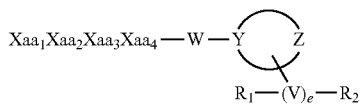

wherein $Xaa_1$ is chosen from (A)(A')D-Phe, (α-Me)D-Phe, D-Tyr, D-Tic, and (E)D-Ala, wherein A and A' are each phenyl ring substituents independently chosen from —H, —F, —Cl, —$NO_2$, —$CH_3$, —$CF_3$, —CN, —$CONH_2$, and wherein E is selected from the group consisting of cyclopentyl, pyridyl, thienyl and thiazolyl. $Xaa_2$ is chosen from (A)(A')D-Phe, (α-Me)D-Phe, D-1Nal, D-2Nal, D-Tyr, (E)D-Ala and D-Trp. $Xaa_3$ is chosen from D-Nle, D-Phe, cyclopentyl-D-Ala, D-Leu, (α-Me)D-Leu, D-Hle, D-Val, and D-Met. $Xaa_4$ is chosen from (B)$_2$D-Arg, (B)$_2$D-nArg, (B)$_2$D-Har, ζ-(B)D-Hlys, D-Dap, ε-(B)D-Lys, ε-(B)$_2$-D-Lys, D-Amf, amidino-D-Amf, γ-(B)$_2$D-Dbu, δ-(B)$_2$α-(B')D-Orn, D-2-amino-3(4-piperidyl)propionic acid, D-2-amino-3(2-aminopyrrolidyl) propionic acid, D-α-amino-β-amidinopropionic acid, (R)-α-amino-4-piperidineacetic acid, cis-α,4-diaminocyclohexane acetic acid, trans-α,4-diaminocyclohexaneacetic acid, cis-α-amino-4-methylaminocyclohexane acetic acid, trans-α-amino-4-methylamino-cyclohexane acetic acid, α-amino-1-amidino-4-piperidineacetic acid, cis-α-amino-4-guanidinocyclohexane acetic acid, and trans-α-amino-4-guanidinocyclohexane acetic acid, wherein each (B) is independently selected from the group consisting of H and $C_1$-$C_4$ alkyl, and (B') is H or (α-Me). The moiety W is chosen from one of the following three options: (i) null; (ii) —N—($CH_2$)$_b$ with b equal to zero, 1 2, 3, 4, 5, or 6; and (iii) —N—($CH_2$)$_c$—O— with c equal to 2 or 3 provided Y is a carbon atom.

The Y- and Z-containing ring moiety,

is an optionally substituted 6-8 membered saturated heterocyclic ring moiety, wherein no ring atom other than Y and Z is a heteroatom, Y and Z are separated by at least two carbon ring atoms, Y is C or N, and Z is S, O or N.

The moiety V is $C_1$-$C_6$ alkyl, and e is zero or 1, wherein when e is zero, then V is null and, $R_1$ and $R_2$ are directly bonded to the same or different ring atoms; $R_1$ is H, OH, —$NH_2$, —COOH, $C_1$-$C_6$ alkyl, amidino, $C_1$-$C_6$ alkyl-substituted amidino, dihydroimidazole, D-Pro, Gly, D-Ala, D-Val, D-Leu, D-Ile, D-Lys, D-Arg, D-Orn, D-Ser, D-Thr, —CN, —$CONH_2$, —CONR'R", —NHCOR', or —$SO_2$NR'R", wherein R' and R" are each independently —H, or $C_1$-$C_8$ alkyl, or R' and R" are combined to form a 4- to 8-membered ring which ring is optionally substituted singly or doubly with substituents independently chosen from $C_1$-$C_6$ alkyl, —OH, —Cl, —F, —$NH_2$, —$NO_2$, —CN, and —COOH, amidino; and $R_2$ is —H, amidino, $C_1$-$C_6$ alkyl-substituted amidino, —CN, —$CONH_2$, —CONR'R", —NHCOR', —$SO_2$NR'R", or —COOH.

In certain embodiments one of the following three provisos apply: when e is zero, then $R_1$ and $R_2$ are not both H; when W is —N—$(CH_2)_c$—O—, then Y is C and c is 2 or 3; or (iii) if Z is N, then Y is N, W is null, the Y and Z-containing ring moiety is a non aromatic six membered ring, and —$V_e(R_1)(R_2)$ is attached to Z, and —$V_e(R_1)(R_2)$ is chosen from amidino, $C_1$-$C_6$ alkyl-substituted amidino, dihydroimidazole, —$CH_2COOH$, and —$CH_2C(O)NH_2$.

In certain embodiments the synthetic peptide amides of the invention are dimers that include two synthetic peptide amide components joined by a linking moiety, L.

In one aspect the synthetic peptide amides have the formula:

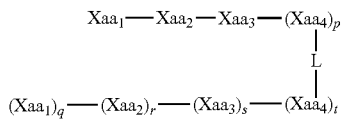

In the above formula, each $Xaa_1$ is independently chosen from (A)(A')D-Phe, (α-Me)D-Phe, D-Tyr, D-Tic, and (E)D-Ala, wherein (A) and (A') are each phenyl ring substituents independently chosen from —H, —F, —Cl, —$NO_2$, —$CH_3$, —$CF_3$, —CN, —$CONH_2$, and wherein (E) is chosen from thienyl, cyclopentyl, pyridyl, and thiazolyl. Each $Xaa_2$ is independently chosen from (A)(A')D-Phe, (α-Me)D-Phe, D-1Nal, D-2Nal, D-Tyr, and D-Trp; and r is zero or 1. Each $Xaa_3$ is independently chosen from D-Nle, D-Phe, cyclopentyl-D-Ala, D-Leu, (α-Me)D-Leu, D-Hle, D-Val, and D-Met; and s is zero or 1. Each $Xaa_4$ is independently chosen from $(B)_2$D-Arg, $(B)_2$D-nArg, $(B)_2$D-Har, ε-$(B)$D-Hlys, D-2,3-diaminopropionic acid, ε-$(B)$D-Lys, ε-$(B)_2$-D-Lys, D-Amf, amidino-D-Amf, $(B)_2$D-Dbu, δ-$(B)_2$α-(B')D-Orn, D-2-amino-3(4-piperidyl)propionic acid, D-2-amino-3(2-aminopyrrolidyl)propionic acid, D-α-amino-β-amidinopropionic acid, wherein each (B) is independently selected from the group consisting of H and $C_1$-$C_4$ alkyl, and (B') is H or (α-Me); and p, q, r, s and t are each independently zero or 1, provided that at least one of q, r, s and t are 1. In certain aspects of the invention, at least one of s and t is 1.

The moiety L is a linker chosen from ε-D-Lys, ε-Lys, δ-D-Orn, δ-Orn, γ-aminobutyric acid, 8-aminooctanoic acid, 11-aminoundecanoic acid, 8-amino-3,6-dioxaoctanoic acid, amidino-4-amino-4-carboxylic piperidine and (D-Lys-Gly lactam)$_2$.

Stereoisomers, mixtures of stereoisomers, prodrugs, pharmaceutically acceptable salts, hydrates, solvates, acid salt hydrates, N-oxides and isomorphic crystalline forms of these synthetic peptide amides are also contemplated within the scope of the present invention.

In another aspect, the present invention provides a synthetic peptide amide having the formula:

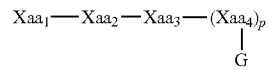

wherein G is

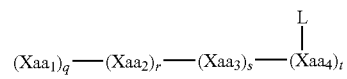

and wherein q is zero or 1; r is zero or 1; s is zero or 1; p and t are each independently zero or 1, provided that at least one of q, r, s and t are 1; and L is a linker chosen from ε-D-Lys, ε-Lys, δ-D-Orn, δ-Orn, γ-aminobutyric acid, 8-amino-octanoic acid, 11-amino-undecanoic acid, 8-amino-3,6-dioxaoctanoic acid, 4-amino-4-carboxylic piperidine and (D-Lys-Gly lactam)$_2$.

In another embodiment, the invention provides synthetic peptide amides having the formula:

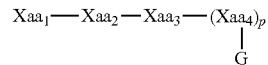

wherein G is

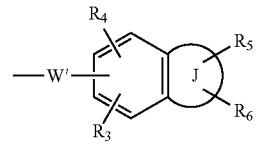

wherein J is a 5-, 6-, or 7-membered heterocyclic ring moiety having 1, 2, or 3 heteroatoms in the ring wherein $R_3$ and $R_4$ are each independently chosen from $C_1$-$C_3$ alkyl, halo, —OH, —$CF_3$, —$NH_2$, —COOH and amidino; and $R_5$ and $R_6$ are each independently chosen from $C_1$-$C_3$ alkyl, oxo, halo, —OH, —$CF_3$, —$NH_2$, —COOH and amidino.

In another embodiment, the invention provides a synthetic peptide amide having the formula:

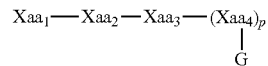

wherein G is

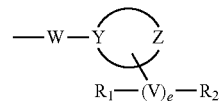

and W is null, Y is N and Z is C. In one aspect, the Y and Z-containing ring moiety is a six-membered saturated ring comprising a single ring heteroatom.

In another embodiment, G is

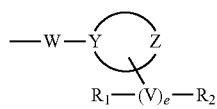

and Y and Z are both N and are the only ring heteroatoms in the Y and Z-containing ring moiety. In another embodiment, e is zero, and substituents $R_1$ and $R_2$ taken together with zero, one or two ring atoms of the Y and Z-containing ring moiety comprise a monocyclic or bicyclic 4-9 membered heterocyclic ring moiety. In one aspect of this embodiment, $R_1$ and $R_2$ taken together with one ring atom of the Y and Z-containing ring moiety comprise a 4- to 8-membered heterocyclic ring moiety which with the Y and Z-containing ring moiety forms a spiro structure and W is null.

In one embodiment, G is

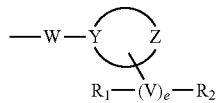

and e is zero and $R_1$ and $R_2$ are bonded directly to the same ring atom. Alternatively, in another embodiment, $R_1$ is H, OH, —$NH_2$, —COOH, —$CH_2COOH$, $C_1$-$C_3$ alkyl, amidino, $C_1$-$C_3$ alkyl-substituted amidino, dihydroimidazole, D-Pro, D-Pro amide, or $CONH_2$ and wherein $R_2$ is H, —COOH, or $C_1$-$C_3$ alkyl.

In another embodiment, G is chosen from:

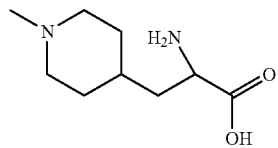

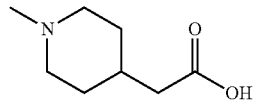

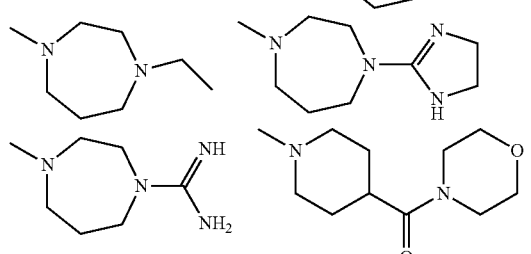

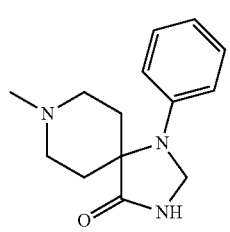

-continued

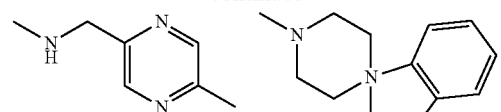

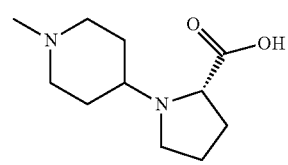

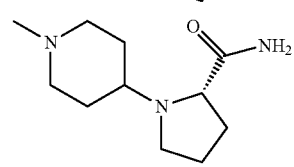

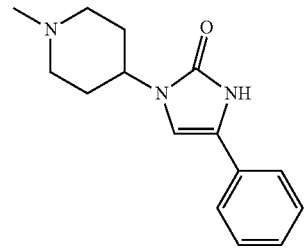

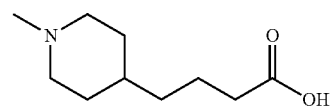

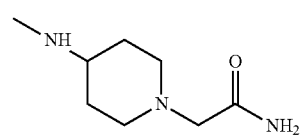

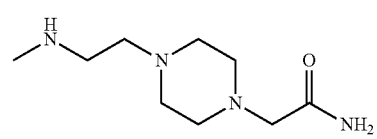

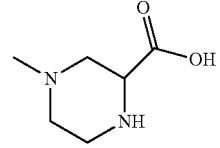

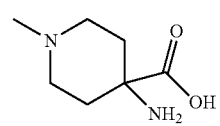

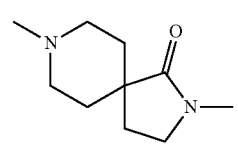

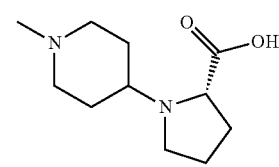

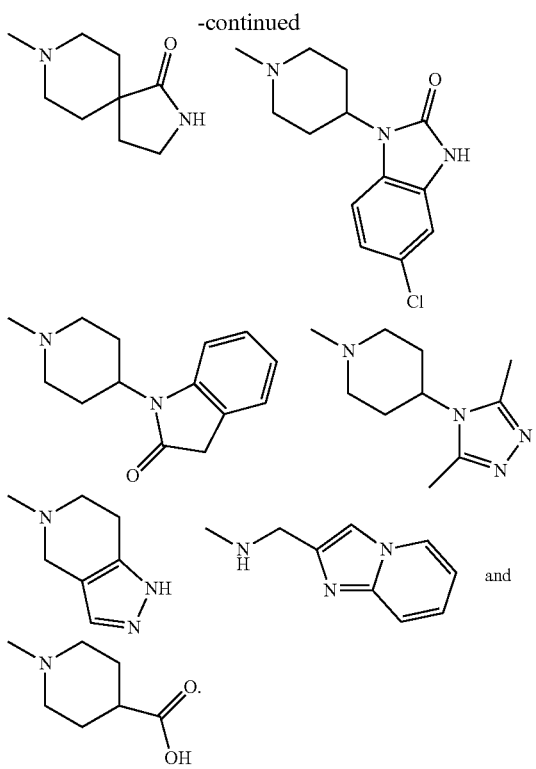

In one embodiment, the invention provides a synthetic peptide amide wherein each Xaa$_2$ is D-Phe, each Xaa$_3$ is D-Nle, and each Xaa$_4$ is D-Arg. In another embodiment, each Xaa$_1$ is D-Ala(2-thienyl).

In one embodiment, G is

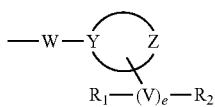

and the dipeptide Xaa$_3$-Xaa$_4$ is chosen from D-Leu-D-Orn and D-Nle-D-Arg. In another embodiment Xaa$_1$-Xaa$_2$ is D-Phe-D-Phe. In another embodiment Xaa$_1$ is D-(4-F)Phe, and Xaa$_2$ is D-(4-Cl)Phe.

In another embodiment each Xaa$_1$ is D-Phe or D-Ala(2-thienyl) and each Xaa$_2$ is D-(4-Cl)Phe. In another embodiment, each Xaa$_3$ is D-Leu or D-Nle.

In another embodiment G is

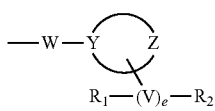

and Xaa$_1$ is chosen from D-Phe, D-(4-F)Phe, D-(2-F)Phe, cyclopentyl D-Ala, 2-thienyl D-Ala, Xaa$_2$ is chosen from D-(4-F)Phe, D-(4-Cl)Phe, D-1Nal, D-2Nal, and D-Trp, and Xaa$_3$-Xaa$_4$ is chosen from D-Nle-D-Arg and D-Leu-D-Orn.

In one embodiment Xaa$_1$ can be (A)(A')D-Phe, and in one aspect, each Xaa$_1$ is D-Phe. In another embodiment each Xaa$_2$ is D-Phe. In another embodiment, each Xaa$_3$ is chosen from D-Nle, and D-Leu. In another embodiment each Xaa$_4$ is chosen from δ(B)$_2$D-Orn and D-Arg. In one aspect, each Xaa$_4$ is δ(B)$_2$D-Orn and each (B) chosen from —H, methyl and isopropyl. In another aspect each Xaa$_4$ is (B)$_2$D-Orn, wherein one (B) is H, and the other (B) selected from the group consisting of methyl and isopropyl. In another aspect each Xaa$_4$ is D-Orn.

In another embodiment each Xaa$_4$ is chosen from (B)$_2$D-Arg, and δ-(B)$_2$D-Orn. In one aspect each Xaa$_4$ is chosen from D-Arg, (Et)$_2$D-Arg, and δ-(B)D-Orn, and (B) is H, Me, iPr, or Bu.

In another embodiment G is

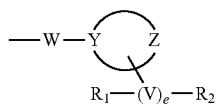

and W is null.

In another embodiment G is

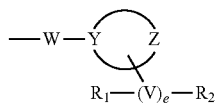

and W is —N—(CH$_2$)$_b$ with b equal to 0, 1, 2, 3, or 4. In one aspect b is zero and Y is a carbon atom. In another aspect b is 1 or 2 and Y is a nitrogen atom. In another embodiment W is —N—(CH$_2$)$_c$—O—. In one aspect c is 1 or 2. In another aspect the Y and Z-containing ring moiety is a four or five membered ring and Y is a nitrogen atom. In another embodiment the Y and Z-containing ring moiety is a four or five membered ring and Y is a carbon atom.

In another embodiment the Y and Z-containing ring moiety is a six or seven membered ring, Y is a nitrogen atom and Z is a carbon atom. In another alternative, the Y and Z-containing ring moiety is a six membered ring. In one aspect the Y and Z-containing ring moiety is a seven membered ring. In still another aspect the Y and Z-containing ring moiety is a six or seven membered ring and both Y and Z are nitrogen atoms.

In another embodiment e is zero and R$_1$ and R$_2$ are bonded directly to the same ring atom. In one aspect e is zero, R$_2$ is —H and R$_1$ is bonded directly to a carbon ring atom adjacent to Z. In another aspect R$_1$ is H, amidino, C$_1$-C$_3$ alkyl substituted amidino, C$_1$-C$_3$ alkyl, dihydroimidazole, D-Pro, D-Pro amide, or —CONH$_2$ and wherein e is zero and R$_2$ is —H. In another aspect R$_1$ is —H, amidino, or methyl amidino. In one aspect the Y and Z-containing ring moiety is a five membered ring, e is zero and R$_1$ is —COOH.

In another embodiment G is

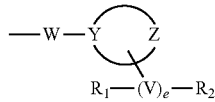

and Xaa$_1$ is D-Phe, Xaa$_2$ is D-Phe, Xaa$_3$ is D-Leu, Xaa$_4$ is δ-(B)$_2$D-Orn, wherein (B) is —H, methyl, or isopropyl; further wherein W is null, the Y and Z-containing ring moiety is a six or seven membered ring, Y is a nitrogen atom, e is zero, R$_1$ is —NH$_2$, amidino, C$_1$-C$_3$ alkyl, C$_1$-C$_3$ alkyl-substituted amidino, dihydroimidazole, D-Pro, or D-Pro amide, and R$_2$ is H or —COOH.

In certain embodiments of the synthetic peptide amides of the invention, there are two independent occurrences of the residues $Xaa_1$, $Xaa_2$, $Xaa_3$ and $Xaa_4$. For instance, in embodiments having the formula:

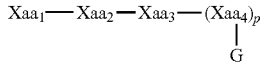

wherein G is:

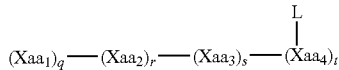

and one or more of q, r, and s is 1 or both p and t is 1, then there are two occurrences of $Xaa_1$, $Xaa_2$, $Xaa_3$ and $Xaa_4$ respectively. In such embodiments, each instance of each of the residues $Xaa_1$, $Xaa_2$, $Xaa_3$ and $Xaa_4$ can be identical. Thus, both instances of $Xaa_1$ can be identical, such as for instance, D-phenylalanine. Likewise, each instance of $Xaa_2$, $Xaa_3$, and $Xaa_4$ can be identical. So for example, each $Xaa_2$ can be D-(4-F)phenylalanine, each $Xaa_3$ can be D-leucine and each $Xaa_2$ can be D-arginine.

Alternatively, and in other embodiments, each instance of one or more of the pairs of residues $Xaa_1$, $Xaa_2$, $Xaa_3$ or $Xaa_4$ can be different. For example, one instance of $Xaa_1$ can be D-phenylalanine, while the second instance of $Xaa_1$ in the same molecule can be a different $Xaa_1$ residue, such as D-(4-F)phenylalanine. Similarly, one instance of $Xaa_2$ can be D-phenylalanine, while the second instance of $Xaa_2$ in the same molecule can be D-Ala(2-thienyl). Likewise, one instance of $Xaa_3$ can be D-norleucine, while the second instance of $Xaa_3$ in the same molecule can be D-leucine. In the same manner, one instance of $Xaa_4$ can be D-ornithine, while the second instance of $Xaa_4$ in the same molecule can be D-arginine, and so on.

In one embodiment, the invention provides a synthetic peptide amide wherein $Xaa_1$ is D-Ala(2-thienyl). In another embodiment $Xaa_1$ is D-(4-F)phenylalanine and $Xaa_2$ is D-(4-Cl)phenylalanine. In another embodiment each $Xaa_1$ is D-phenylalanine or D-Ala(2-thienyl) and each $Xaa_2$ is D-(4-Cl)phenylalanine. In another embodiment $Xaa_1$-$Xaa_2$ is D-phenylalanine-D-phenylalanine.

In one embodiment each $Xaa_3$ is chosen from D-norleucine and D-leucine. In another embodiment each $Xaa_2$ is D-phenylalanine, each $Xaa_3$ is D-norleucine, and each $Xaa_4$ is D-arginine. In another embodiment each $Xaa_3$ can be D-leucine or D-norleucine.

In another embodiment $Xaa_4$ is chosen from $\delta(B)_2$D-ornithine and D-arginine. Alternatively, each $Xaa_4$ is $\delta(B)_2$D-ornithine and each (B) is chosen from —H, methyl and isopropyl. In still another embodiment, each $Xaa_4$ is $(B)_2$D-ornithine, wherein one (B) is —H, and the other (B) chosen from methyl and isopropyl. In one aspect, each $Xaa_4$ is $(B)_2$D-arginine, or $\delta$-$(B)_2$D-ornithine. In another embodiment each $Xaa_4$ can be a residue chosen from D-arginine, $(Et)_2$D-arginine, and $\delta$-(B)D-ornithine, and wherein (B) is —H, methyl, isopropyl, or butyl. In one embodiment the dipeptide $Xaa_3$-$Xaa_4$ is chosen from D-leucine-D-ornithine and D-norleucine-D-arginine.

In one particular embodiment the synthetic peptide amide of the invention has the formula

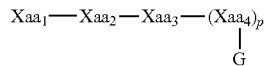

wherein G is:

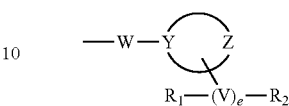

and b is zero and Y is a carbon atom. In another embodiment, b is 1 or 2 and Y is a nitrogen atom. In a particular aspect of the invention, b is 2.

In another embodiment G is

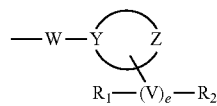

and the Y- and Z-containing moiety is [ω(4-aminopiperidine-4-carboxylic acid)]-OH.

In one particular embodiment $Xaa_1$ is chosen from D-Phe, D-(4-F)Phe, D-(2-F)Phe, cyclopentyl D-Ala, 2-thienyl D-Ala, $Xaa_2$ is chosen from D-(4-F)Phe, D-(4-Cl)Phe, D-1Nal, D-2Nal, and D-Trp, and $Xaa_3$-$Xaa_4$ is chosen from D-Nle-D-Arg and D-Leu-D-Orn.

In another embodiment W is an N-alkoxyl linker of the formula —N—$(CH_2)_c$—O—. In one aspect, c is 1 or 2. In an alternative embodiment W is null and $Xaa_1Xaa_2Xaa_3Xaa_4$ is directly bonded to Y. In a second alternative embodiment, W is an N-alkyl linker of the formula —NH—$(CH_2)_2$—.

In another particular embodiment, the Y and Z-containing ring moiety is a four or five membered ring and Y is a nitrogen atom. Alternatively, the Y- and Z-containing ring moiety can be a four or five membered ring wherein Y is a carbon atom. In a different embodiment, the Y and Z-containing ring moiety is a six or seven-membered ring, Y is a nitrogen atom and Z is a carbon atom. In one aspect of this embodiment, the Y and Z-containing ring moiety is a six membered ring. Alternatively, the Y and Z-containing ring moiety can be a seven membered ring. In one aspect of this embodiment, the Y and Z-containing ring moiety is a six or seven membered ring and both Y and Z are nitrogen atoms. Alternatively, the Y- and Z-containing ring moiety can be a six membered ring. In still another alternative, the Y and Z-containing ring moiety is a seven membered ring.

In another particular embodiment the Y- and Z-containing ring moiety is a six or seven membered ring, Y is a carbon atom, and Z is a nitrogen atom. In one aspect of this embodiment, the Y- and Z-containing ring moiety is a six membered ring. Alternatively, the Y- and Z-containing ring moiety can be a seven- or an eight-membered ring. In one aspect Y is a nitrogen atom and Z is a carbon atom. In one alternative embodiment Y and Z are each a nitrogen atom.

In another particular embodiment the Y- and Z-containing ring moiety is an optionally substituted 4 to 8-membered heterocyclic ring moiety wherein Y is a carbon or a nitrogen atom and Z is carbon, nitrogen, oxygen, sulfur, sulfoxide, or sulfonyl; and the 4 to 8-membered heterocyclic ring moiety is optionally singly or doubly substituted with substituents independently chosen from $C_1$-$C_6$ alkyl, —$C_1$-$C_6$ alkoxy, oxo, —OH, —Cl, —F, —NH$_2$, —NO$_2$, —CN, —COOH, and amidino. In one aspect when the Y- and Z-containing ring moiety is a six, seven or eight-membered ring, then Y and Z are separated by at least two ring atoms. In another aspect, when the Y- and Z-containing ring moiety is non-aromatic and Z is a carbon or a nitrogen atom, then such ring moiety includes at least one sulfur or oxygen ring heteroatom. In a particular aspect, when the Y- and Z-containing ring moiety is aromatic, then Y is a carbon atom.

In one embodiment of the synthetic peptide amide of the invention, R$_1$ is —H, —OH, —NH$_2$, —COOH, C$_1$-C$_3$ alkyl, amidino, C$_1$-C$_3$ alkyl-substituted amidino, dihydroimidazole, D-Pro, D-Pro amide, or —CONH$_2$. In another particular embodiment R$_2$ is —H, —COOH, or C$_1$-C$_3$ alkyl. In one aspect, only one of R$_1$ and R$_2$ is a hydrogen atom. In a particular embodiment R$_1$ is —H, D-Pro, D-Pro amide, or —NH$_2$ and R$_2$ is H or —COOH. In one aspect of this embodiment, R$_1$ is —NH$_2$ and $_2$ is —COOH.

In one embodiment, the operator, e is zero and R$_1$ and R$_2$ are bonded directly to the same ring atom. In a particular embodiment, e is zero, R$_2$ is —H and R$_1$ is bonded directly to a carbon ring atom adjacent to Z. In another particular embodiment, R$_1$ is —H, amidino, C$_1$-C$_3$ alkyl substituted amidino, C$_1$-C$_3$ alkyl, dihydroimidazole, D-Pro, D-Pro amide, or —CONH$_2$ and e is zero and R$_2$ is —H.

In one embodiment of the synthetic peptide amide of the invention, Xaa$_1$ is D-Phe, Xaa$_2$ is D-Phe, Xaa$_3$ is D-Leu, Xaa$_4$ is δ-(B)$_2$D-Orn, wherein (B) is —H, methyl, or isopropyl; such that wherein W is null, the Y and Z-containing ring moiety is a six or seven membered ring, Y is a nitrogen atom, e is zero, R$_1$ is —NH$_2$, amidino, C$_1$-C$_3$ alkyl, C$_1$-C$_3$ alkyl-substituted amidino, dihydroimidazole, D-Pro, or D-Pro amide, and R$_2$ is H or —COOH.

In one particular embodiment G represents one of the following:

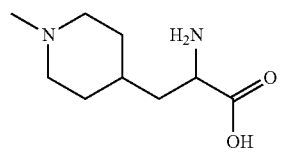

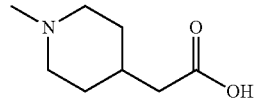

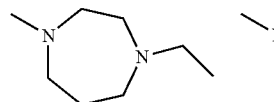

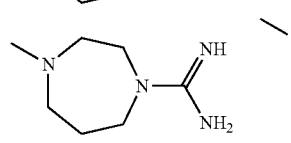

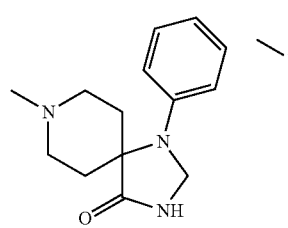

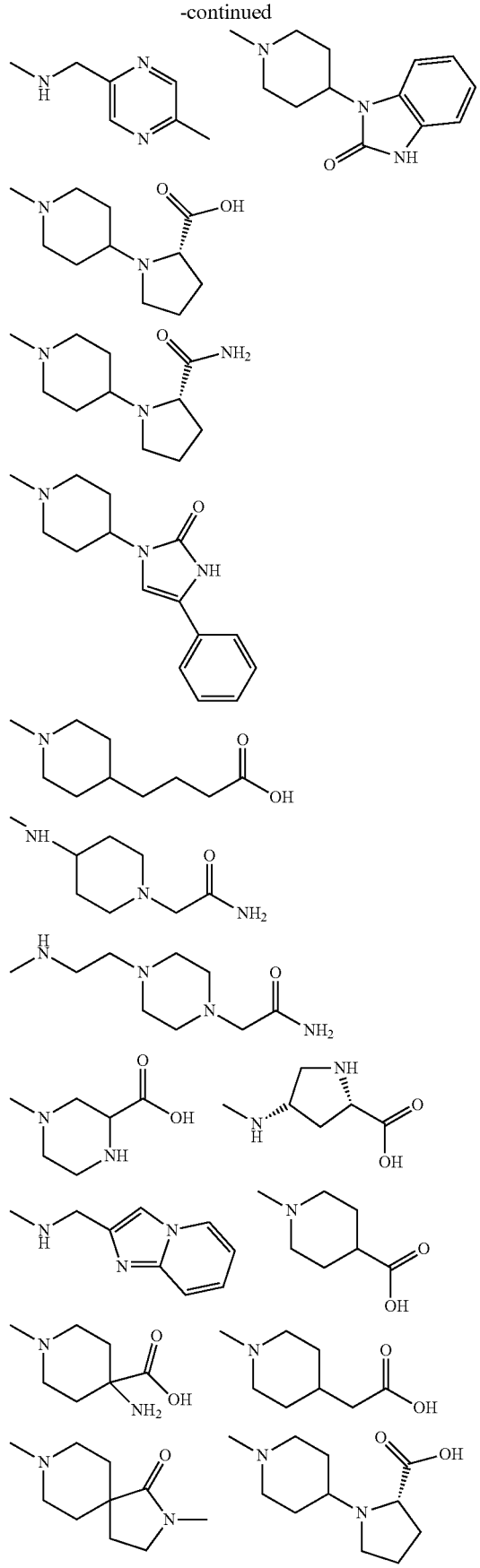

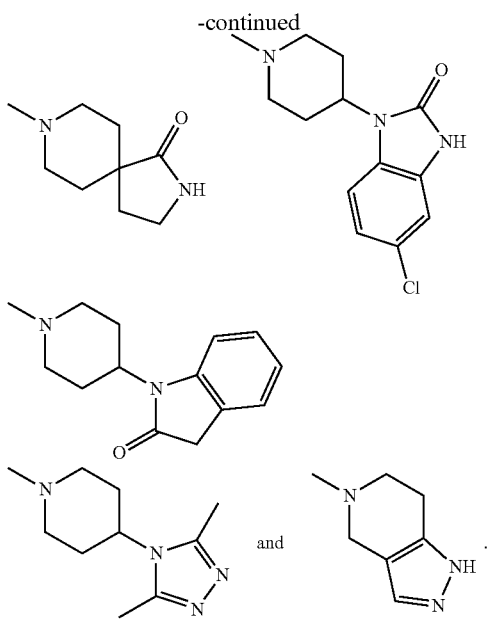

A variety of assays may be employed to test whether the synthetic peptide amides of the invention exhibit high affinity and selectivity for the kappa opioid receptor, long duration of in vivo bioactivity, and lack of CNS side effects. Receptor assays are well known in the art and kappa opioid receptors from several species have been cloned, as have mu and delta opioid receptors. Kappa opioid receptors as well as mu and delta opioid receptors are classical, seven transmembrane-spanning, G protein-coupled receptors. Although these cloned receptors readily allow a particular candidate compound, e.g., a peptide or peptide derivative, to be screened, natural sources of mammalian opioid receptors are also useful for screening, as is well known in the art (Dooley C T et al. Selective ligands for the mu, delta, and kappa opioid receptors identified from a single mixture based tetrapeptide positional scanning combinatorial library. *J. Biol. Chem.* 273: 18848-56, 1998). Thus, screening against both kappa and mu opioid receptors, whether of recombinant or natural origin, may be carried out in order to determine the selectivity of the synthetic peptide amides of the invention for the kappa over the mu opioid receptor.

In a particular embodiment, the synthetic peptide amides of the invention are selective kappa opioid receptor agonists. The potency of the synthetic peptide amides of the invention as agonists for a particular receptor can be measured as a concentration at which half maximal effect is achieved expressed as an $EC_{50}$ value. Potency of the synthetic peptide amides of the invention as kappa opioid agonists, expressed as the percent of maximal observable effect, can be determined by a variety of methods well known in the art. See for example, Endoh T et al., 1999, Potent Antinociceptive Effects of TRK-820, a Novel κ-Opioid Receptor Agonist, *Life Sci.* 65 (16) 1685-94; and Kumar V et al., Synthesis and Evaluation of Novel Peripherally Restricted κ-Opioid Receptor Agonists, 2005 *Bioorg Med Chem Letts* 15: 1091-1095.

Examples of such assay techniques for determination of $EC_{50}$ values are provided below. Many standard assay methods for characterization of opioid ligands are well known to those of skill in the art. See, for example, Waldhoer et al., (2004) Ann. Rev. Biochem. 73:953-990, and Satoh & Minami (1995) Pharmac. Ther. 68(3):343-364 and references cited therein.

In certain particular embodiments, the synthetic peptide amides of the invention are kappa opioid receptor agonists with an $EC_{50}$ of less than about 500 nM. In other embodiments, the synthetic peptide amides have an $EC_{50}$ of less than about 100 nM as kappa opioid receptor agonists. In still other embodiments, the synthetic peptide amides have an $EC_{50}$ of less than about 10 nM as kappa opioid receptor agonists. In particular embodiments the synthetic peptide amides of the invention have an $EC_{50}$ of less than about 1.0 nM, less than about 0.1 nM, or less than about 0.1 nM, or even less than about 0.01 nM as kappa opioid receptor agonists. The compounds of the foregoing embodiment can have an $EC_{50}$ that is at least 10 times greater for a mu and a delta opioid receptor than for a kappa opioid receptor, preferably at least 100 times greater, and most preferably at least 1000 times greater, such as for instance, an $EC_{50}$ of less than about 1 nM for a kappa opioid receptor, and $EC_{50}$ values of greater than about 1000 nM for a mu opioid receptor and a delta opioid receptor).

In particular embodiments, the synthetic peptide amides of the invention are highly selective for kappa over mu opioid receptors. In certain embodiments the synthetic peptide amides of the invention have $EC_{50}$ values for the mu opioid receptor that are at least about a hundred times higher than the corresponding $EC_{50}$ values for the kappa opioid receptor. In particular embodiments, the synthetic peptide amides of the invention have $EC_{50}$ values for the mu opioid receptor that are at least about a thousand times higher than the corresponding $EC_{50}$ values for the kappa opioid receptor. Alternatively, the selectivity of the synthetic peptide amides of the invention can be expressed as a higher $EC_{50}$ for a mu opioid receptor than for a kappa opioid receptor. Thus, in particular embodiments, the synthetic peptide amides of the invention have $EC_{50}$ values of greater than about 10 uM for the mu opioid receptor and $EC_{50}$ values of less than about 10 nM, and in other embodiments less than about 1.0 nM, or even less than about 0.01 nM for the kappa opioid receptor. In another embodiment, the particular synthetic peptide amide can have an $EC_{50}$ of less than about 1 nM for a kappa opioid receptor and an $EC_{50}$ of greater than about 1000 nM for a mu opioid receptor, or for a delta opioid receptor.

Another property of the synthetic peptide amides of the invention is their characteristic property of low inhibition of the cytochrome $P_{450}$ isozymes. The cytochrome $P_{450}$ isozymes constitute a large superfamily of haem-thiolate proteins responsible for metabolic oxidative inactivation of many therapeutics and other bioactive compounds. Usually, they act as terminal oxidases in multicomponent electron transfer chains, also referred to as cytochrome $P_{450}$-containing monooxygenase systems.

Over fifty different cytochrome $P_{450}$ isozymes have been identified and have been classified into families grouped by genetic relatedness as assessed by nucleic acid sequence homology. Most abundant among the cytochrome $P_{450}$ isozymes in human cells are the 1A2 and 3A4 isozymes, although isozymes 2B6, 2C9, 2C19, 2D6, and 2E1 also contribute significantly to oxidative inactivation of administered therapeutics. While inhibition of the cytochrome $P_{450}$ isozymes may be useful in prolonging the time after in vivo administration during which an effective concentration of the synthetic peptide amides of the invention is maintained, it also prolongs the persistence of any co-administered therapeutic compound that is subject to oxidation by cytochrome $P_{450}$. This increase in persistence may cause the co-administered therapeutic to persist beyond the period that is optimal for therapy, or may cause the in vivo concentration to exceed the desired levels or safely tolerated levels. Such increases in persistence and/or increases in concentration are difficult to accurately quantify and are preferably avoided. Therapeutics that show little or no inhibition of the activity of the cytochrome $P_{450}$ isozymes do not have this potential problem and can be more safely co-administered with other therapeutics without risk of affecting the rate of inactivation of the co-administered therapeutic compound by the cytochrome $P_{450}$ isozymes.

Particular embodiments of the synthetic peptide amides of the invention show low inhibition of the cytochrome $P_{450}$ isozymes at therapeutic concentrations of the synthetic peptide amides, while others show essentially no inhibition of the cytochrome $P_{450}$ isozymes at therapeutic concentrations. In some embodiments, the synthetic peptide amides at a concentration of 10 uM show less than about 50% inhibition of cytochrome $P_{450}$ isozymes CYP1A2, CYP2C9, CYP2C19 or CYP2D6. In particular embodiments, the synthetic peptide amides at a concentration of 10 uM show less than about 20% inhibition of any of these cytochrome $P_{450}$ isozymes. In very particular embodiments, the synthetic peptide amides at a concentration of 10 uM show less than about 10% inhibition of any of these cytochrome $P_{450}$ isozymes.

In another embodiment, the synthetic peptide amides of the invention at an effective concentration exhibit no more than about 50% inhibition of any of $P_{450}$ CYP1A2, CYP2C9, CYP2C19 or CYP 2D6 by the synthetic peptide amide at a concentration of 10 uM after 60 minutes incubation with human liver microsomes.

The synthetic peptide amides of the invention when administered to a mammal or a human patient at a therapeutically effective concentration exhibit low or essentially no penetration across the blood-brain barrier. Kappa opioid receptors (hereinafter interchangeably referred to as kappa receptors) are distributed in peripheral tissues, including the skin and somatic tissues, as well as the viscera in humans and other mammals. Kappa receptors are also found in the brain. Activation of the kappa receptors in peripheral tissues causes suppression of pain and inflammatory responses, while activation of the kappa receptors in the brain causes sedative effects and may also lead to severe dysphoria and hallucinations. In certain embodiments, the synthetic peptide amides of the invention when administered at therapeutically effective concentrations exhibit little or essentially no penetration across the blood-brain barrier and therefore minimize or even completely obviate the sedative, hallucinogenic effects of many other kappa agonists that show some penetration across the blood-brain barrier.

One useful measure of the extent to which the synthetic peptide amides of the invention cross the blood-brain barrier is the ratio of the peak plasma concentration to the concentration in brain tissue. In particular embodiments, the synthetic peptide amides of the invention when administered at a dose of about 3 mg/kg, exhibit at least about a five fold lower concentration of the synthetic peptide amide in brain than in plasma at the time when peak plasma concentration is reached.

Another useful measure of the extent to which the synthetic peptide amides of the invention cross the blood-brain barrier is the ratio of the dose required to achieve a sedative effect and the dose required to achieve an analgesic effect. The analgesic and sedative effects of kappa receptor stimulation by kappa receptor agonists can be measured by standard assays well known to those of skill in the art.

In particular embodiments, the synthetic peptide amides of the invention have an $ED_{50}$ for a sedative effect that is at least about ten times the $ED_{50}$ for an analgesic effect. In particular embodiments, the synthetic peptide amides of the invention have an $ED_{50}$ for a sedative effect that is at least about thirty times the $ED_{50}$ for an analgesic effect. In still other embodiments, the synthetic peptide amides of the invention have an $ED_{50}$ for a sedative effect that is at least about fifty times the $ED_{50}$ for an analgesic effect.

In another embodiment, the synthetic peptide amides of the invention have an $ED_{50}$ for a sedative effect in a locomotion-reduction assay in a mouse at least about ten times the $ED_{50}$ of the synthetic peptide amide for an analgesic effect in a writhing assay in a mouse.

Another useful predictor of the extent to which the synthetic peptide amides of the invention would be expected to cross the blood-brain barrier is provided by the membrane permeability values of the synthetic peptide amides into a human cell or other mammalian cell when delivered at a therapeutically relevant concentration. In certain embodiments, the synthetic peptide amides of the invention at therapeutically relevant concentrations exhibit low or essentially no ability to penetrate a monolayer of suitably cultured human or other mammalian cells. This permeability parameter can be expressed as an apparent permeability, $P_{app}$, representing the permeability of the particular cell monolayer to a compound of interest. Any suitably culturable mammalian cell monolayer can be used to determine its permeability for a particular compound of interest, although certain cell lines are frequently used for this purpose. For instance, the Caco-2 cell line is a human colon adenocarcinoma that can be used as a monolayer culture test system for determination of membrane permeability towards compounds of the invention. In certain embodiments, the synthetic peptide amides of the invention have a $P_{app}$ of less than about $10^{-6}$ cm/sec. In certain other embodiments, the synthetic peptide amides of the invention have a $P_{app}$ of less than about $10^{-7}$ cm/sec.

In one embodiment, the synthetic peptide amides of the invention at a dose of about 3 mg/kg in rat reaches a peak plasma concentration of the synthetic peptide amide and exhibits at least about a five fold lower concentration in brain than such peak plasma concentration.

In another embodiment, the synthetic peptide amides of the invention have at least about 50% of maximum efficacy at about 3 hours post administration of a dose of about 3 mg/kg of the synthetic peptide amide in a rat.

In one embodiment the synthetic peptide amide of the invention exhibits a long lasting duration of action in a mammal, such as a human. In one aspect, the synthetic peptide amide has a duration of action that is at least about 50% of maximum efficacy at 3 hrs post administration of 0.1 mg/kg of the synthetic peptide amide. In another aspect the synthetic peptide amide has a duration of action that is at least about 75% of maximum efficacy at 3 hrs post administration of 0.1 mg/kg of the synthetic peptide amide. In a particular aspect the synthetic peptide amide has a duration of action that is at least about 90% of maximum efficacy at 3 hrs post administration of 0.1 mg/kg of the synthetic peptide amide. In a specific aspect, the synthetic peptide amide has a duration of action that is at least about 95% of maximum efficacy at 3 hrs post administration of 0.1 mg/kg of the synthetic peptide amide.

In another embodiment, the invention provides a pharmaceutical composition that includes a synthetic peptide amide according to any of the above embodiments and a pharmaceutically acceptable excipient or carrier. The invention provides methods, compositions, or dosage forms that employ and/or contain synthetic peptide amides of the invention that are selective for the kappa opioid receptor. In particular embodiments, the synthetic peptide amides of the invention exhibit a strong affinity for the kappa opioid receptor and have a high potency as kappa opioid receptor agonists.

A pro-drug of a compound such as the synthetic peptide amides of the invention include pharmaceutically acceptable derivatives which upon administration can convert through metabolism or other process to a biologically active form of the compound. Pro-drugs are particularly desirable where the pro-drug has more favorable properties than does the active compound with respect to bioavailability, stability or suitability for a particular formulation.

As used herein, a kappa opioid receptor-associated disease, condition or disorder is any disease, condition or disorder that is preventable or treatable by activation of a kappa opioid receptor. In one aspect, the synthetic peptide amides of the invention are kappa opioid receptor agonists that activate the kappa opioid receptor. In some embodiments, a particular dose and route of administration of the synthetic peptide amide of the invention can be chosen by a clinician to completely prevent or cure the disease, condition or disorder. In other embodiments a particular dose and route of administration of the synthetic peptide amide of the invention chosen by the clinician ameliorates or reduce one or more symptoms of the disease, condition or disorder.

As used herein, "effective amount" or "sufficient amount" of the synthetic peptide amide of the invention refers to an amount of the compound as described herein that may be therapeutically effective to inhibit, prevent, or treat a symptom of a particular disease, disorder, condition, or side effect. As used herein, a "reduced dose" of a mu opioid agonist analgesic compound refers to a dose which when used in combination with a kappa opioid agonist, such as a synthetic peptide amide of the invention, is lower than would be ordinarily provided to a particular patient, for the purpose of reducing one or more side effects of the compound. The dose reduction can be chosen such that the decrease in the analgesic or other therapeutic effect of the compound is an acceptable compromise in view of the reduced side effect(s), where the decrease in analgesic or other therapeutic effects of the mu opioid agonist analgesic are wholly or at least partially offset by the analgesic or other therapeutic effect of the synthetic peptide amide of the invention. Co-administration of a mu opioid agonist analgesic compound with a synthetic peptide amide of the invention which acts as a kappa opioid agonist also permits incorporation of a reduced dose of the synthetic peptide amide and/or the mu opioid agonist analgesic compound to achieve the same therapeutic effect as a higher dose of the synthetic peptide amide or the mu opioid agonist analgesic compound if administered alone.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit-to-risk ratio that is reasonable for the medical condition being treated.

As used herein, "dosage unit" refers to a physically discrete unit suited as unitary dosages for a particular individual or condition to be treated. Each unit may contain a predetermined quantity of active synthetic peptide amide compound(s) calculated to produce the desired therapeutic effect(s), optionally in association with a pharmaceutical carrier. The specification for the dosage unit forms may be dictated by (a) the unique characteristics of the active compound or compounds, and the particular therapeutic effect to be achieved, and (b) the limitations inherent in the art of compounding such active compound or compounds. The dosage unit is often expressed as weight of compound per unit body weight, for instance, in milligrams of compound per kilogram of body weight of the subject or patient (mg/kg). Alternatively, the dosage can be expressed as the amount of the compound per unit body weight per unit time, (mg/kg/day) in a particular dosage regimen. In a further alternative, the dosage can be expressed as the amount of compound per unit body surface area ($mg/m^2$) or per unit body surface area per unit time ($mg/m^2/day$). For topical formulations, the dosage unit time can be expressed in a manner that is conventional for that formulation, e.g., a one-half inch ribbon of ointment applied to the eye, where the concentration of compound in the formulation is expressed as a percentage of the formulation.

As used herein, "pharmaceutically acceptable salts" refer to derivatives of compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids and the like. The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Thus, a pharmaceutically acceptable salt of a synthetic peptide amide can be formed from any such peptide amide having either acidic, basic or both functional groups. For example, a peptide amide having a carboxylic acid group, may in the presence of a pharmaceutically suitable base, form a carboxylate anion paired with a cation such as a sodium or potassium cation. Similarly, a peptide amide having an amine functional group may, in the presence of a pharmaceutically suitable acid such as HCl, form a salt.

One example of a pharmaceutically acceptable solvate of a synthetic peptide amide is a combination of a peptide amide with solvent molecules which yields a complex of such solvent molecules in association with the peptide amide. Particularly suitable hydrates of compounds are such hydrates which either have comparable activity or hydrates which are converted back to the active compound following administration. A pharmaceutically acceptable N-oxide of a synthetic peptide amide which contains an amine is such a compound wherein the nitrogen atom of the amine is bonded to an oxygen atom.

A pharmaceutically acceptable crystalline, isomorphic crystalline or amorphous form of a synthetic peptide amide of the invention can be any crystalline or non-crystalline form of a pharmaceutically acceptable acidic, basic, zwitterionic, salt, hydrate or any other suitably stable, physiologically compatible form of the synthetic peptide amide according to the invention.

The synthetic peptide amides of the invention can be incorporated into pharmaceutical compositions. The compositions can include an effective amount of the synthetic peptide amide in a pharmaceutically acceptable diluent, excipient or carrier. Conventional excipients, carriers and/or diluents for use in pharmaceutical compositions are generally inert and make up the bulk of the preparation.

In a particular embodiment, the synthetic peptide amide is a kappa opioid receptor agonist. In another embodiment, the synthetic peptide amide is a selective kappa opioid receptor agonist. The target site can be a kappa receptor in the patient or subject in need of such treatment or preventative. Certain synthetic peptide amide kappa opioid receptor agonists of the invention are peripherally acting and show little or no CNS effects at therapeutically effective doses.

The pharmaceutical excipient or carrier can be any compatible, non-toxic substance suitable as a vehicle for delivery the synthetic peptide amide of the invention. Suitable excipients or carriers include, but are not limited to, sterile water (preferably pyrogen-free), saline, phosphate-buffered saline (PBS), water/ethanol, water/glycerol, water/sorbitol, water/polyethylene glycol, propylene glycol, cetylstearyl alcohol, carboxymethylcellulose, corn starch, lactose, glucose, microcrystalline cellulose, magnesium stearate, polyvinylpyrrolidone (PVP), citric acid, tartaric acid, oils, fatty substances, waxes or suitable mixtures of any of the foregoing.

The pharmaceutical preparation according to the invention can be formulated as a liquid, semisolid or solid dosage form. For example the pharmaceutical preparation can be in the form of a solution for injection, drops, syrup, spray, suspension, tablet, patch, capsule, dressing, suppository, ointment, cream, lotion, gel, emulsion, aerosol or in a particulate form, such as pellets or granules, optionally pressed into tablets or lozenges, packaged in capsules or suspended in a liquid. The tablets can contain binders, lubricants, diluents, coloring agents, flavoring agents, wetting agents and may be enteric-coated to survive the acid environment of the stomach and dissolve in the more alkaline conditions of the intestinal lumen. Alternatively, the tablets can be sugar-coated or film coated with a water-soluble film. Pharmaceutically acceptable adjuvants, buffering agents, dispersing agents, and the like, may also be incorporated into the pharmaceutical compositions.

Binders include for instance, starch, mucilage, gelatin and sucrose. Lubricants include talc, lycopodium, magnesium and calcium stearate/stearic acid. Diluents include lactose, sucrose, mannitol, salt, starch and kaolin. Wetting agents include propylene glycol and sorbitan monostearate.

As used herein, local application or administration refers to administration of a pharmaceutical preparation according to the invention to the site, such as an inflamed joint, that exhibits the painful and/or inflamed condition. Such local application includes intrajoint, such as intra-articular application, via injection, application via catheter or delivery as part of a biocompatible device. Thus, local application refers to application to a discrete internal area of the body, such as, for example, a joint, soft tissue area (such as muscle, tendon, ligaments, intraocular or other fleshy internal areas), or other internal area of the body. In particular, as used herein, local application refers to applications that provide substantially no systemic delivery and/or systemic administration of the active agents in the present compositions. Also, as used herein, local application is intended to refer to applications to discrete areas of the body, that is, other than the various large body cavities (such as, for example, the peritoneal and/or pleural cavities).

As used herein, topical application refers to application to the surface of the body, such as to the skin, eyes, mucosa and lips, which can be in or on any part of the body, including but not limited to the epidermis, any other dermis, or any other body tissue. Topical administration or application means the direct contact of the pharmaceutical preparation according to the invention with tissue, such as skin or membrane, particularly the cornea, or oral, vaginal or anorectal mucosa. Thus, for purposes herein topical application refers to application to the tissue of an accessible body surface, such as, for example, the skin (the outer integument or covering) and the mucosa (the mucus-producing, secreting and/or containing surfaces). In particular, topical application refers to applications that provide little or substantially no systemic delivery of the active compounds in the present compositions. Exemplary mucosal surfaces include the mucosal surfaces of the eyes, mouth (such as the lips, tongue, gums, cheeks, sublingual and roof of the mouth), larynx, esophagus, bronchus, trachea, nasal passages, vagina and rectum/anus.

For oral administration, an active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. To facilitate drug stability and absorption, peptides of the invention can be released from a capsule after passing through the harsh proteolytic environment of the stomach. Methods for enhancing peptide stability and absorption after oral administration are well known in the art (e.g., Mahato R I. Emerging trends in oral delivery of peptide and protein drugs. *Critical Reviews in Therapeutic Drug Carrier Systems.* 20:153-214, 2003).

Dosage forms such as lozenges, chewable tablets and chewing gum permit more rapid therapeutic action compared to per-oral dosage forms of the synthetic peptide amide compounds of the invention having significant buccal absorption. Chewing gum formulations are solid, single dose preparations with a base consisting mainly of gum, that are intended to be chewed but not swallowed, and contain one or more compounds of the invention which are released by chewing and are intended to be used for local treatment of pain and inflammation of the mouth or systemic delivery after absorption through the buccal mucosa. See for example, U.S. Pat. No. 6,322,828 to Athanikar and Gubler entitled: Process for manufacturing a pharmaceutical chewing gum.

For nasal administration, the peripherally selective kappa opioid receptor agonists can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, Drug Delivery to the Respiratory Tract, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159.

The pharmaceutical compositions of the invention can be prepared in a formulation suitable for systemic delivery, such as for instance by intravenous, subcutaneous, intramuscular, intraperitoneal, intranasal, transdermal, intravaginal, intrarectal, intrapulmonary or oral delivery. Alternatively, the pharmaceutical compositions of the invention can be suitably formulated for local delivery, such as, for instance, for topical, or iontophoretic delivery, or for transdermal delivery by a patch coated, diffused or impregnated with the formulation, and local application to the joints, such as by intra-articular injection.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous, and thereby formulated for delivery by injection, infusion, or using implantable pumps. For intravenous, subcutaneous, and intramuscular administration, useful formulations of the invention include microcapsule preparations with controlled release properties (R. Pwar et al. Protein and peptide parenteral controlled delivery. *Expert Opin Biol Ther.* 4(8):1203-12, 2004) or encapsulation in liposomes, with an exemplary form being polyethylene coated liposomes, which are known in the art to have an extended circulation time in the vasculature (e.g. Koppal, T. "Drug delivery technologies are right on target", *Drug Discov. Dev.* 6, 49-50, 2003).

For ophthalmic administration, the present invention provides a method of treating glaucoma or ophthalmic pain and inflammation, comprising administering to an eye of a patient in need thereof a therapeutically effective amount of a synthetic peptide amide of the invention. The synthetic peptide amide can be administered topically with an eye-compatible pharmaceutical carrier or non-systemically using a contact lens or intraocular implant that can optionally contain polymers that provide sustained release of the synthetic peptide amide. Such eye-compatible pharmaceutical carriers can include adjuvants, antimicrobial preservatives, surfactants, and viscolyzers etc. It is known in the art that high concentrations of many compounds are irritant to the eye and low concentrations are less irritant; thus the formulation is often designed to include the lowest effective concentrations of active compound, preservative, surfactant, and/or viscolyzer, said viscolyzer preferably having a high surface tension to reduce irritation of the eye while increasing the retention of ophthalmic solutions at the eye surface. Such controlled release of the synthetic peptide amides of the invention can last 6 months to a year for implants, or for shorter periods (3-14 days) for contact lenses. Such implants can be osmotic pumps, biodegradable matrices, or intraocular sustained release devices. Such topical compositions can include a buffered saline solution with or without liposomes.

Aqueous polymeric solutions, aqueous suspensions, ointments, and gels can be used for topical formulations of the synthetic peptide amides of the invention for ocular applications. The aqueous formulations may also contain liposomes for creating a reservoir of the synthetic peptide amide. Certain of these topical formulations are gels which enhance precorneal retention without the inconvenience and impairment of vision associated with ointments. The eye-compatible pharmaceutical carrier can also include a biodegradable synthetic polymer. Biodegradable microsphere compositions approved for human use include the polylactides: poly(lactic acid), poly(glycolic acid), and poly(lactic-coglycolic) acid. Additional biodegradable formulations include, but are not limited to: poly(anhydride-co-imide), poly(lactic-glycolic acid), polyethyl-2-cyanoacrylate, polycaprolactone, polyhydroxybutyrate valerate, polyorthoester, and polyethylene-oxide/polybutylene teraphthalate. Intraocular implantation or injection of sustained release compositions that include a synthetic peptide amide of the invention can provide long-term control (ranging from months to years) of intraocular pressure, and thereby avoiding or reducing the need for topical preparations. Useful methods for formulating and dispensing ophthalmic medications are disclosed in U.S. Pat. No. 7,122,579 to Schwartz et al, and in U.S. Pat. No. 7,105,512 to Morizono et al. Methods for formulating ophthalmic medications in contact lenses are disclosed by Gulsen and Chauhan, Ophthalmic drug delivery through contact lenses. *Investigative Ophthalmology and Visual Science*, (2004) 45:2342-2347.

Preparations for transdermal delivery are incorporated into a device suitable for said delivery, said device utilizing, e.g., iontophoresis (Kalia Y N et al. Iontophoretic Drug Delivery. *Adv Drug Deliv Rev.* 56:619-58, 2004) or a dermis penetrating surface (Prausnitz M R. Microneedles for Transdermal Drug Delivery. *Adv Drug Deliv Rev.* 56:581-7, 2004), such as are known in the art to be useful for improving the transdermal delivery of drugs. An electrotransport device and methods of operation thereof are disclosed in U.S. Pat. No. 6,718,201. Methods for the use of iontophoresis to promote transdermal delivery of peptides are disclosed in U.S. Pat. No. 6,313,092 and U.S. Pat. No. 6,743,432.

As used herein the terms "electrotransport", "iontophoresis", and "iontophoretic" refer to the delivery through a body surface (e.g., skin or mucosa) of one or more pharmaceutically active compounds by means of an applied electromotive force to an agent containing reservoir. The compound may be delivered by electromigration, electroporation, electroosmosis or any combination thereof. Electroosmosis has also been referred to as electrohydrokinesis, electro convection, and electrically induced osmosis. In general, electroosmosis of a compound into a tissue results from the migration of solvent in which the compound is contained, as a result of the application of electromotive force to the therapeutic species reservoir, such as for instance, solvent flow induced by electromigration of other ionic species. During the electrotransport process, certain modifications or alterations of the skin may occur such as the formation of transiently existing pores in the skin, also referred to as "electroporation." Any electrically assisted transport of species enhanced by modifications or alterations to the body surface (e.g., formation of pores in the skin) are also included in the term "electrotransport" as used herein. Thus, as used herein, applied to the compounds of the instant invention, the terms "electrotransport", "iontophoresis" and "iontophoretic" refer to (1) the delivery of charged agents by electromigration, (2) the delivery of uncharged agents by the process of electroosmosis, (3) the delivery of charged or uncharged agents by electroporation, (4) the delivery of charged agents by the combined processes of electromigration and electroosmosis, and/or (5) the delivery of a mixture of charged and uncharged agents by the combined processes of electromigration and electroosmosis. Electrotransport devices generally employ two electrodes, both of which are positioned in close electrical contact with some portion of the skin of the body. One electrode, called the active or donor electrode, is the electrode from which the therapeutic agent is delivered into the body. The other electrode, called the counter or return electrode, serves to close the electrical circuit through the body. In conjunction with the patient's skin, the circuit is completed by connection of the electrodes to a source of electrical energy, e.g., a battery, and usually to circuitry capable of controlling current passing through the device.

Depending upon the electrical charge of the compound to be delivered transdermally, either the anode or cathode may be the active or donor electrode. Thus, if the compound to be transported is positively charged, e.g., the compound exemplified in Example 1 herein, then the positive electrode (the anode) will be the active electrode and the negative electrode (the cathode) will serve as the counter electrode, completing the circuit. However, if the compound to be delivered is negatively charged, then the cathodic electrode will be the active electrode and the anodic electrode will be the counter electrode. Electrotransport devices additionally require a reservoir or source of the therapeutic agent that is to be delivered into the body. Such drug reservoirs are connected to the anode or the cathode of the electrotransport device to provide a fixed or renewable source of one or more desired species or agents. Each electrode assembly is comprised of an electrically conductive electrode in ion-transmitting relation with an ionically conductive liquid reservoir which in use is placed in contact with the patient's skin. Gel reservoirs such as those described in Webster (U.S. Pat. No. 4,383,529) are one form of reservoir since hydrated gels are easier to handle and manufacture than liquid-filled containers. Water is one liquid solvent that can be used in such reservoirs, in part because the salts of the peptide compounds of the invention are water soluble and in part because water is non-irritating to the skin, thereby enabling prolonged contact between the hydrogel reservoir and the skin. For electrotransport, the synthetic peptides of the invention can be formulated with flux enhancers such as ionic surfactants or cosolvents other than water (See for example, U.S. Pat. No. 4,722,726 and European Patent Application 278,473, respectively). Alternatively the outer layer (i.e., the stratum corneum) of the skin can be mechanically disrupted prior to electrotransport delivery therethrough, for example as described in U.S. Pat. No. 5,250,023.

Peripherally synthetic peptide amides that are well suited for electrotransport can be selected by measuring their electrotransport flux through the body surface (e.g., the skin or mucosa), e.g., as compared to a standardized test peptide with known electrotransport flux characteristics, e.g. thyrotropin releasing hormone (R. Burnette et al. *J. Pharm. Sci.* (1986) 75:738) or vasopressin (Nair et al. *Pharmacol Res.* 48:175-82, 2003). Transdermal electrotransport flux can be determined using a number of in vivo or in vitro methods well known in the art. In vitro methods include clamping a piece of skin of an appropriate mammal (e.g., human cadaver skin) between the donor and receptor compartments of an electrotransport flux cell, with the stratum corneum side of the skin piece facing the donor compartment. A liquid solution or gel containing the drug to be delivered is placed in contact with the stratum corneum, and electric current is applied to electrodes, one electrode in each compartment. The transdermal flux is calculated by sampling the amount of drug in the receptor compartment. Two successful models used to optimize transdermal electrotransport drug delivery are the isolated pig skin flap model (Heit M C et al. Transdermal iontophoretic peptide delivery: in vitro and in vivo studies with luteinizing hormone releasing hormone. *J. Pharm. Sci.* 82:240-243, 1993), and the use of isolated hairless skin from hairless rodents or guinea pigs, for example. See Hadzija B W et al. Effect of freezing on iontophoretic transport through hairless rat skin. *J. Pharm. Pharmacol.* 44, 387-390, 1992.

Compounds of the invention for transdermal iontophoretic delivery can have one, or typically, two charged nitrogens, to facilitate their delivery.

Other useful transdermal delivery devices employ high velocity delivery under pressure to achieve skin penetration without the use of a needle. Transdermal delivery can be improved, as is known in the art, by the use of chemical enhancers, sometimes referred to in the art as "permeation enhancers", i.e., compounds that are administered along with the drug (or in some cases used to pretreat the skin, prior to drug administration) in order to increase the permeability of the stratum corneum, and thereby provide for enhanced penetration of the drug through the skin. Chemical penetration enhancers are compounds that are innocuous and serve merely to facilitate diffusion of the drug through the stratum corneum, whether by passive diffusion or an energy driven process such as electrotransport. See, for example, Meidan V M et al. Enhanced iontophoretic delivery of buspirone hydrochloride across human skin using chemical enhancers. *Int. J. Pharm.* 264:73-83, 2003.

Pharmaceutical dosage forms for rectal administration include rectal suppositories, capsules and tablets for systemic effect. Rectal suppositories as used herein mean solid bodies for insertion into the rectum which melt or soften at body temperature releasing one or more pharmacologically or therapeutically active ingredients. Pharmaceutically acceptable substances utilized in rectal suppositories include bases or vehicles and agents that raise the melting point of the suppositories. Examples of bases include cocoa butter (*theobroma* oil), glycerin-gelatin, carbowax, (polyoxyethylene glycol) and appropriate mixtures of mono-, di- and triglycerides of fatty acids. Combinations of the various bases can also be used. Agents that raise the melting point of suppositories include spermaceti and wax. Rectal suppositories may be prepared either by the compression method or by molding. Rectal suppositories typically weigh about 2 gm to about 3 gm. Tablets and capsules for rectal administration are manufactured using the same pharmaceutically acceptable substance(s) and by the same methods as for formulations for oral administration.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride for injection, Ringers solution for injection, isotonic dextrose for injection, sterile water for injection, dextrose and lactated Ringers solution for injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfite. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween 80). A sequestering or chelating agent of metal ions such as EDTA can also be incorporated. Pharmaceutical carriers also include ethyl alcohol, polyethylene glycol and propylene glycol for water miscible vehicles and the pH can be adjusted to a physiologically compatible pH by addition of sodium hydroxide, hydrochloric acid, citric acid or lactic acid.

The active ingredient may be administered all at once, or may be divided into a number of smaller doses to be administered at intervals of time, or as a controlled release formulation. The term "controlled release formulation" encompasses formulations that allow the continuous delivery of a synthetic peptide amide of the invention to a subject over a period of time, for example, several days to weeks. Such formulations may be administered subcutaneously or intramuscularly and allow for the continual steady state release of a predetermined amount of compound in the subject over time. The controlled release formulation of synthetic peptide amide may be, for example, a formulation of drug containing polymeric microcapsules, such as those described in U.S. Pat. Nos. 4,677,191 and 4,728,721, incorporated herein by reference. The concentration of the pharmaceutically active compound is adjusted so that administration provides an effective amount to produce a desired effect. The exact dose depends on the age, weight and condition of the patient or animal, as is known in the art. For any particular subject, specific dosage regimens can be adjusted over time according to the individual need and the professional judgment of the person administering or supervising the administration of the formulations. Thus, the concentration ranges set forth herein are exemplary only and are not intended to limit the scope or practice of the claimed invention.

The unit dose parenteral preparations include packaging in an ampoule or prepackaged in a syringe with, or without a needle for delivery. All preparations for parenteral administration are typically sterile, as is practiced in the art. Illustratively, intravenous infusion of a sterile aqueous buffered solution containing an active compound is an effective mode of administration. In another embodiment a sterile aqueous or oily solution or suspension containing the active material can be injected as necessary to produce the desired pharmacological effect.

The pharmaceutical compositions of the invention can be delivered or administered intravenously, transdermally, transmucosally, intranasally, subcutaneously, intramuscularly, orally or topically (such as for example to the eye). The compositions can be administered for prophylactic treatment of individuals suffering from, or at risk of a disease or a disorder. For therapeutic applications, a pharmaceutical composition is typically administered to a subject suffering from a disease or disorder, in an amount sufficient to inhibit, prevent, or ameliorate the disease or disorder. An amount adequate to accomplish this is defined as a "therapeutically effective dose."

The pharmaceutical compositions of the invention can be administered to a mammal for prophylactic or therapeutic purposes in any of the above-described formulations and delivery modes. The mammal can be any mammal, such as a domesticated or feral mammal, or even a wild mammal. The mammal can be any primate, ungulate, canine or feline. For instance, and without limitation, the mammal may be a pet or companion animal, such as a dog or a cat; a high-value mammal such as a thoroughbred horse or a show animal; a farm animal, such as a cow, a goat, a sheep or pig; or a primate such as an ape, gorilla, orangutan, lemur, monkey or chimpanzee. A suitable mammal for prophylaxis or treatment using the pharmaceutical compositions of the invention is a human.

The pharmaceutical compositions of the invention can be administered to a mammal having a disease or condition treatable by activation of the kappa opioid receptor. Alternatively, the pharmaceutical compositions can be administered as prophylactics to a mammal having a risk of contracting or developing a disease or condition preventable by activation of the kappa opioid receptor. Diseases or conditions that can be treated or prevented by administration of the pharmaceutical compositions of the invention include, without limitation, any condition that can be ameliorated by activation of the kappa opioid receptor, including such conditions as pain, inflammation, pruritis, hyponatremia, hypokalemia, congestive heart failure, liver cirrhosis, nephrotic syndrome, hypertension, edema, ileus, tussis and glaucoma.

In a particular embodiment, the pharmaceutical compositions of the invention can be co-administered with or can include one or more other therapeutic compounds or adjuvants, such as but not limited to other opioids, cannabinoids, antidepressants, anticonvulsants, neuroleptics, antihistamines, acetaminophen, corticosteroids, ion channel blocking agents, non-steroidal anti-inflammatory drugs (NSAIDs), and diuretics, many of which are synergistic in effect with the synthetic peptide amides of the invention.

Suitable opioids, include, without limitation, alfentanil, alphaprodine, anileridine, bremazocine, buprenorphine, butorphanol, codeine, conorphone, dextromoramide, dextropropoxyphene, dezocine, diamorphine, dihydrocodeine, dihydromorphine, diphenoxylate, dipipanone, doxpicomine, ethoheptazine, ethylketazocine, ethylmorphine, etorphine, fentanyl, hydrocodone, hydromorphone, ketobemidone, levomethadyl, levorphanol, lofentanil, loperamide, meperidine (pethidine), meptazinol, methadone, morphine, morphine-6-glucuronide, nalbuphine, nalorphine, nicomorphine, oxycodone, oxymorphone, pentazocine, phenazocine, phenoperidine, piritramide, propiram, propoxyphene, remifentanil, sufentanil, tilidate, tonazocine, and tramadol.

One embodiment of the invention is co-formulation and/or co-administration of an opioid with substantial agonist activity at the mu opioid receptor, such as morphine, fentanyl, hydromorphone, or oxycodone, together with a synthetic peptide amide of the invention, for the purpose of a mu opioid dose-sparing effect, where the dose of the mu opioid is reduced to minimize common mu opioid side effects, particularly in opioid-naïve patients. Such side effects include constipation, nausea, vomiting, sedation, respiratory depression, pruritis (itching), mental confusion, disorientation and cognitive impairment, urinary retention, biliary spasm, delirium, myoclonic jerks, and seizures. The selection of the reduced mu opioid dose requires expert clinical judgment, and depends on the unique characteristics of the various mu opioids, as well as patient characteristics such as pain intensity, patient age, coexisting disease, current drug regimen and potential drug interactions, prior treatment outcomes, and patient preference (McCaffery, M. and Pasero, C., *Pain Clinical Manual*, Second Edition, Mosby, 1999).

Cannabinoids suitable for administration with or incorporation into the pharmaceutical compositions of the invention, include any natural cannabinoid, such as for instance, tetrahydrocannabinol (THC), or a THC derivative, or a synthetic cannabinoid, such as, for instance, levonantradol, marinol, nabilone, rimonabant or savitex.

Suitable antidepressants that can be co-administered with or incorporated into the pharmaceutical compositions of the invention, include for example, tricyclic antidepressants such as imipramine, desipramine, trimipramine, protriptyline, norttriptyline, amitriptyline, doxepin, and clomipramine; atypical antidepressants such as amoxapine, maprotiline, trazodone, bupropion, and venlafaxine; serotonin-specific reuptake inhibitors such as fluoxetine, sertraline, paroxetine, citalopram and fluvoxamine; norepinephrine-specific reuptake inhibitors such as reboxetine; or dual-action antidepressants such as nefazodone and mirtazapine.

Suitable neuroleptics that can be co-administered with or incorporated into the pharmaceutical compositions of the invention, include any neuroleptic, for example, a compound with D2 dopamine receptor antagonist activity such as domperidone, metaclopramide, levosulpiride, sulpiride, thiethylperazine, ziprasidone, zotepine, clozapine, chlorpromazine, acetophenazine, carphenazine, chlorprothixene, fluphenazine, loxapine, mesoridazine, molindone, perphenazine, pimozide, piperacetazine, perchlorperazine, thioridazine, thiothixene, trifluoperazine, triflupromazine, pipamperone, amperozide, quietiapine, melperone, remoxipride, haloperidol, rispiridone, olanzepine, sertindole, ziprasidone, amisulpride, prochlorperazine, and thiothixene.

Anticonvulsants such as phenobarbital, phenytoin, primidone, carbamazepine, ethosuximide, lamotrigine, valproic acid, vigabatrin, felbamate, gabapentin, levetiracetam, oxcarbazepine, remacemide, tiagabine, and topiramate can also usefully be incorporated into the pharmaceutical compositions of the invention.

Muscle relaxants such as methocarbamol, orphenadrine, carisoprodol, meprobamate, chlorphenesin carbamate, diazepam, chlordiazepoxide and chlorzoxazone; anti-migraine agents such as sumitriptan, analeptics such as caffeine, methylphenidate, amphetamine and modafinil; antihistamines such as chlorpheniramine, cyproheptadine, promethazine and pyrilamine, as well as corticosteroids such as methylprednisolone, betamethasone, hydrocortisone, prednisolone, cortisone, dexamethasone, prednisone, alclometasone, clobetasol, clocortrolone, desonide, desoximetasone, diflorasone, fluocinolone, fluocinonide, flurandrenolide, fluticasone, floromethalone, halcinonide, halobetasol, loteprednol, mometasone, prednicarbate, and triamcinolone can also be incorporated into the pharmaceutical compositions of the invention.

Ion channel blocking agents such as, for instance, the sodium ion channel blocker, carbamazepine, as commonly used in the treatment of tinnitus, arrhythmia, ischemic stroke and epilepsy can be co-administered with or incorporated into the pharmaceutical compositions of the invention. Alternatively, or in addition, calcium ion channel blockers, such as ziconotide, can also be used, as can antagonists of the ion channel associated with the NMDA receptor, such as ketamine. There is evidence that at least some of these ion channel blockers can potentiate the analgesic effects of the kappa agonist and thereby reduce the dose required for affective pain relief. See for instance, Wang et al., 2000, *Pain* 84: 271-81.

Suitable NSAIDs, or other non-opioid compounds with anti-inflammatory and/or analgesic activity, that can be co-administered with or incorporated into the pharmaceutical compositions of the invention include, but are not limited to one or more of the following: aminoarylcarboxylic acid derivatives such as etofenamate, meclofenamic acid, mefanamic acid, niflumic acid; arylacetic acid derivatives such as acemetacin, amfenac, cinmetacin, clopirac, diclofenac, fenclofenac, fenclorac, fenclozic acid, fentiazac, glucametacin, isoxepac, lonazolac, metiazinic acid, naproxin, oxametacine, proglumetacin, sulindac, tiaramide and tolmetin; arylbutyric acid derivatives such as butibufen and fenbufen; arylcarboxylic acids such as clidanac, ketorolac and tinoridine. arylpropionic acid derivatives such as bucloxic acid, carprofen, fenoprofen, flunoxaprofen, ibuprofen, ibuproxam, oxaprozin, phenylalkanoic acid derivatives such as flurbiprofen, piketoprofen, pirprofen, pranoprofen, protizinic acid and tiaprofenic acid; pyranocarboxylic acids such as etodolac; pyrazoles such as mepirizole; pyrazolones such as clofezone, feprazone, mofebutazone, oxyphinbutazone, phenylbutazone, phenyl pyrazolidininones, suxibuzone and thiazolinobutazone; salicylic acid derivatives such as aspirin, bromosaligenin, diflusinal, fendosal, glycol salicylate, mesalamine, 1-naphthyl salicylate, magnesium salicylate, olsalazine and salicylamide, salsalate, and sulfasalazine; thiazinecarboxamides such as droxicam, isoxicam and piroxicam others such as ϵ-acetamidocaproic acid, acetaminophen, s-adenosylmethionine, 3-amino-4-hydroxybutyric acid, amixetrine, bendazac, bucolome, carbazones, cromolyn, difenpiramide, ditazol, hydroxychloroquine, indomethacin, ketoprofen and its active metabolite 6-methoxy-2-naphthylacetic acid; guaiazulene, heterocylic aminoalkyl esters of mycophenolic acid and derivatives, nabumetone, nimesulide, orgotein, oxaceprol, oxazole derivatives, paranyline, pifoxime, 2-substituted-4,6-di-tertiary-butyl-s-hydroxy-1,3-pyrimidines, proquazone and tenidap, and cox-2 (cyclooxygenase II) inhibitors, such as celecoxib or rofecoxib.

Suitable diuretics that can be co-administered with or incorporated into the pharmaceutical preparations of the invention, include, for example, inhibitors of carbonic anhydrase, such as acetazolamide, dichlorphenamide, and methazolamide; osmotic diuretics, such as glycerin, isosorbide, mannitol, and urea; inhibitors of $Na^+$—$K^+$-$2Cl^-$ symport (loop diuretics or high-ceiling diuretics), such as furosemide, bumetanide, ethacrynic acid, torsemide, axosemide, piretanide, and tripamide; inhibitors of $Na^+$—$Cl^-$ symport (thiazide and thiazidelike diuretics), such as bendroflumethiazide, chlorothiazide, hydrochlorothiazide, hydroflumethazide, methyclothiazide, polythiazide, trichlormethiazide, chlorthalidone, indapamide, metolazone, and quinethazone; and, in addition, inhibitors of renal epithelial $Na^+$ channels, such as amiloride and triamterene, antagonists of mineralocorticoid receptors (aldosterone antagonists), such as spironolactone, canrenone, potassium canrenoate, and eplerenone, which, together, are also classified as $K^+$-sparing diuretics. One embodiment is co-formulation and/or co-administration of a loop or thiazide diuretic together with a synthetic peptide amide of the invention for the purpose of a loop or thiazide diuretic dose-sparing effect, wherein the dose of the loop or thiazide diuretic is reduced to minimize undesired water retention, and prevent or reduce hyponatremia, particularly in the context of congestive heart failure, as well as other medical conditions where decreasing body fluid retention and normalizing sodium balance could be beneficial to a patient in need thereof. See R M Reynolds et al. Disorders of sodium balance Brit. Med. J. 2006; 332:702-705.

The kappa opioid receptor-associated hyponatremia can be any disease or condition where hyponatremia (low sodium condition) is present, e.g., in humans, when the sodium concentration in the plasma falls below 135 mmol/L, an abnormality that can occur in isolation or, more frequently, as a complication of other medical conditions, or as a consequence of using medications that can cause sodium depletion.

A further embodiment is co-formulation and/or co-administration of a potassium-sparing diuretic, e.g., a mineralocorticoid receptor antagonist, such as spironolactone or eplerenone, together with a synthetic peptide amide of the invention, for the purpose of enabling a reduced dose of said potassium-sparing diuretic, wherein the dose of said diuretic is reduced to minimize hyperkalemia or metabolic acidosis, e.g., in patients with hepatic cirrhosis.

In particular embodiments, the synthetic peptide amides of the invention exhibit a long lasting duration of action when administered in therapeutically relevant doses in vivo. For instance, in some embodiments, the synthetic peptide amides of the invention when administered to a mammal at a dose of 3 mg/kg of the synthetic peptide amide maintain at least about 50% of maximum efficacy in a kappa opioid receptor-dependent assay at 3 hours post administration. In certain other embodiments, the synthetic peptide amides of the invention when administered to a mammal at a dose of 0.1 mg/kg of the synthetic peptide amide maintain at least about 50% of maximum efficacy in a kappa opioid receptor-dependent assay at 3 hours post administration. The maximum efficacy is operationally defined as the highest level of efficacy determined for the particular kappa opioid receptor-dependent assay for all agonists tested.

In certain embodiments, the synthetic peptide amides of the invention when administered to a mammal at a dose of 0.1 mg/kg maintain at least about 75% of maximum efficacy at 3 hours post administration. In still other embodiments, the synthetic peptide amides of the invention when administered to a mammal at a dose of 0.1 mg/kg maintain at least about 90% of maximum efficacy at 3 hours post administration. In certain other embodiments, the synthetic peptide amides of the invention when administered to a mammal at a dose of 0.1 mg/kg maintain at least about 95% of maximum efficacy at three hours post administration.

The invention further provides a method of treating or preventing a kappa opioid receptor-associated disease or condition in a mammal, wherein the method includes administering to the mammal a composition containing an effective amount of a synthetic peptide amide of the invention. The mammal can be any mammal, such as a domesticated or feral mammal, or even a wild mammal. Alternatively, the mammal can be a primate, an ungulate, a canine or a feline. For instance, and without limitation, the mammal may be a pet or companion animal, such as a high-value mammal such as a thoroughbred or show animal; a farm animal, such as a cow, a goat, a sheep or pig; or a primate such as an ape or monkey. In one particular aspect, the mammal is a human.

The effective amount can be determined according to routine methods by one of ordinary skill in the art. For instance, an effective amount can be determined as a dosage unit sufficient to prevent or to treat a kappa receptor-associated disease or condition in the mammal. Alternatively, the effective amount may be determined as an amount sufficient to approximate the $EC_{50}$ concentration or an amount sufficient to approximate two or three times or up to about five or even about ten times the $EC_{50}$ concentration in a therapeutically relevant body fluid of the mammal, for instance, where the body fluid is in direct apposition to a target tissue, such as the synovial fluid of an inflamed joint in a patient suffering from rheumatoid arthritis.

In one embodiment the synthetic peptide amide of the invention is a pharmaceutical composition that includes an effective amount of the synthetic peptide amide of the invention and a pharmaceutically acceptable excipient or carrier. In one aspect, the pharmaceutical composition includes a synthetic peptide amide of the invention in an amount effective to treat or prevent a kappa opioid receptor-associated condition in a mammal, such as a human. In another aspect the kappa opioid receptor-associated condition is pain, inflammation, pruritis, edema, ileus, tussis or glaucoma.

In one embodiment the pharmaceutical composition of the invention further includes one or more of the following compounds: an opioid, a cannabinoid, an antidepressant, an anticonvulsant, a neuroleptic, a corticosteroid, an ion channel blocking agent or a non-steroidal anti-inflammatory drug (NSAID).

Pharmaceutical compositions that include a synthetic peptide amide of the invention and a pharmaceutically acceptable vehicle or carrier can be used to treat or prevent one or more of a variety of kappa opioid receptor-associated diseases, disorders or conditions.

The kappa opioid receptor-associated disease, disorders or condition preventable or treatable with the synthetic peptide amides of the invention can be any kappa opioid receptor-associated condition, including but not limited to acute or chronic pain, inflammation, pruritis, hyponatremia, edema, ileus, tussis and glaucoma. For instance, the kappa opioid receptor-associated pain can be neuropathic pain, somatic pain, visceral pain or cutaneous pain. Some diseases, disorders, or conditions are associated with more than one form of pain, e.g., postoperative pain can have any or all of neuropathic, somatic, visceral, and cutaneous pain components, depending upon the type and extent of surgical procedure employed.

The kappa opioid receptor-associated inflammation can be any inflammatory disease or condition including, but not limited to sinusitis, rheumatoid arthritis tenosynovitis, bursitis, tendonitis, lateral epicondylitis, adhesive capsulitis, osteomyelitis, osteoarthritic inflammation, inflammatory bowel disease (IBD), irritable bowel syndrome (IBS), ocular inflammation, otitic inflammation or autoimmune inflammation.

The kappa opioid receptor-associated pruritis can be any pruritic disease or condition such as, for instance, ocular pruritis, e.g., associated with conjunctivitis, otitic pruritis, pruritis associated with end-stage renal disease, where many patients are receiving kidney dialysis, and other forms of cholestasis, including primary biliary cirrhosis, intrahepatic cholestasis of pregnancy, chronic cholestatic liver disease, uremia, malignant cholestasis, jaundice, as well as dermatological conditions such as eczema (dermatitis), including atopic or contact dermatitis, psoriasis, polycythemia vera, lichen planus, lichen simplex chronicus, pediculosis (lice), thyrotoxicosis, tinea pedis, urticaria, scabies, vaginitis, anal pruritis associated with hemorrhoids and, as well as insect bite pruritis and drug-induced pruritis, such as mu opioid-induced pruritis.

The kappa opioid receptor-associated edema can be any edematous disease or condition such as, for instance, edema due to congestive heart disease or to a syndrome of inappropriate antidiuretic hormone (ADH) secretion.

The kappa opioid receptor-associated ileus can be any ileus disease or condition including, but not limited post-operative ileus or opioid-induced bowel dysfunction.

The kappa opioid receptor-associated neuropathic pain can be any neuropathic pain, such as, for instance, trigeminal neuralgia, diabetic pain, viral pain such as herpes zoster-associated pain, chemotherapy-induced pain, nerve-encroaching metastatic cancer pain, neuropathic pain associated with traumatic injury and surgical procedures, as well as variants of headache pain that are thought to have a neuropathic component, e.g., migraine.

Kappa opioid-associated pain also includes ocular pain, e.g., following photo-refractive keratectomy (PRK), ocular laceration, orbital floor fracture, chemical burns, corneal abrasion or irritation, or associated with conjunctivitis, corneal ulcers, scleritis, episcleritis, sclerokeratitis, herpes zoster ophthalmicus, interstitsal keratitis, acute iritis, keratoconjunctivitis sicca, orbital cellulites, orbital pseudotumor, pemphigus, trachoma, or uveitis.

Kappa opioid-associated pain also includes throat pain, particularly associated with inflammatory conditions, such as allergic rhinitis, acute bronchitis, the common cold, contact ulcers, herpes simplex viral lesions, infectious mononucleosis, influenza, laryngeal cancer, acute laryngitis, acute necrotizing ulcerative gingivitis, peritonsillar abscess, pharyngeal burns, pharyngitis, reflux laryngopharyngitis, acute sinusitis, and tonsillitis.

In addition, kappa opioid receptor-associated pain can be arthritic pain, kidney-stone, urinary tract stone, gallstone, and bile duct stone pain, uterine cramping, dysmenorrhea, endometriosis, mastitis, dyspepsia, post-surgical pain (such as, for instance, from appendectomy, open colorectal surgery, hernia repair, prostatectomy, colonic resection, gastrectomy, splenectomy, colectomy, colostomy, pelvic laparoscopy, tubal ligation, hysterectomy, vasectomy or cholecystecomy), post medical procedure pain (such as, for instance, after colonoscopy, cystoscopy, hysteroscopy or cervical or endometrial biopsy), otitic pain, breakthrough cancer pain, and pain associated with a GI disorder such as IBD or IBS or other inflammatory conditions, particularly of the viscera (e.g., gastroesophageal reflux disease, pancreatitis, acute polynephritis, ulcerative colitis, acute pyelonephritis, cholecystitis, cirrhosis, hepatic abscess, hepatitis, duodenal or gastric ulcer, esophagitis, gastritis, gastroenteritis, colitis, diverticulitis, intestinal obstruction, ovarian cyst, pelvic inflammatory disease, perforated ulcer, peritonitis, prostatitis, interstitial cystitis), or exposure to toxic agents, such as insect toxins, or drugs such as salicylates or NSAIDs.

The present invention provides a method of treating or preventing a kappa opioid receptor-associated disease or condition in a mammal, such as a human, wherein the method includes administering to the mammal a composition comprising an effective amount of a synthetic peptide amide of the invention. In another embodiment the kappa opioid receptor-associated condition is pain, inflammation (such as rheumatoid arthritic inflammation, osteoarthritic inflammation, IBD inflammation, IBS inflammation, ocular inflammation, otitic inflammation or autoimmune inflammation), pruritis (such as atopic dermatitis, kidney-dialysis-associated pruritis, ocular pruritis, otitic pruritis, insect bite pruritis, or opioid-induced pruritis), edema, ileus, tussis or glaucoma. In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystecomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

Kappa opioid receptor-associated pain includes hyperalgesia, which is believed to be caused by changes in the milieu of the peripheral sensory terminal occur secondary to local tissue damage. Tissue damage (e.g., abrasions, burns) and inflammation can produce significant increases in the excitability of polymodal nociceptors (C fibers) and high threshold mechanoreceptors (Handwerker et al. (1991) *Proceeding of the VIth World Congress on Pain*, Bond et al., eds., Elsevier Science Publishers BV, pp. 59-70; Schaible et al. (1993) *Pain* 55:5-54). This increased excitability and exaggerated responses of sensory afferents is believed to underlie hyperalgesia, where the pain response is the result of an exaggerated response to a stimulus. The importance of the hyperalgesic state in the post-injury pain state has been repeatedly demonstrated and appears to account for a major proportion of the post-injury/inflammatory pain state. See for example, Woold et al. (1993) *Anesthesia and Analgesia* 77:362-79; Dubner et al. (1994) In, *Textbook of Pain*, Melzack et al., eds., Churchill-Livingstone, London, pp. 225-242.

In another embodiment the kappa opioid receptor-associated condition is pain, inflammation (such as rheumatoid arthritic inflammation, osteoarthritic inflammation, IBD inflammation, IBS inflammation, ocular inflammation, otitic inflammation or autoimmune inflammation), pruritis (such as atopic dermatitis, kidney-dialysis-associated pruritis, ocular pruritis, otitic pruritis, insect bite pruritis, or opioid-induced pruritis), edema, ileus, tussis or glaucoma. In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystecomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

In another embodiment the kappa opioid receptor-associated condition is a kappa opioid receptor-associated condition preventable or treatable by sodium and potassium-sparing diuresis, also known as aquaresis. An example of such kappa opioid receptor-associated conditions preventable or treatable by administering a synthetic peptide amide of the invention includes edema. The edema may be due to any of a variety of diseases or conditions, such as congestive heart disease or syndrome of inappropriate ADH secretion.

In another embodiment the kappa opioid receptor-associated condition is hyponatremia or other edematous disease. The kappa opioid receptor-associated hyponatremia or edema can be any hyponatremic or edematous disease or condition such as, for instance, hyponatremia and edema associated with congestive heart failure or to a syndrome of inappropriate antidiuretic hormone (ADH) secretion, or hyponatremia that is associated with intensive diuretic therapy with thiazides and/or loop diuretics. The synthetic peptide amides of the invention exhibit a significant sodium-sparing and potassium-sparing aquaretic effect, which is beneficial in the treatment of edema-forming pathological conditions associated with hyponatremia and/or hypokalemia. Accordingly, the synthetic peptide amides of the invention also have utility in methods of treating or preventing hyponatremia-related conditions, examples of which are provided below. Hyponatremia-related conditions can be categorized according to volume status as hypervolemic, euvolemic, or hypovolemic.

Hypervolemic hyponatremia is usually caused by an increase in total body water level as may be observed in cases of congestive heart failure, nephrotic syndrome and hepatic cirrhosis.

Euvolemic hyponatremia is often found in the syndrome of inappropriate antidiuretic hormone (ADH) secretion and may also be associated with pneumonia, small-cell lung cancer, polydipsia, cases of head injury, and organic causes (e.g., use of certain drugs, such as haloperidol) or a psychogenic cause.

Hypovolemic hyponatremia is due to a relative decrease in total body sodium level and may be associated with diuretic use, cases of interstitial nephritis or excessive sweating.

These forms of hyponatremia can be further classified according to the concentration of sodium in the urine (i.e., whether the concentration is greater than or less than thirty millimoles per liter. See: R M Reynolds et al. Disorders of sodium balance, Brit. Med. J. 2006; 332:702-705.

The kappa opioid receptor-associated hyponatremia can be any disease or condition where hyponatremia (low sodium condition) is present, e.g., in humans, when the sodium concentration in the plasma falls below 135 mmol/L, an abnormality that can occur in isolation or, more frequently, as a complication of other medical conditions, or as a consequence of using medications that can cause sodium depletion.

In addition to these conditions, numerous other conditions are associated with hyponatremia including, without limitation: neoplastic causes of excess ADH secretion, including carcinomas of lung, duodenum, pancreas, ovary, bladder, and ureter, thymoma, mesothelioma, bronchial adenoma, carcinoid, gangliocytoma and Ewing's sarcoma; infections such as: pneumonia (bacterial or viral), abscesses (lung or brain), cavitation (aspergillosis), tuberculosis (lung or brain), meningitis (bacterial or viral), encephalitis and AIDS; vascular causes such as: cerebrovascular occlusions or hemorrhage and cavernous sinus thrombosis; neurologic causes such as: Guillan-Barre syndrome, multiple sclerosis, delirium tremens, amyotrophic lateral sclerosis, hydrocephalus, psychosis, peripheral neuropathy, head trauma (closed and penetrating), CNS tumors or infections and CNS insults affecting hypothalamic osmoreceptors; congenital malformations including: agenesis of corpus callosum, cleftlip/palate and other midline defects; metabolic causes such as: acute intermittent porphyria, asthma, pneurothorax and positive-pressure respiration; drugs such as: thiazide diuretics, acetaminophen, barbiturates, cholinergic agents, estrogen, oral hypoglycemic agents, vasopressin or desmopressin, high-dose oxytocin, chlorpropamide, vincristine, carbamezepine, nicotine, phenothiazines, cyclophosphamide, tricyclic antidepressants, monoamine oxidase inhibitors and serotonin reuptake inhibitors; administration of excess hypotonic fluids, e.g., during hospitalization, surgery, or during or after athletic events (i.e., exercise-associated hyponatremia), as well as use of low-sodium nutritional supplements in elderly individuals. See for example, Harrison's Principles of Internal Medicine, 16th Ed. (2005), p. 2102.

Other conditions associated with hyponatremia include renal failure, nephrotic syndrome (membranous nephropathy and minimal change disease), cachexia, malnutrition, rhabdomyolysis, surgical procedures, elective cardiac catheterization, blood loss, as well as hypercalcemia, hypokalemia, and hyperglycemia with consequent glycosuria leading to osmotic diuresis.

The invention also provides a method of treating or preventing a neuro-degenerative disease or condition in a mammal, such as a human, wherein the method includes administering to the mammal a composition that includes an effective amount of a synthetic peptide amide as described above. The neurodegenerative disease or condition can be any neurodegenerative disease or condition, such as for instance, ischemia, anoxia, stroke, brain injury, spinal cord injury or reperfusion injury. Alternatively, the neurodegenerative disease or condition can be a neurodegenerative disease of the eye. Particular neurodegenerative diseases of the eye treatable or preventable by the method of the invention include glaucoma, macular degeneration, retinal ischemic disease and diabetic neuropathy.

In certain embodiments the invention provides methods of prevention or treatment of certain neuronal diseases and conditions, such as diseases and conditions having a neurodegenerative component. Synthetic peptide amides of the invention can be administered in an amount effective to protect neuronal cells against the effects of pathology or injury that would lead to neurodegeneration and/or neuronal cell death of the untreated cells. For example, several diseases or conditions of the eye that have a neurodegenerative component can be prevented or treated by administration of an effective amount of the synthetic peptide amides of the invention. Such diseases and conditions of the eye include glaucoma, macular degeneration, retinal ischemic disease and diabetic neuropathy. Progression of these diseases and conditions is believed to involve neurodegeneration or neuronal cell death, for example by programmed cell death (apoptosis) in which the neuronal cells are committed to a pathway that without intervention would lead to cell death. It has been found that development or progression of these diseases and conditions can be prevented, or at least slowed, by treatment with kappa opioid receptor agonists. This improved outcome is believed to be due to neuroprotection by the kappa opioid receptor agonists. See for instance, Kaushik et al. "Neuroprotection in Glaucoma" (2003) *J. Postgraduate Medicine* vol. 49 (1): pp. 90-95.

In the case of glaucoma it is believed that prophylaxis and treatment by administration of kappa opioid receptor agonists is mediated by at least two distinct activities induced by activation of the kappa opioid receptor: neuroprotection and reduction of intraocular pressure (IOP). While not wishing to be bound by theory, it is believed that neuroprotection is due, at least in part, to induction of atrial natriuretic peptide (ANP) in the eye, leading to protection against oxidative damage and other insults.

Abnormally high intraocular pressure is also believed to be a factor leading to the development of glaucoma. Elevated intraocular pressure can also be prevented or treated by administration of kappa opioid receptor agonists by three separate activities triggered by activation of the receptor: reduction in secretion of aqueous humor, increased outflow of aqueous humor and aquaresis (sodium- and potassium-sparing diuresis, resulting in loss of water).

The invention also provides a method of treating or preventing a kappa-receptor-associated disease or condition of the eye of a mammal, such as high intraocular pressure (IOP). The method includes administering to the mammal a composition that includes an effective amount of a synthetic peptide amide as described above. In one aspect of the invention, the synthetic peptide amide is administered topically. In another aspect, the synthetic peptide amide is administered as an implant.

In other embodiments the invention provides methods of prevention or treatment of certain cardiovascular diseases and conditions having a cellular degenerative component. Synthetic peptide amides of the invention can be administered in an amount effective to protect myocardial cells against the effects of pathology or injury that would lead to degeneration and/or cell death of the untreated cells. For example, several cardiovascular diseases or conditions can be prevented or treated by administration of an effective amount of the synthetic peptide amides of the invention. Such cardiovascular diseases and conditions include, without limitation, coronary heart disease, ischemia, cardiac infarct, reperfusion injury and arrhythmia. See for example, Wu et al. "Cardioprotection of Preconditioning by Metabolic Inhibition in the Rat Ventricular Myocyte—Involvement of kappa Opioid Receptor" (1999) *Circulation Res* vol. 84: pp. 1388-1395. See also Yu et al. "Anti-Arrythmic Effect of kappa Opioid Receptor Stimulation in the Perfused Rat Heart: Involvement of a cAMP-Dependent Pathway" (1999) *J Mol Cell Cardiol*. vol. 31(10): pp. 1809-1819.

Diseases and conditions of other tissues and organs that can be prevented or treated by administration of an effective amount of the synthetic peptide amides of the invention include, but are not limited to ischemia, anoxia, stroke, brain or spinal cord injury and reperfusion injury.

Another form of kappa opioid receptor-associated pain treatable or preventable with the synthetic peptide amides of the invention is hyperalgesia. In one embodiment, the method includes administering an effective amount of a synthetic peptide amide of the invention to a mammal suffering from or at risk of developing hyperalgesia to prevent, ameliorate or completely aleviate the hyperalgesia.

The synthetic peptide amides of the invention can be administered by methods disclosed herein for the treatment or prevention of any hyperalgesic condition, such as, but without limitation, a hyperalgesic condition associated with allergic dermatitis, contact dermatitis, skin ulcers, inflammation, rashes, fungal irritation and hyperalgesic conditions associated with infectious agents, burns, abrasions, bruises, contusions, frostbite, rashes, acne, insect bites/stings, skin ulcers, mucositis, gingivitis, bronchitis, laryngitis, sore throat, shingles, fungal irritation, fever blisters, boils, Plantar's warts, surgical procedures or vaginal lesions. For instance, the synthetic peptide amides of the invention can be administered topically to a mucosal surface, such as the mouth, esophagus or larynx, or to the bronchial or nasal passages. Alternatively, the synthetic peptide amides of the invention can be administered topically to the vagina or rectum/anus.

Moreover, the synthetic peptide amides of the invention can be administered by methods disclosed herein for the treatment or prevention of any hyperalgesic condition associated with burns, abrasions, bruises, abrasions (such as corneal abrasions), contusions, frostbite, rashes, acne, insect bites/stings, skin ulcers (for instance, diabetic ulcers or a decubitus ulcers), mucositis, inflammation, gingivitis, bronchitis, laryngitis, sore throat, shingles, fungal irritation (such as athlete's foot or jock itch), fever blisters, boils, Plantar's warts or vaginal lesions (such as vaginal lesions associated with mycosis or sexually transmitted diseases). Methods contemplated for administration of the synthetic peptide amides of the invention for the treatment or prevention of hyperalgesia include those wherein the compound is topically applied to a surface in the eyes, mouth, larynx, esophagus, bronchial, nasal passages, vagina or rectum/anus.

Hyperalgesic conditions associated with post-surgery recovery can also be addressed by administration of the synthetic peptide amides of the invention. The hyperalgesic conditions associated with post-surgery recovery can be any hyperalgesic conditions associated with post-surgery recovery, such as for instance, radial keratectomy, tooth extraction, lumpectomy, episiotomy, laparoscopy and arthroscopy.

Hyperalgesic conditions associated with inflammation are also addressable by administration of the synthetic peptide amides of the invention. Periodontal inflammation, orthodontic inflammation, inflammatory conjunctivitis, hemorrhoids and venereal inflammations can be treated or prevented by topical or local administration of the synthetic peptide amides of the invention.

The invention also provides a method of inducing diuresis in a mammal in need thereof. The method includes administering to the mammal a composition comprising an effective amount of a synthetic peptide amide of the invention as described above.

The invention further provides a method of inducing prolactin secretion in a mammal. The method includes administering to the mammal a composition comprising an effective amount of a synthetic peptide amide of the invention as described above. The method of inducing prolactin secretion is suitable for treating a mammal, such as a human suffering from insufficient lactation, inadequate lactation, sub-optimal lactation, reduced sperm motility, an age-related disorder, type I diabetes, insomnia or inadequate REM sleep. In a particular aspect, the method includes co-administering the synthetic peptide amide with a reduced dose of a mu opioid agonist analgesic compound to produce a therapeutic analgesic effect, the compound having an associated side effect, wherein the reduced dose of the compound has a lower associated side effect than the side effect associated with the dose of the mu opioid agonist analgesic compound necessary to achieve the therapeutic analgesic effect when administered alone.

The present invention also provides a method of binding a kappa opioid receptor in a mammal, the method includes the step of administering to the mammal a composition containing an effective amount of a synthetic peptide amide of the present invention. The effective amount can be determined according to routine methods by one of ordinary skill in the art. For instance, the effective amount can be determined as a dosage unit sufficient to bind kappa opioid receptors in a mammal and cause an antinociceptive effect, an anti-inflammatory effect, an aquaretic effect, or an elevation of serum prolactin levels or any other kappa opioid receptor-responsive effect. Alternatively, the effective amount may be determined as an amount sufficient to approximate the $EC_{50}$ in a body fluid of the mammal, or an amount sufficient to approximate two or three, or up to about five or even about ten times the $EC_{50}$ in a therapeutically relevant body fluid of the mammal.

Synthesis of the Peptide Amides and Peptide Amide Dimers of the Invention (SEQ ID NO: 1):

Compound (1)

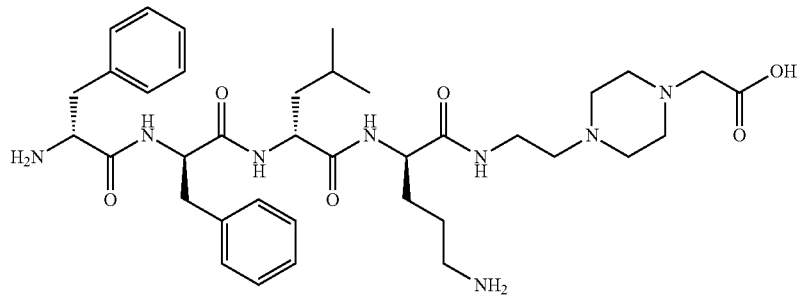

D-Phe-D-Phe-D-Leu-D-Orn-[4-(2-aminoethyl)-1-carboxymethyl-piperazine]-OH (SEQ ID NO: 1):

Compound (2)

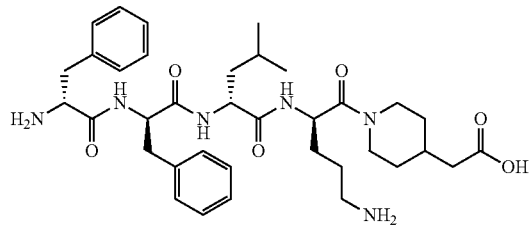

D-Phe-D-Phe-D-Leu-D-Orn-[4-carboxymethyl-piperidine]-OH (SEQ ID NO: 2):

Compound (3)

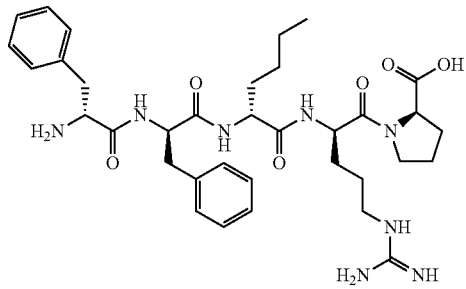

D-Phe-D-Phe-D-Nle-D-Arg-D-Pro-OH (SEQ ID NO: 1):

Compound (4)

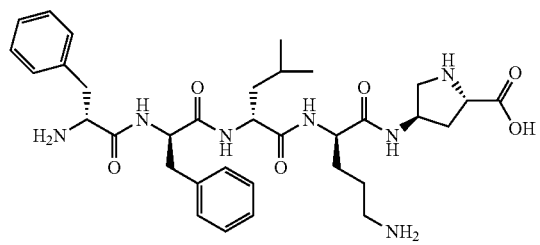

D-Phe-D-Phe-D-Leu-D-Orn-[(2S,4R)-
4-amino-pyrrolidine-2-carboxylic acid]-OH (SEQ ID NO: 1):

Compound (5)

D-Phe-D-Phe-D-Leu-D-Orn-[(2S,4S)-4-amino-pyrrolidine-
2-carboxylic acid]-OH (SEQ ID NO: 1):

Compound (6)

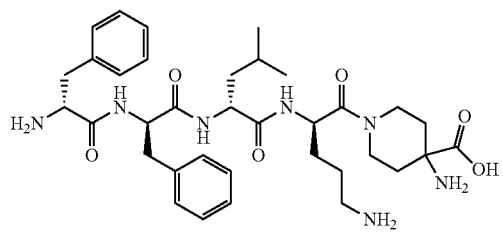

D-Phe-D-Phe-D-Leu-D-Orn-[omega
(4-aminopiperidine-4-carboxylic acid)]-OH (SEQ ID NO: 1):

Compound (7)

D-Phe-D-Phe-D-Leu-D-Orn-[omega(D/L-2-amino-3-
(4-N-piperidinyl)propionic acid)]-OH (SEQ ID NO: 1):

Compound (8)

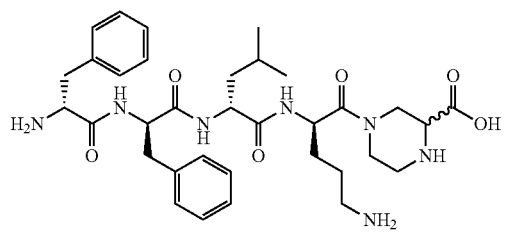

D-Phe-D-Phe-D-Leu-D-Orn-[omega
(D/L-4-piperazine-2-carboxylic acid)]-OH (SEQ ID NO: 1):

Compound (9)

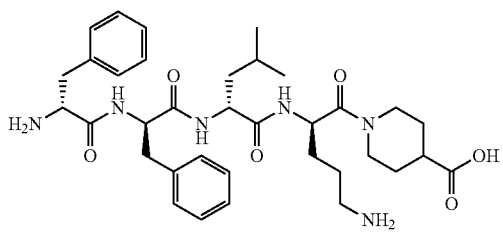

D-Phe-D-Phe-D-Leu-D-Orn-[Isonipecotic acid]-OH

-continued
(SEQ ID NO: 1): Compound (10)
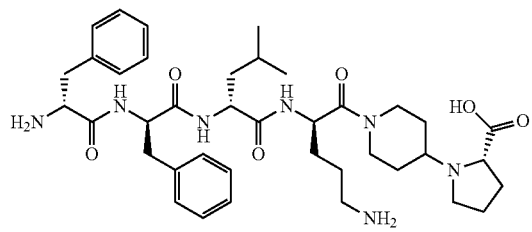
D-Phe-D-Phe-D-Leu-D-Orn-[N-(4-piperidinyl)-L-proline]-OH
(SEQ ID NO: 1): Compound (11)
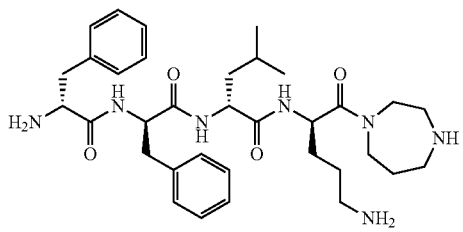
D-Phe-D-Phe-D-Leu-D-Orn-[homopiperazine amide]
(SEQ ID NO: 1): Compound (12)
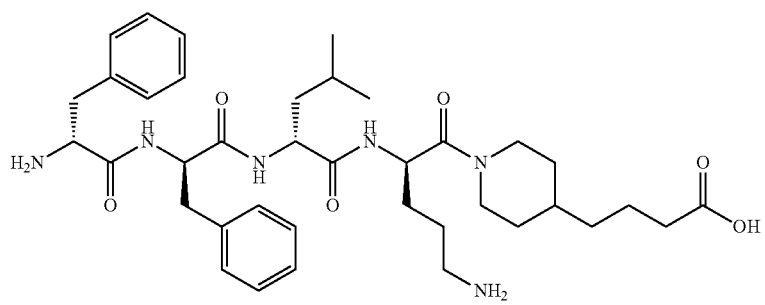
D-Phe-D-Phe-D-Leu-D-Orn-[4-(4-piperidinyl)-butanoic acid]-OH
(SEQ ID NO: 1): Compound (13)
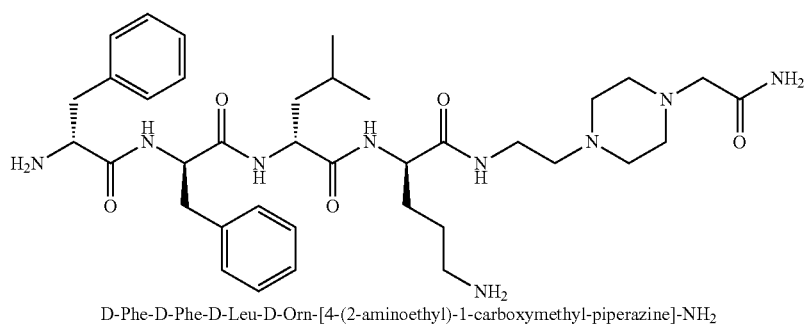
D-Phe-D-Phe-D-Leu-D-Orn-[4-(2-aminoethyl)-1-carboxymethyl-piperazine]-NH$_2$
(SEQ ID NO: 1): Compound (14)
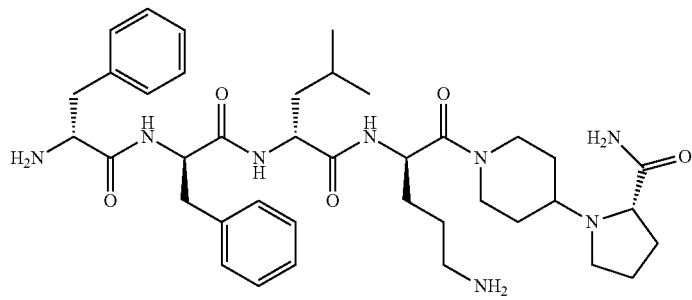
D-Phe-D-Phe-D-Leu-D-Orn-[N-(4-piperidinyl)-L-proline]-NH$_2$ (SEQ ID NO: 1):

Compound (15)

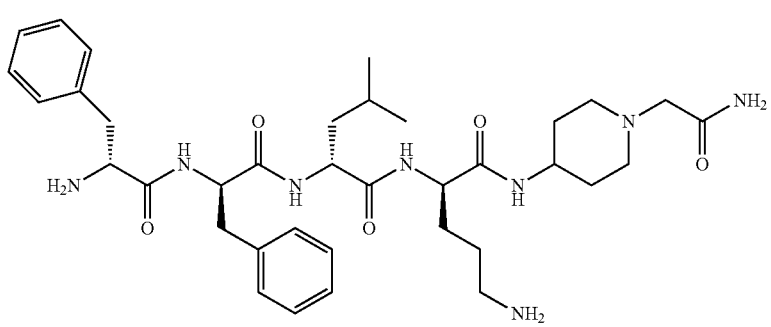

D-Phe-D-Phe-D-Leu-D-Orn-[4-amino-1-carboxymethyl-piperidine]-NH₂

(SEQ ID NO: 1):

Compound (16)

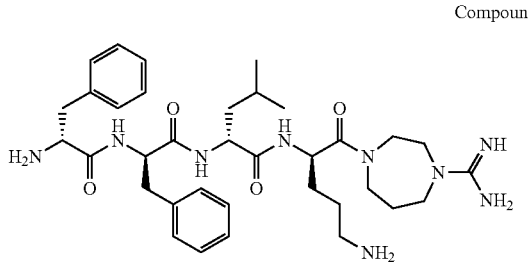

D-Phe-D-Phe-D-Leu-D-Orn-[4-amidinohomopiperazine amide]

(SEQ ID NO: 1):

Compound (17)

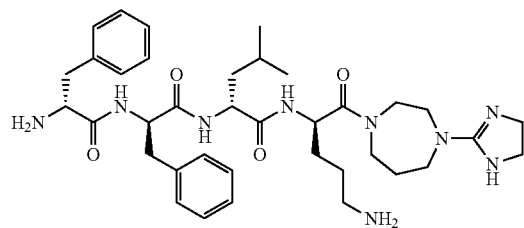

D-Phe-D-Phe-D-Leu-D-Orn-[4-(4,5-dihydro-
1H-imidazol-2-yl)homopiperazine amide]

(SEQ ID NO: 1):

Compound (18)

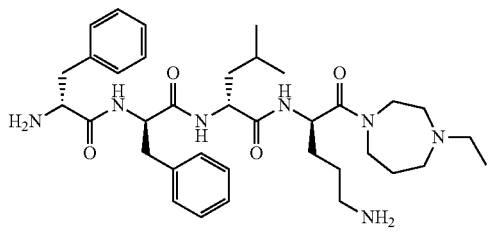

D-Phe-D-Phe-D-Leu-D-Orn-[4-ethylhomopiperazine amide]

(SEQ ID NO: 1):

Compound (19)

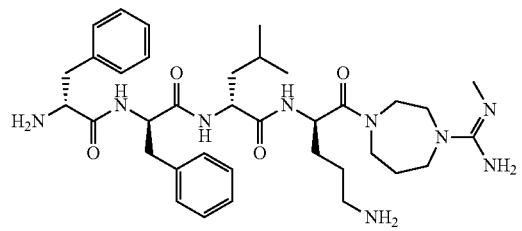

D-Phe-D-Phe-D-Leu-D-Orn-[4-(N-methyl)
amidino-homopiperazine amide]

(SEQ ID NO: 3):

Compound (20)

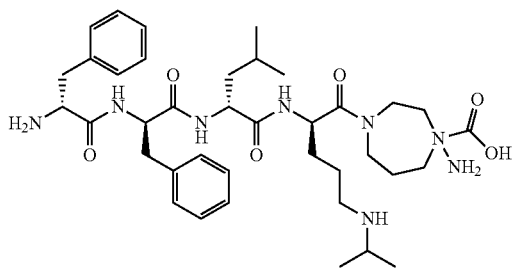

D-Phe-D-Phe-D-Leu-(δ-iPr)D-Orn-[omega
(4-aminopiperidine-4-carboxylic acid)]-OH (SEQ ID NO: 4):

Compound (21)

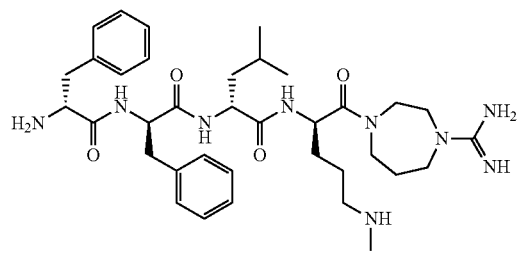

D-Phe-D-Phe-D-Leu-(δ-Me)D-Orn-
[4-amidinohomopiperazine amide]

-continued (SEQ ID NO: 3):

Compound (22)

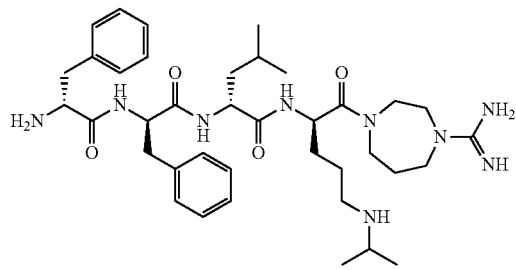

D-Phe-D-Phe-D-Leu-(δ-iPr)D-Orn-
[4-amidinohomopiperazine amide]

(SEQ ID NO: 4):

Compound (23)

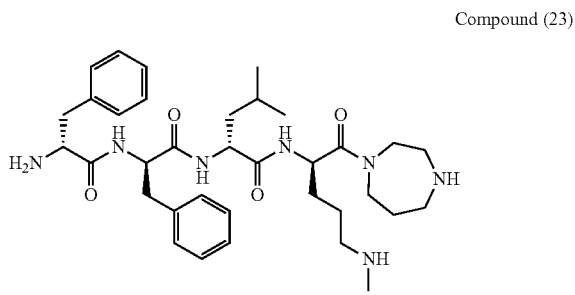

D-Phe-D-Phe-D-Leu-(δ-Me)D-Orn-[homopiperazine amide]

(SEQ ID NO: 3):

Compound (24)

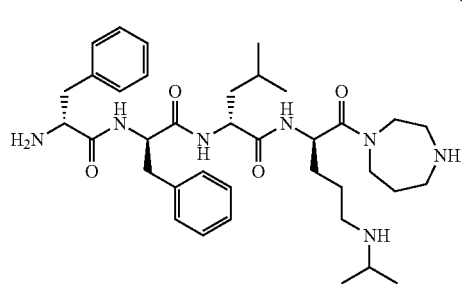

D-Phe-D-Phe-D-Leu-(δ-iPr)D-Orn-[homopiperazine amide]

(SEQ ID NO: 5):

Compound (25)

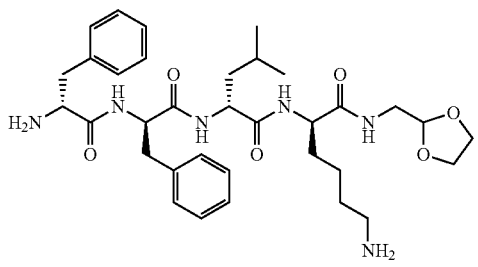

D-Phe-D-Phe-D-Leu-D-Lys-[1,3-dioxolan-2-yl)
methanamine amide]

(SEQ ID NO: 5):

Compound (26)

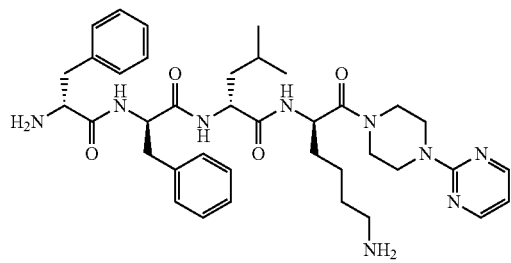

D-Phe-D-Phe-D-Leu-D-Lys-[2-(piperazin-1-yl)pyrimidine amide]

(SEQ ID NO: 5):

Compound (27)

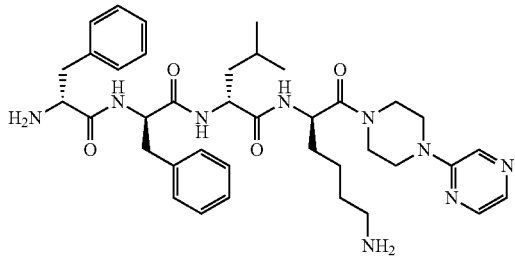

D-Phe-D-Phe-D-Leu-D-Lys-[2-(piperazin-1-yl)pyrazine amide]

(SEQ ID NO: 5):

Compound (28)

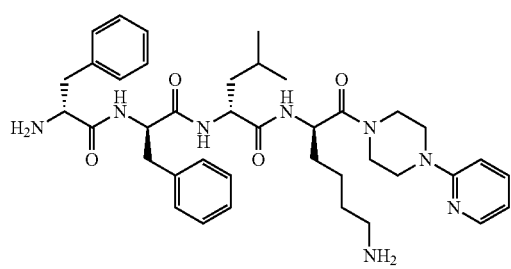

D-Phe-D-Phe-D-Leu-D-Lys-[1-(pyridin-2-yl)piperazine amide]

(SEQ ID NO: 5):

Compound (29)

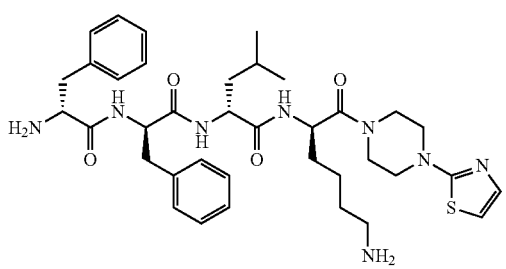

D-Phe-D-Phe-D-Leu-D-Lys-[2-(piperazin-1-yl)thiazole amide]

(SEQ ID NO: 5): Compound (30)

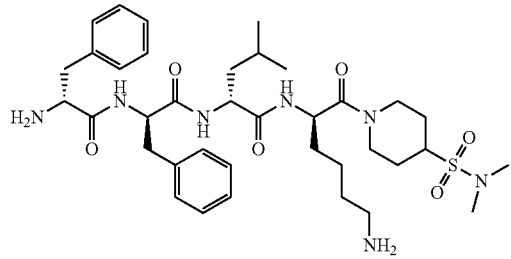

D-Phe-D-Phe-D-Leu-D-Lys-[N,N-dimethylpiperazine-1-sulfonamide amide]

(SEQ ID NO: 5): Compound (31)

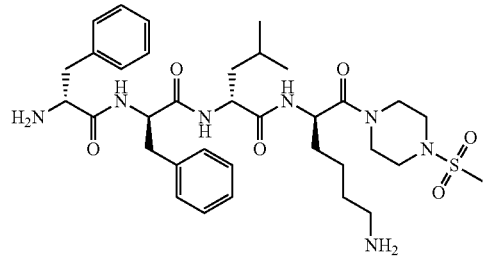

D-Phe-D-Phe-D-Leu-D-Lys-[1-(methylsulfonyl)piperazine amide]

(SEQ ID NO: 5): Compound (32)

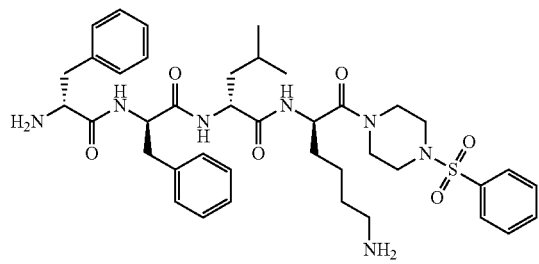

D-Phe-D-Phe-D-Leu-D-Lys-[1-(phenylsulfonyl)piperazine amide]

(SEQ ID NO: 5): Compound (33)

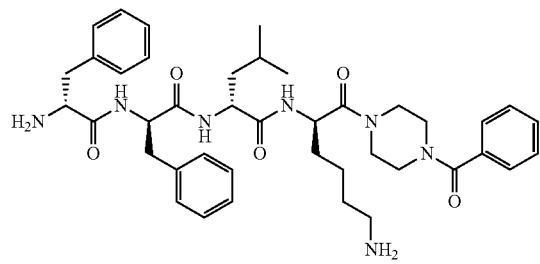

D-Phe-D-Phe-D-Leu-D-Lys-[phenyl(piperazin-1-yl)methanone amide]

(SEQ ID NO: 5): Compound (34)

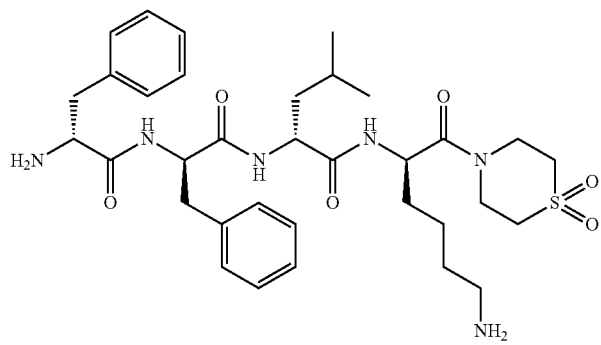

D-Phe-D-Phe-D-Leu-D-Lys-[thiolmorpholine-1,1-dioxide amide]

(SEQ ID NO: 5): Compound (35)

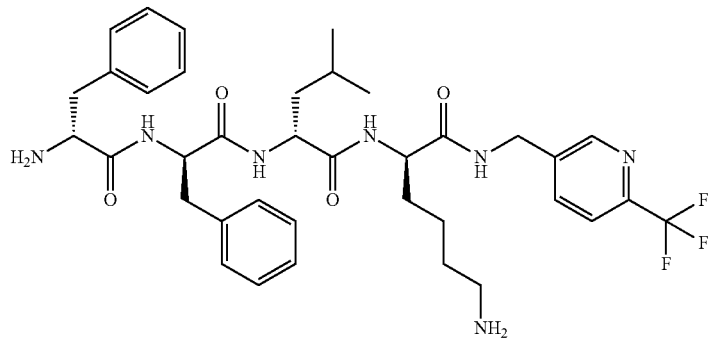

D-Phe-D-Phe-D-Leu-D-Lys-[6-trifluoromethyl-3-aminomethyl pyridine amide]

(SEQ ID NO: 5):
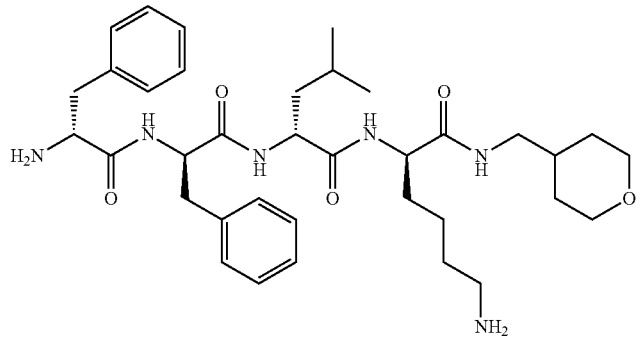
D-Phe-D-Phe-D-Leu-D-Lys-N-methyl-1-(tetrahydro-2H-pyran-4-yl)methanamine amide
Compound (36)
(SEQ ID NO: 5):
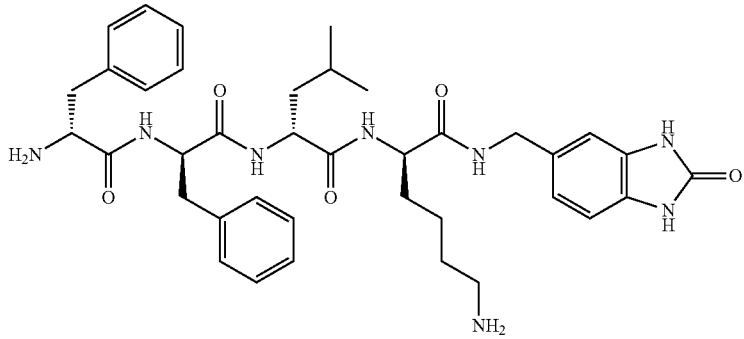
H-D-Phe-D-Phe-D-Leu-D-Lys-[5-(aminomethyl)-1H-benzo[d]imidazol-2(3H)-one amide]
Compound (37)
(SEQ ID NO: 5):
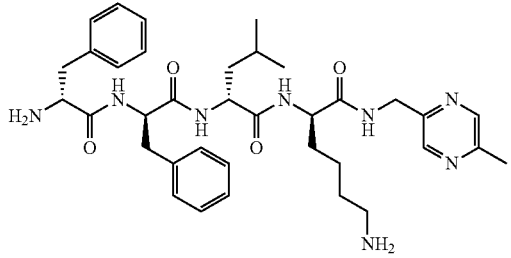
D-Phe-D-Phe-D-Leu-D-Lys-N-methyl-1-
(5-methylpyrazin-2-yl)-methanamine amide)
Compound (38)

Compound (39)
D-Phe-D-Phe-D-Leu-D-Orn-εLys-OH
                          |
      D-Phe-D-Phe-D-Leu-D-Orn
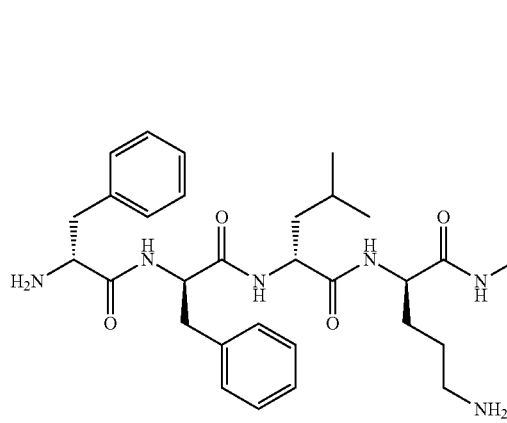
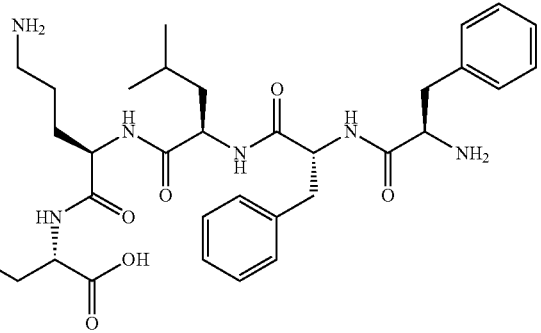
Compound (40)
D-Phe-D-Phe-D-Leu-D-Orn-εLys-OH
                          |
                    D-Leu-D-Orn
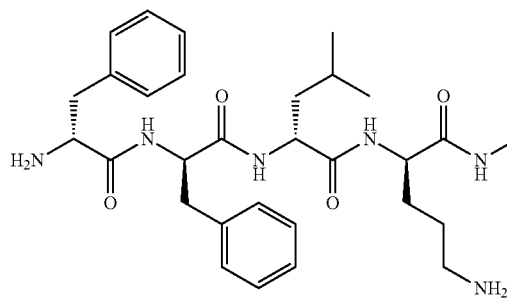
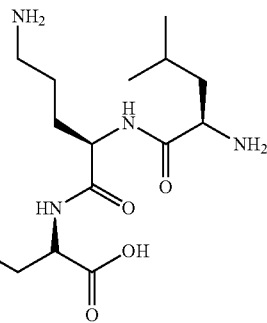
Compound (41)
D-Phe-D-Phe-D-Leu-D-Orn-εLys-OH
                          |
              D-Phe-D-Leu-D-Orn
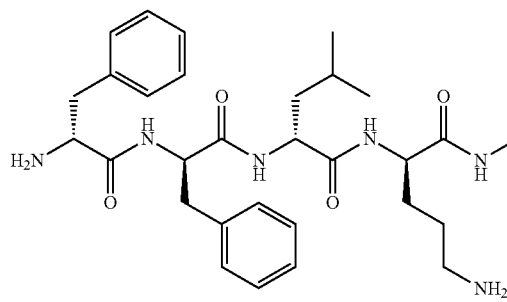
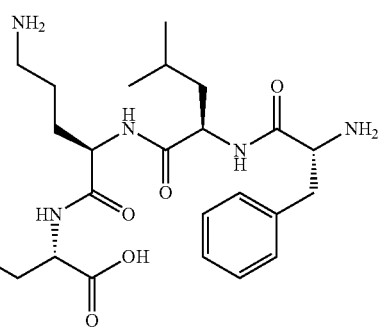

Compound (42)
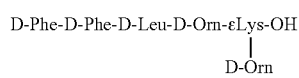
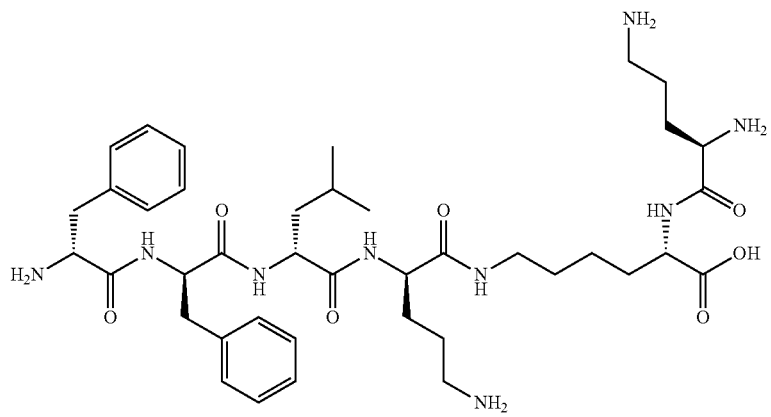
Compound (43)
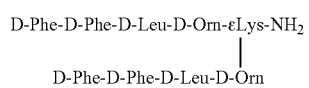
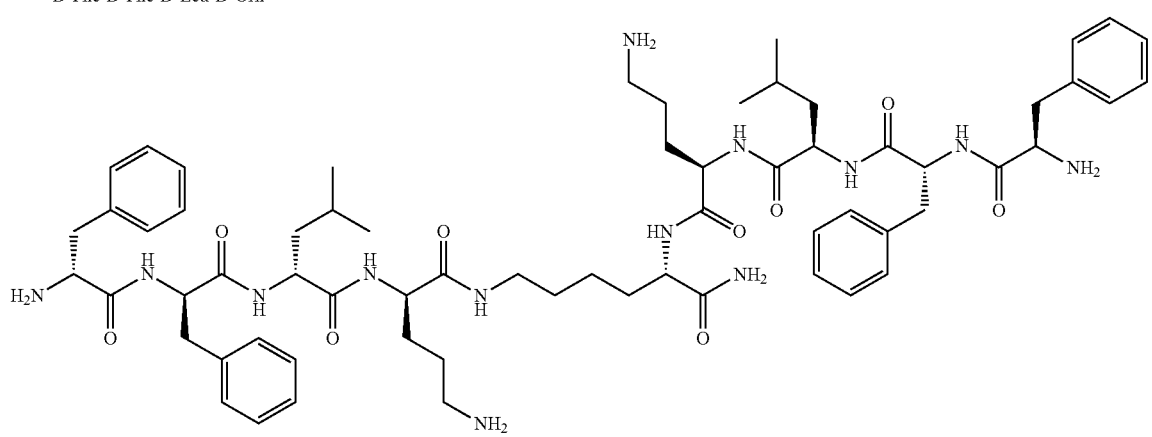
Compound (44)
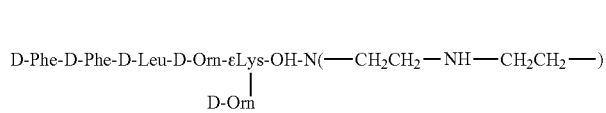
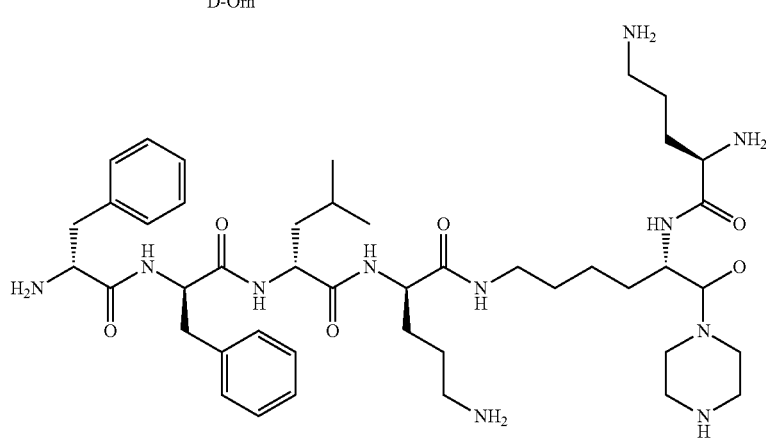

-continued
Compound (45)
D-Phe-D-Phe-D-Leu-D-Orn-εLys-OH
               |
             D-Orn
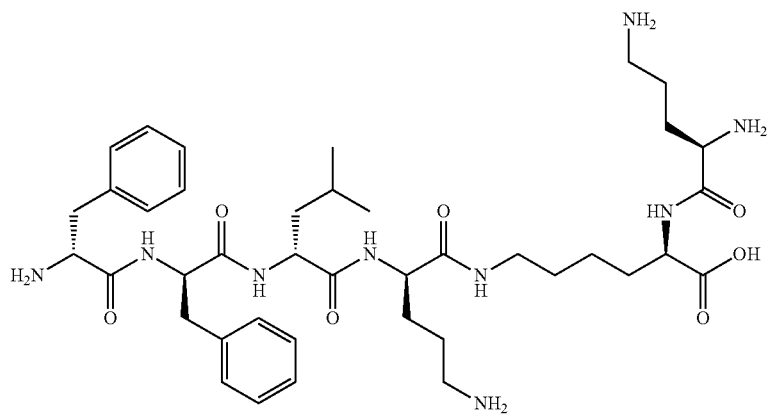
Compound (46)
D-Phe-D-Phe-D-Leu-D-Orn-εLys-OH
               |
         D-Leu-D-Orn
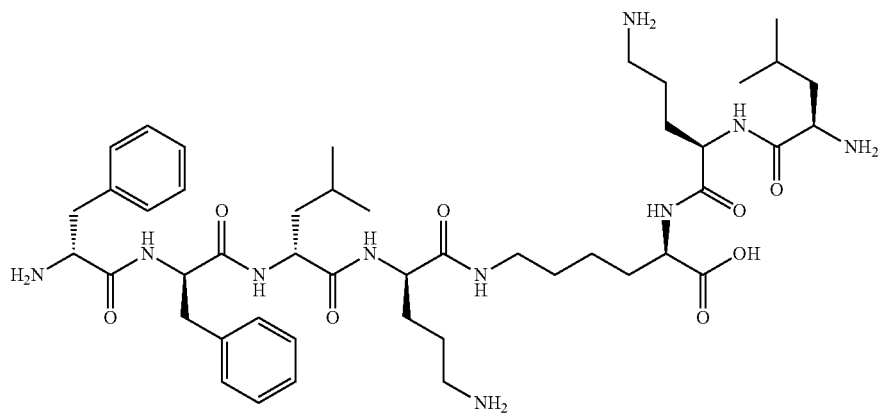
Compound (47)
D-Phe-D-Phe-D-Leu-D-Orn-εLys-OH
               |
       D-Phe-D-Leu-D-Orn
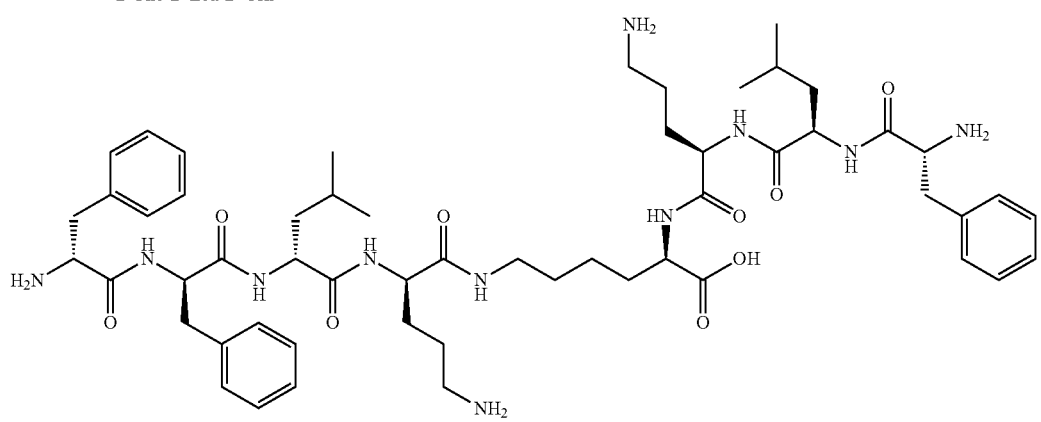

Compound (48)
D-Phe-D-Phe-D-Leu-D-Orn-εLys-OH
                          |
D-Phe-D-Phe-D-Leu-D-Orn
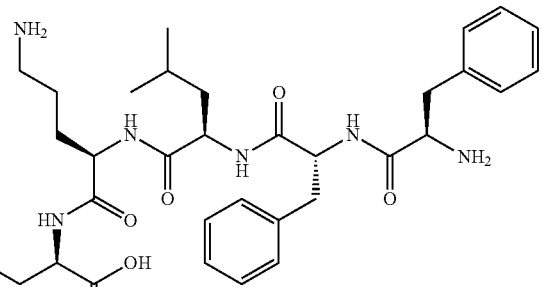
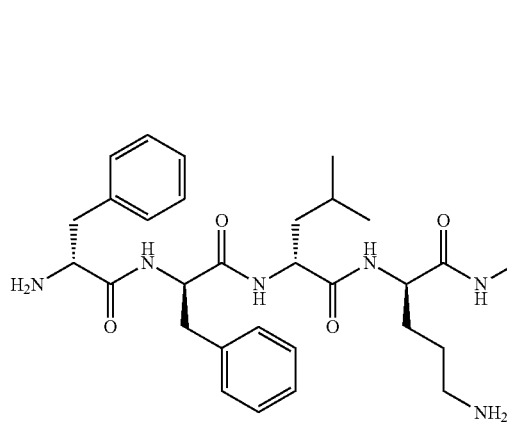
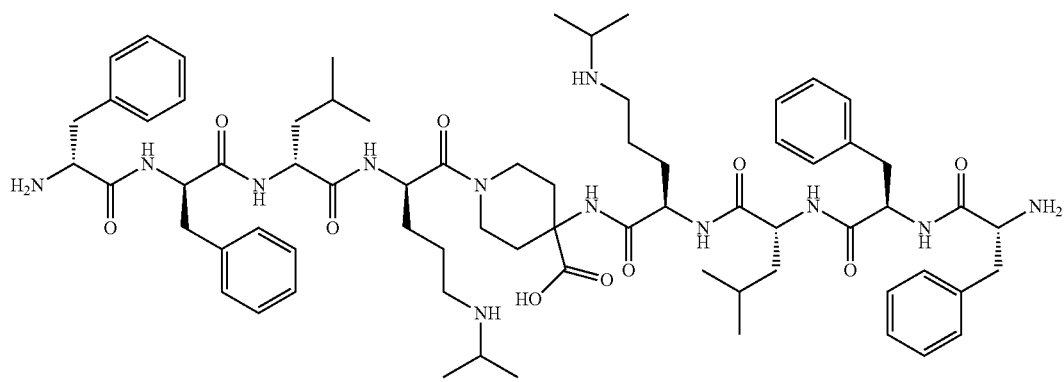
Compound (49)
1N,4N-bis-[D-Phe-D-Phe-D-Leu-(iPr)D-Orn]-4-amino-4-carboxylic-piperidine
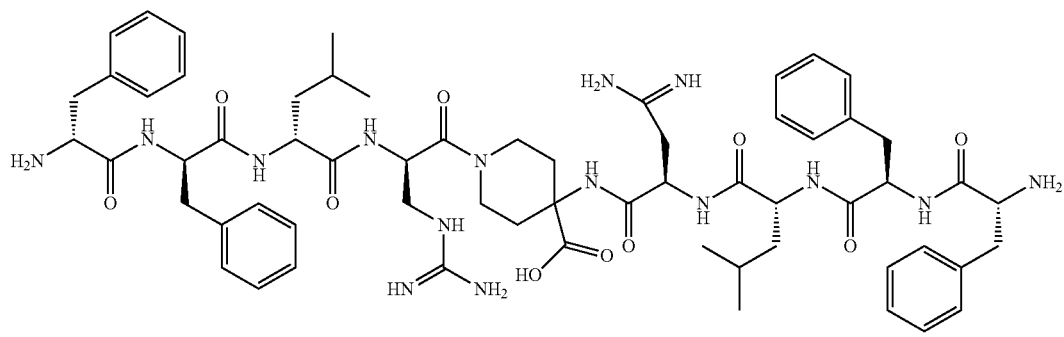
Compound (50)
1N,4N-bis-[D-Phe-D-Phe-D-Leu-D-Dap(amidino)]-4-amino-4-carboxylic piperidine Compound (51)
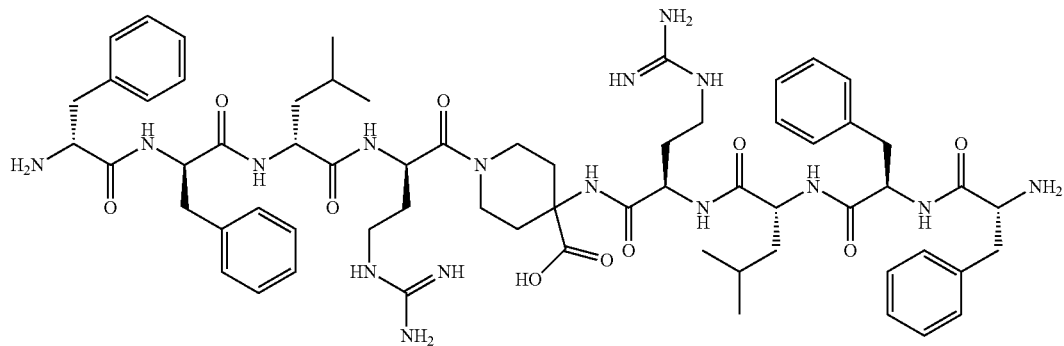
1N,4N-bis-(D-Phe-D-Phe-D-Leu-D-Nar)-4-amino-4-carboxylic piperidine
Compound (52)
D-Phe-D-Phe-D-Leu-(D-Lys-GlyLactam)$_2$
|
D-Phe-D-Phe-D-Leu
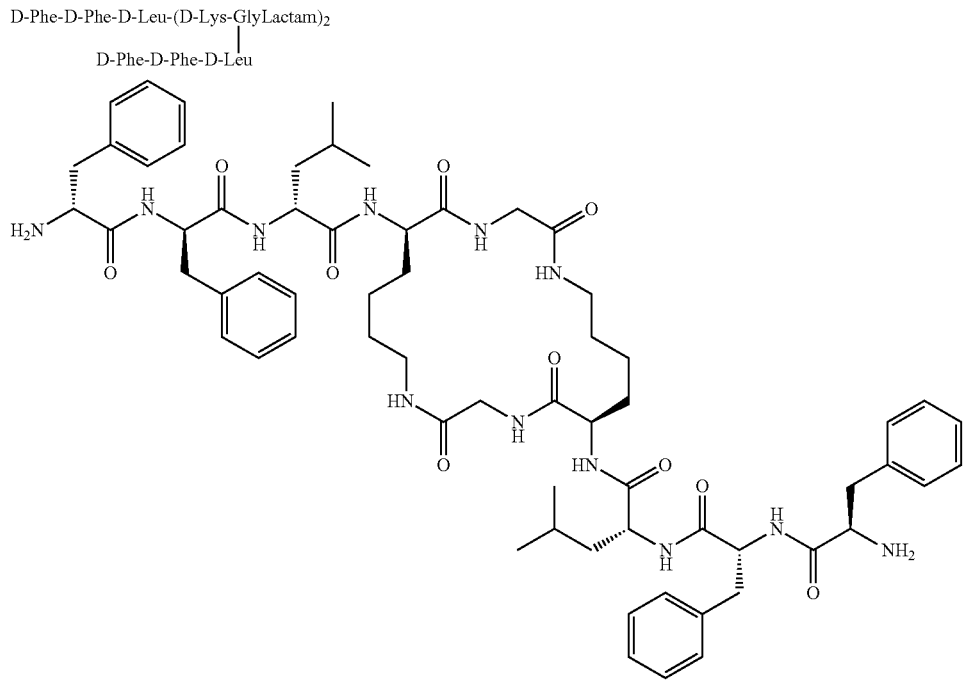
(SEQ ID NO: 1):
Compound (53)
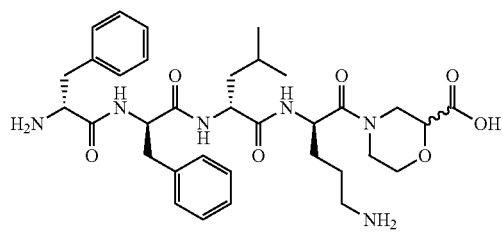
D-Phe-D-Phe-D-Leu-D-Orn-[R/S-2-carboxymorpholine]-OH
(SEQ ID NO: 1):
Compound (54)
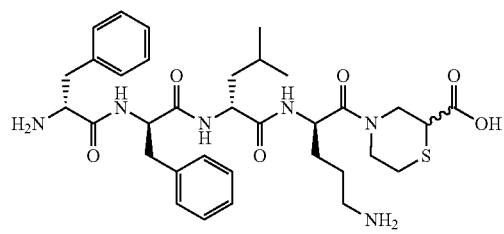
D-Phe-D-Phe-D-Leu-D-Orn-[R/S-2-carboxythiomorpholine]-OH -continued (SEQ ID NO: 1):

Compound (55)

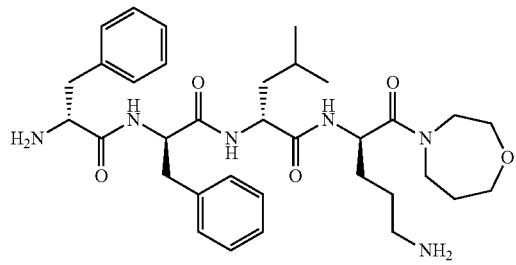

D-Phe-D-Phe-D-Leu-D-Orn-N(homomorpholine)

(SEQ ID NO: 1):

Compound (56)

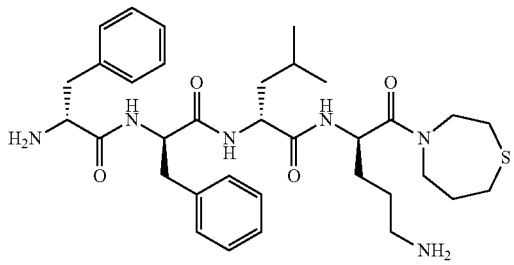

D-Phe-D-Phe-D-Leu-D-Orn-N(homothiomorpholine)

(SEQ ID NO: 6):

Compound (57)

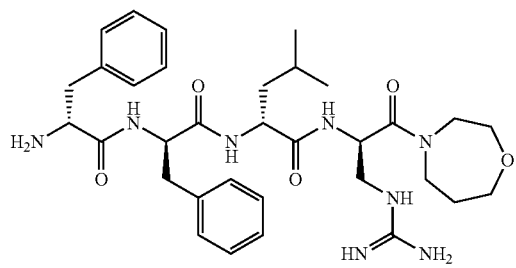

D-Phe-D-Phe-D-Leu-D-Dap(amidino)-[homomorpholine amide]

(SEQ ID NO: 6):

Compound (58)

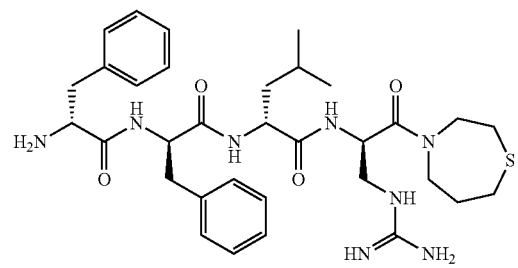

D-Phe-D-Phe-D-Leu-D-Dap(amidino)-[homothiomorpholine amide]

(SEQ ID NO: 6):

Compound (59)

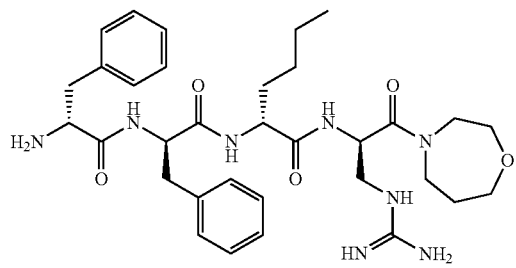

D-Phe-D-Phe-D-Nle-D-Dap(amidino)-[homomorpholine amide]

(SEQ ID NO: 6):

Compound (60)

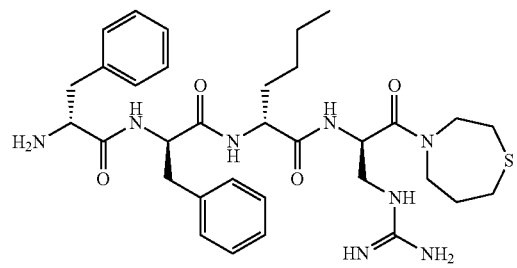

D-Phe-D-Phe-D-Nle-D-Dap(amidino)-[homothiomorpholine amide]

(SEQ ID NO: 7):

Compound (61)

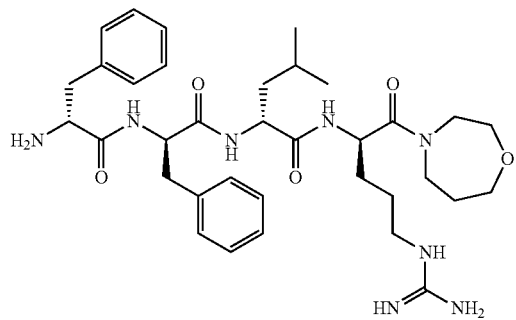

D-Phe-D-Phe-D-Leu-D-Arg-[homomorpholine amide]

(SEQ ID NO: 7):

Compound (62)

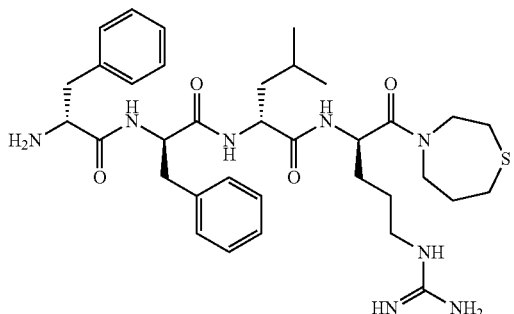

D-Phe-D-Phe-D-Leu-D-Arg-[homothiopiperazine amide]

(SEQ ID NO: 4):

Compound (63)

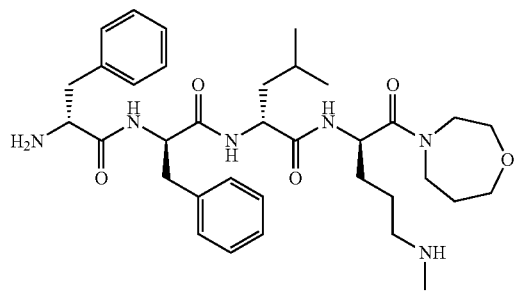

D-Phe-D-Phe-D-Leu-D-Orn(Me)-[homomorpholine amide]
(SEQ ID NO: 3):

Compound (64)

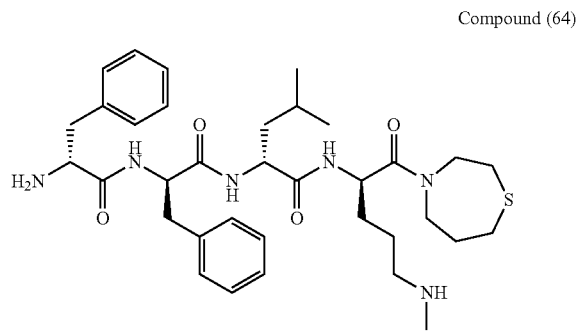

D-Phe-D-Phe-D-Leu-D-Orn(Me)-[homothiomorpholine amide]
(SEQ ID NO: 3):

Compound (65)

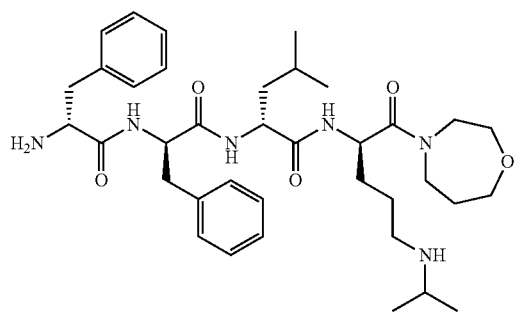

D-Phe-D-Phe-D-Leu-D-Orn(iPr)-[homomorpholine amide]

Compound (66)

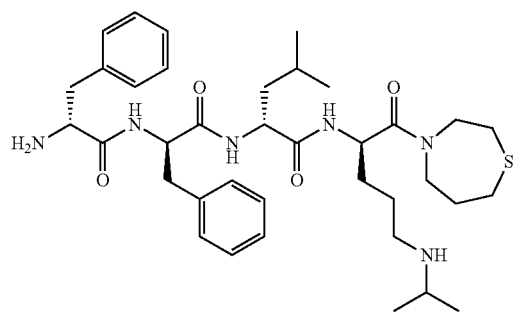

D-Phe-D-Phe-D-Leu-D-Orn(iPr)-[homothiomorpholine amide]

EXAMPLES

General Experimental Synthetic Methods

Amino acid derivatives and resins were purchased from commercial providers (Novabiochem, Bachem, Peptide International and PepTech Corporation). Other chemicals and solvents were purchased from Sigma-Aldrich, Fisher Scientific and VWR. The compounds herein were synthesized by standard methods in solid phase peptide chemistry utilizing both Fmoc and Boc methodology. Unless otherwise specified, all reactions were performed at room temperature.

The following standard references provide guidance on general experimental setup, and the availability of required starting material and reagents: Kates, S. A., Albericio, F., Eds., *Solid Phase Synthesis, A Practical Guide*, Marcel Dekker, New York, Basel, (2000); Bodanszky, M., Bodanszky, A., Eds., *The Practice of Peptide Synthesis, Second Edition*, Springer-Verlag, (1994); Atherton, E., Sheppard, R. C., Eds., *Solid Phase Peptide Synthesis, A Practical Approach*, IRL Press at Oxford University Press, (1989); Stewart, J. M., Young, J. D., *Solid Phase Synthesis*, Pierce Chemical Company, (1984); Bisello, et al., *J. Biol. Chem.* 273, 22498-22505 (1998); and Merrifield, R. B., *J. Am. Chem. Soc.* 85, 2149-2154 (1963).

Additional abbreviations used herein:
ACN: acetonitrile
Aloc: allyloxycarbonyl
Boc: tert-butoxycarbonyl
BOP: benzotriazole-1-yl-oxy-tris(dimethylamino)-phosphonium hexafluorophosphate
Cbz: benzyloxycarbonyl.
Cbz-OSu: Nα-(Benzyloxycarbonyloxy) succinimide
DBU: 1,8-diazabicyclo[5.4.0]undec-7-ene
DCM: Dichloromethane
Dde: 1-(4,4-dimethyl-2,6-dioxocyclohex-1-ylidene)ethyl
DIC: N,N'-diisopropylcarbodiimide
DIEA: N,N-diisopropylethylamine
DMF: N,N-dimethylformamide
Fmoc: 9-fluorenylmethoxycarbonyl
HATU: 2-(1H-9-azabenzotriazole-1-yl)-1,1,3,3-tetramethylaminium hexafluorophosphate
HBTU: 2-(1H-benzotriazole-1-yl)-1,1,3,3-tetramethylaminium hexafluorophosphate
HOBt: 1-hydroxybenzotriazole
HPLC: high performance liquid chromatography
i: iso
ivDde: 1-(4,4-dimethyl-2,6-dioxocyclohex-1-ylidene)-3-methylbutyl
NMM: 4-methyl morpholino
NMP: N-methylpyrrolidinone
All: allyl
o-NBS-Cl: o-nitrobenzenesulfonyl chloride
Pbf: 2,2,4,6,7-pentamethyldihydro-benzofuran-5-sulfonyl
PyBOP: benzotriazole-1-yloxy-tris-pyrrolidino-phosphonium hexafluorophosphate
RP: reversed phase
TBTU: 2-(1H-benzotriazole-1-yl)-1,1,3,3-tetramethyluronium tetrafluoroborate
TEAP: triethylammonium phosphate
TFA: trifluoroacetic acid
TIS: triisopropylsilane
TMOF: trimethyl orthoformate
TMSOTf: trimethylsilyl trifluoromethanesulfonate
Trt: trityl Peptides synthesized by Fmoc methodology were cleaved with a mixture of TFA/TIS/H$_2$O (v/v/v=95:2.5:2.5). The cleavage step in the Boc methodology was accomplished either with a mixture of HF/anisole (v/v=9:1) or with a mixture of TMSOTf/TFA/m-cresol (v/v/v=2:7:1).

Coupling reactions in peptide chain elongation were carried out either manually on a peptide synthesizer and mediated by coupling reagents with a 2 to 4-fold excess amino acid derivatives. The coupling reagents used in the synthesis of the various compounds of the invention were chosen from the following combinations: DIC/HOBt, HATU/DIEA, HBTU/DIEA, TBTU/DIEA, PyBOP/DIEA, and BOP/DIEA.

Deprotection of the side chain of amino acid in position No. 4 (designated Xaa$_4$ in the final synthetic peptide amide product) of resin bound peptides was achieved as follows: Peptides were assembled starting from Xaa$_4$ and progressively adding Xaa$_3$, then Xaa$_2$ and finally, Xaa$_1$. The side chain protecting groups of the diamino acid introduced at Xaa$_4$ were selectively removed as follows: (i) N-Dde or N-ivDde groups were removed by 2-4% hydrazine in DMF. See Chabra, S. R., et al., *Tetrahedron Lett*. 39:1603-1606 (1998) and Rohwedder, B., et al., *Tetrahedron Lett.,* 39: 1175 (1998); (ii) N-Aloc: removed by 3 eq. (Ph$_3$P)$_4$Pd in CHCl$_3$/AcOH/NMM (v/v/v=37:2:1). See Kates, S. A., et al. in "*Peptides Chemistry, Structure and Biology, Proc. 13$^{th}$ American Peptide Symposium*", Hodges, R. S. and Smith, J. A. (Eds), ESCOM, Leiden, 113-115 (1994).

When peptides were assembled with Boc protection methodology, the side chain protecting group of the diamino acids introduced at Xaa$_4$ was N-Fmoc, which was removed by 20-30% piperidine in DMF.

Isopropylation of the terminal nitrogen on the side chain of amino acid at Xaa$_4$ of resin bound peptides was achieved as follows: After deprotection, the resin bound peptide with the free ω-amino function at Xaa$_4$ was reacted with a mixture of acetone and NaBH(OAc)$_3$ in TMOF producing the resin bound Nω-isopropyl peptide.

Monomethylation of the terminal nitrogen on the side chain of amino acid at Xaa$_4$ of resin bound peptides: To synthesize resin bound Nω-methyl peptides, the free ω-amino function was first derivatized with o-nitrobenzenesulfonyl chloride (o-NBS-Cl; Biron, E.; Chatterjee, J.; Kessler, H. Optimized selective N-methylation of peptides on solid support. *J. Pep. Sci.* 12:213-219 (2006). The resulting sulfonamide was then methylated with a mixture of dimethylsulphate and 1,8-diaza-bicyclo[5.4.0]undec-7-ene in NMP. The o-NBS protecting group was subsequently removed by a mixture of mercaptoethanol and 1,8-diazabicyclo[5.4.0]undec-7-ene in NMP.

Guanylation of the terminal nitrogen on the side chain of amino acid at Xaa$_4$ of resin bound peptides: After deprotection, the resin bound peptide with the free ω-amino function in position No. 4 was reacted with a mixture of 1H-pyrazole-1-carboxamidine hydrochloride (Bernatowicz, M. S., et al., *J. Org. Chem.* 57, 2497-2502 (1992) and DIEA in DMF producing the resin bound Nω-guanidino peptide.

Peptides were purified by preparative HPLC in triethylammonium phosphate (TEAP) or trifluoroacetic acid (TFA) buffers. When required, the compounds were finally converted to trifluoroacetate or acetate salts using conventional HPLC methodology. Fractions with purity exceeding 97% were pooled and lyophilized. Purity of the synthesized peptides was determined by analytical RP-HPLC.

Analytical RP-HPLC was performed on a Waters 600 multisolvent delivery system with a Waters 486 tunable absorbance UV detector and a Waters 746 data module. HPLC analyses of peptides were carried out using a Vydac C$_{18}$ column (0.46×25 cm, 5 μm particle size, 300 Å pore size) at a flow rate of 2.0 ml/min. Solvents A and B were 0.1% TFA in H$_2$O and 0.1% TFA in 80% ACN/20% H$_2$O, respectively. Retention times (t$_R$) are given in min. Preparative RP-HPLC was accomplished using a Vydac C$_{18}$ preparative cartridge (5×30 cm, 15-20 μm particle size, 300 Å pore size) at a flow rate of 100 ml/min, on a Waters Prep LC 2000 preparative chromatograph system with a Waters 486 tunable absorbance UV detector and a Servogor 120 strip chart recorder. Buffers A and B were 0.1% TFA in H$_2$O and 0.1% TFA in 60% ACN/40% H$_2$O, respectively. HPLC analysis of the final compound was performed on a Hewlett Packard 1090 Liquid Chromatograph using a Phenomenex Synergi MAX-RP C$_{12}$ column (2.0×150 mm, 4 μm particle size, 80 Å pore size) at a flow rate of 0.3 ml/min at 40° C. Buffers A and B were 0.01% TFA in H$_2$O and 0.01% TFA in 70% ACN/30% H$_2$O, respectively. The identity of the synthetic peptide amides was confirmed by electrospray mass spectrometry. Mass spectra were recorded on a Finnigan LCQ mass spectrometer with an ESI source.

Example 1

Synthesis of Compound (1): D-Phe-D-Phe-D-Leu-D-Orn-[4-(2-aminoethyl)-1-carboxymethyl-piperazine]-OH (SEQ ID NO: 1)

Figure 1:
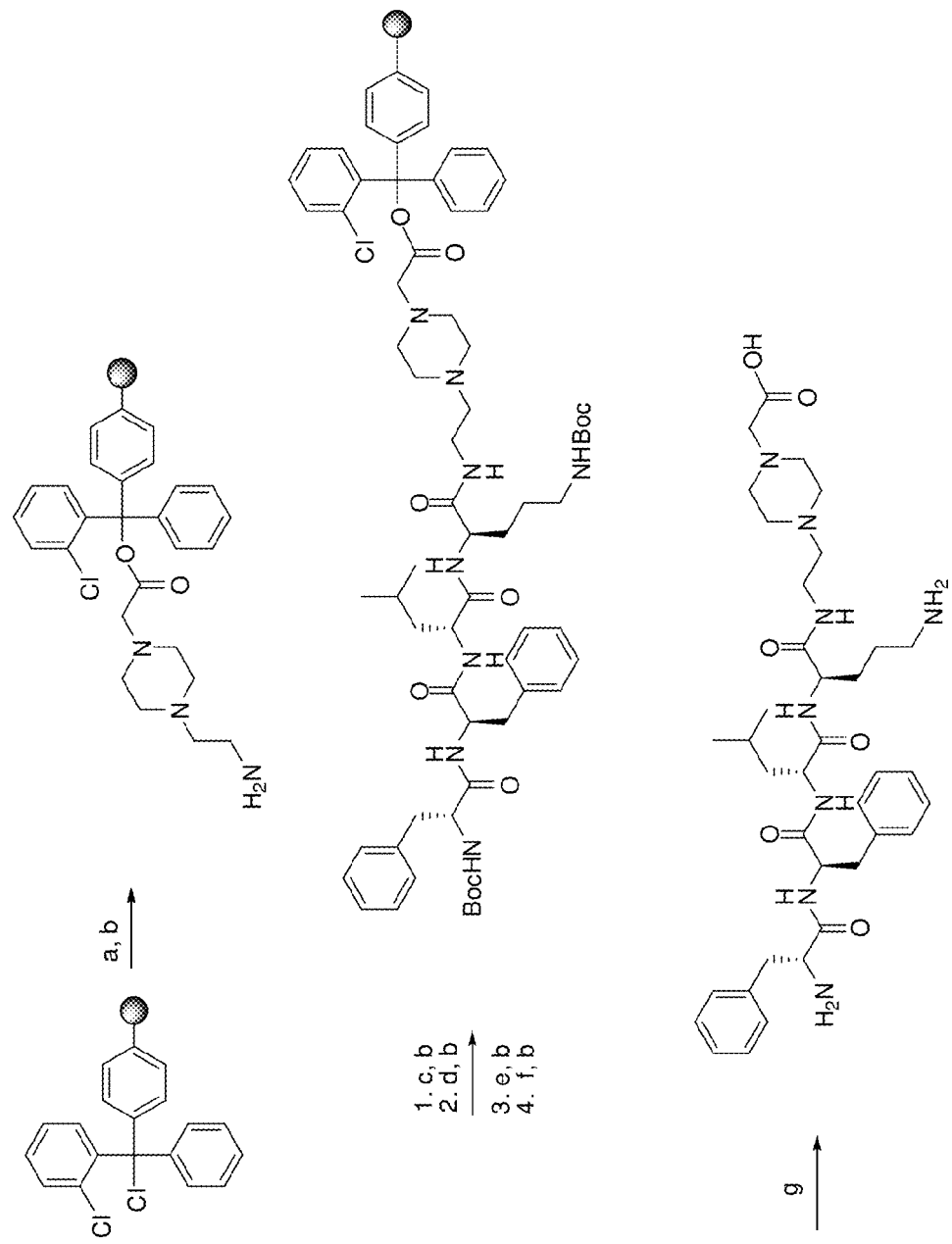
FIG. 1: Shows the general scheme used in the synthesis of compound (1). D-Phe-D-Phe-D-Leu-D-Orn-[4-(2-aminoethyl)-1-carboxymethylpiperazine]-OH (SEQ ID NO: 1): Steps a-g were carried out with the following reactants or conditions: a) Fmoc-4-(2-aminoethyl)-1-carboxylmethyl-piperazine, DIEA, DCM; b) 25% piperidine/DMF; c) Fmoc-D-Orn(Boc)-OH, DIC, HOBt, DMF; d) Fmoc-D-Leu-OH, DIC, HOBt, DMF; e) Fmoc-D-Phe-OH, DIC, HOBt, DMF; f) Boc-D-Phe-OH, DIC, HOBt, DMF; g) TFA/TIS/H2O (95:2.5:2.5).

See FIG. 1 for the general scheme used for the synthesis of compound (1). The amino acid derivatives used were Boc-D-Phe-OH, Fmoc-D-Phe-OH, Fmoc-D-Leu-OH, Fmoc-D-Orn(Boc)-OH, and Fmoc-4-(2-aminoethyl)-1-carboxymethyl-piperazine dihydrochloride. The fully protected resin-bound peptide was synthesized on a SYMPHONY Multiple Synthesizer (Protein Technology Inc.) starting from 2-Chlorotrityl chloride resin (0.4 mmol; Novabiochem). The attachment of the first amino acid to the resin was achieved by treatment with a mixture of Fmoc-4-(2-aminoethyl)-1-carboxymethyl-piperazine dihydrochloride (0.24 g, 0.5 mmol; Chem-Impex International Inc.) and DIEA (0.35 mL, 2 mmol) in DMF (7 ml) at room temperature for 4 hours. The resin was washed with 3×DCM/MeOH/DIEA (v/v/v=17:2:1) and 3×DCM. The subsequent peptide chain elongation was achieved by HBTU/DIEA mediated single couplings with a 3-fold excess of amino acid derivatives. The Fmoc group was removed by 25% piperidine in DMF. For cleavage, the final peptide resin was treated with a mixture of TFA/TIS/H$_2$O (15 ml, v/v/v=95: 2.5:2.5) at room temperature for 90 min. The resin was filtered and washed with TFA. The filtrate was evaporated in vacuo and the crude peptide (0.2 g, D-Phe-D-Phe-D-Leu-D-Orn-[4-(2-aminoethyl)-1-carboxymethyl-piperazine]-OH) (SEQ ID NO: 1) was precipitated from diethyl ether.

For purification, the above crude peptide (0.2 g) was dissolved in 0.1% TFA in H$_2$O (50 ml) and the solution was loaded onto an HPLC column and purified using a TFA buffer system (buffers A=0.1% TFA in H$_2$O and B=0.1% TFA in 60% ACN/40% H$_2$O). The compound was eluted with a linear gradient of buffer B, 25% B to 75% B over 30 min, t$_R$=35% B. The fractions with purity exceeding 97% were pooled, frozen, and dried on a lyophilizer to yield the purified peptide as a white amorphous powder (101 mg). HPLC analysis: t$_R$=16.24, purity 100%, gradient 5% B to 25% B over 20 min; MS (M+H$^+$): expected molecular ion mass 709.4, observed 709.4.

Example 2

Synthesis of Compound (2): D-Phe-D-Phe-D-Leu-D-Orn-[4-Carboxymethyl-piperidine]-OH (SEQ ID NO: 1)

The compound was prepared according to the procedure described in the synthesis of compound (1). The variation was the substitution of Fmoc-4-carboxymethyl-piperidine (Chem-Impex International Inc.) for Fmoc-4-(2-aminoethyl)-1-carboxymethyl-piperazine dihydrochloride in the attachment to 2-Cl-Trt resin. Final purified peptide: amorphous powder, 123 mg in yield in a synthesis scale of 0.4 mmol. HPLC analysis: $t_R$=15.36 min, purity 100%, gradient 15% B to 35% B over 20 min; MS (M+H$^+$): expected molecular ion mass 665.4, observed 665.3.

Example 3

Synthesis of Compound (3): D-Phe-D-Phe-D-Nle-D-Arg-D-Pro-OH (SEQ ID NO: 2)

The compound was prepared according to the procedure described in the synthesis of compound (1). The amino acid derivatives used were Boc-D-Phe-OH, Fmoc-D-Phe-OH, Fmoc-D-Nle-OH, Fmoc-D-Arg(Pbf)-OH, and Fmoc-D-Pro-OH. Final purified peptide: amorphous powder, 140 mg in yield in a synthesis scale of 0.3 mmol. HPLC analysis: $t_R$=20.23 min, purity 99.7%, gradient 10% B to 30% B over 20 min; MS (M+H$^+$): expected molecular ion mass 679.4, observed 679.5.

Example 4

Synthesis of Compound (4): D-Phe-D-Phe-D-Leu-D-Orn-[(2S,4R)-4-Amino-pyrrolidine-2-carboxylic acid]-OH (SEQ ID NO: 1)

The compound was prepared according to the procedure described in the synthesis of compound (1). The variation was the substitution of Fmoc-(2S,4R)-4-amino-1-Boc-pyrrolidine-2-carboxylic acid (Chem-Impex International Inc.) for Fmoc-4-(2-aminoethyl)-1-carboxymethyl-piperazine dihydrochloride in the attachment to 2-Cl-Trt resin. Final purified peptide: amorphous powder, 294 mg in yield in a synthesis scale of 0.3 mmol. HPLC analysis: $t_R$=16.65 min, purity 99.4%, gradient 5% B to 25% B over 20 min; MS (M+H$^+$): expected molecular ion mass 652.4, observed 652.4.

Example 5

Synthesis of Compound (5): D-Phe-D-Phe-D-Leu-D-Orn-[(2S,4S)-4-Amino-pyrrolidine-2-carboxylic acid]-OH (SEQ ID NO: 1)

The compound was prepared according to the procedure described in the synthesis of compound (1). The variation was the substitution of Fmoc-(2S,4S)-4-amino-1-Boc-pyrrolidine-2-carboxylic acid (Chem-Impex International Inc.) for Fmoc-4-(2-aminoethyl)-1-carboxymethyl-piperazine dihydrochloride in the attachment to 2-Cl-Trt resin. Final purified peptide: amorphous powder, 285 mg in yield in a synthesis scale of 0.3 mmol. HPLC analysis: $t_R$=17.42 min, purity 99.5%, gradient 5% B to 25% B over 20 min; MS (M+H$^+$): expected molecular ion mass 652.4, observed 652.4.

Example 6

Synthesis of Compound (6): D-Phe-D-Phe-D-Leu-D-Orn-[omega(4-Aminopiperidine-4-carboxylic acid)]-OH (SEQ ID NO: 1)

The compound was prepared according to the procedure described in the synthesis of compound (1). The variation was the substitution of N-Boc-amino-(4-N-Fmoc-piperidinyl) carboxylic acid (PharmaCore) for Fmoc-4-(2-aminoethyl)-1-carboxymethyl-piperazine dihydrochloride in the attachment to 2-Cl-Trt resin. Final purified peptide: amorphous powder, 343 mg in yield in a synthesis scale of 0.3 mmol. HPLC analysis: $t_R$=16.82 min, purity 99.7%, gradient 5% B to 25% B over 20 min; MS (M+H$^+$): expected molecular ion mass 664.4, observed 664.3.

Example 7

Synthesis of Compound (7): D-Phe-D-Phe-D-Leu-D-Orn-[ω(D/L-2-Amino-3-(4-N-piperidinyl)propionic acid)]-OH (SEQ ID NO: 1)

The compound was prepared according to the procedure described in the synthesis of compound (1). The variation was the substitution of 2-N-Boc-amino-3-(N-Fmoc-4-piperidyl)propionic acid (PharmaCore) for Fmoc-4-(2-aminoethyl)-1-carboxymethyl-piperazine dihydrochloride in the attachment to 2-Cl-Trt resin. Final purified peptide: amorphous powder, 343 mg in yield in a synthesis scale of 0.3 mmol. HPLC analysis: $t_R$=16.82 min, purity 99.7%, gradient 5% B to 25% B over 20 min; MS (M+H$^+$): expected molecular ion mass 664.4, observed 664.3.

Example 8

Synthesis of Compound (8): D-Phe-D-Phe-D-Leu-D-Orn-[omega(D/L-piperazine-2-carboxylic acid)]-OH (SEQ ID NO: 1)

The compound was prepared according to the procedure described in the synthesis of compound (1). The variation was the substitution of $N^1$-Boc-$N^4$-Fmoc-piperazine-2-carboxylic acid (Chem-Impex International Inc.) for Fmoc-4-(2-aminoethyl)-1-carboxymethyl-piperazine dihydrochloride in the attachment to 2-Cl-Trt resin. Final purified peptide: amorphous powder, 200 mg in yield in a synthesis scale of 0.3 mmol. HPLC analysis: $t_R$=17.78 min, purity 99.9%, gradient 5% B to 25% B over 20 min; MS (M+H$^+$): expected molecular ion mass 652.4, observed 652.4.

Example 9

Synthesis of Compound (9): D-Phe-D-Phe-D-Leu-D-Orn-[Isonipecotic acid]-OH (SEQ ID NO: 1)

The compound was prepared according to the procedure described in the synthesis of compound (1). The variation was the substitution of Fmoc-isonipecotic acid (NeoMPS) for Fmoc-4-(2-aminoethyl)-1-carboxymethyl-piperazine dihydrochloride in the attachment to 2-Cl-Trt resin. Final purified peptide: amorphous powder, 125 mg in yield in a synthesis scale of 0.4 mmol. HPLC analysis: $t_R$=18.74 min, purity 99.3%, gradient 10% B to 30% B over 20 min; MS (M+H$^+$): expected molecular ion mass 651.4, observed 651.3.

Example 10

Synthesis of Compound (10): D-Phe-D-Phe-D-Leu-D-Orn-[N-(4-piperidinyl)-L-proline]-OH (SEQ ID NO: 1)

The compound was prepared according to the procedure described in the synthesis of compound (1). The variation was the substitution of N-(1-Fmoc-piperidin-4-yl)-L-proline (NeoMPS) for Fmoc-4-(2-aminoethyl)-1-carboxymethyl-piperazine dihydrochloride in the attachment to 2-Cl-Trt resin. Final purified peptide: amorphous powder, 18 mg in yield in a synthesis scale of 0.4 mmol. HPLC analysis: $t_R$=14.59 min, purity 100%, gradient 10% B to 30% B over 20 min; MS (M+H$^+$): expected molecular ion mass 720.4, observed 720.3.

Example 11

Synthesis of Compound (11): D-Phe-D-Phe-D-Leu-D-Orn-[homopiperazine amide] (SEQ ID NO: 1)

Synthesis was initiated from 0.3 mmol of the peptide intermediate, Cbz-D-Phe-D-Phe-D-Leu-D-Orn(Cbz)-[homopiperazine amide], which was prepared during the synthesis of compound (19). The peptide was hydrolyzed with a mixture of TMSOTf/TFA/m-cresol (10 ml, v/v/v=2:7:1) and the crude product was purified by preparative HPLC according to the procedure described in the synthesis of compound (19). Final purified peptide: amorphous powder, 225 mg in yield. HPLC analysis: $t_R$=16.43 min, purity 100%, gradient 2% B to 22% B over 20 min; MS (M+H$^+$): expected molecular ion mass 622.4, observed 622.4.

Example 12

Synthesis of Compound (12): D-Phe-D-Phe-D-Leu-D-Orn-[4-(4-piperidinyl)-butanoic acid]-OH (SEQ ID NO: 1)

The compound was prepared according to the procedure described in the synthesis of compound (1). The variation was the substitution of 4-(1-Fmoc-piperidin-4-yl)-butanoic acid (NeoMPS) for Fmoc-4-(2-aminoethyl)-1-carboxymethyl-piperazine dihydrochloride in the attachment to 2-Cl-Trt resin. Final purified peptide: amorphous powder, 474 mg in yield in a synthesis scale of 0.4 mmol. HPLC analysis: $t_R$=17.91 min, purity 100%, gradient 15% B to 35% B over 20 min; MS (M+H$^+$): expected molecular ion mass 693.4, observed 693.3.

Example 13

Synthesis of Compound (13): D-Phe-D-Phe-D-Leu-D-Orn-[4-(2-aminoethyl)-1-carboxymethyl-piperazine]-NH$_2$ (SEQ ID NO: 1)

Figure 2:
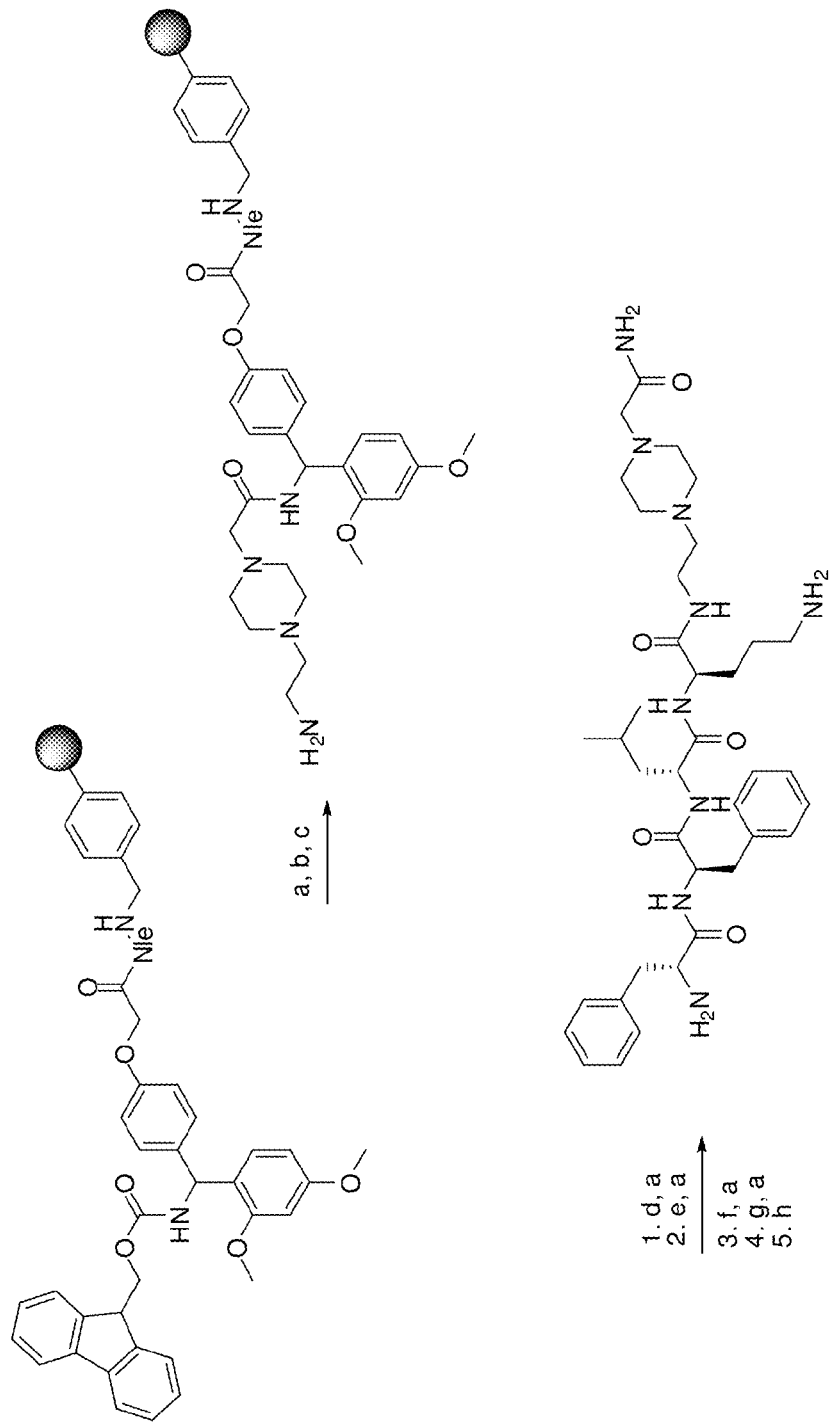
FIG. 2: Shows the general scheme used in the synthesis of compound (13): D-Phe-D-Phe-D-Leu-D-Orn-[4-(2-aminoethyl)-1-carboxymethylpiperazine]-NH$_2$ (SEQ ID NO: 1). Steps a-h were carried out with the following reactants or conditions: a) 25% piperidine, DMF; b) Fmoc-4-(2-aminoethyl)-1-carboxylmethyl-piperazine, HBTU, DIEA, DMF; c)

Synthesis was accomplished as shown in FIG. 2. The amino acid derivatives used were Boc-D-Phe-OH, Fmoc-D-Phe-OH, Fmoc-D-Leu-OH, Fmoc-D-Orn(Boc)-OH, and Fmoc-4-(2-aminoethyl)-1-carboxymethyl-piperazine dihydrochloride. The fully protected resin-bound peptide was synthesized on a SYMPHONY Multiple Synthesizer (Protein Technology Inc.) starting from Rink Amide AM resin (0.3 mmol; Novabiochem). The attachment of the first amino acid to the resin was achieved by treatment with a mixture of Fmoc-4-(2-aminoethyl)-1-carboxymethyl-piperazine dihydrochloride (0.48 g, 1 mmol; Chem-Impex International Inc.), HBTU (0.38 g, 1 mmol) and DIEA (0.53 mL, 3 mmol) in DMF (7 ml) at room temperature for 3 hours. The resin was washed with 3×DMF.

Subsequent peptide chain elongation was achieved by HBTU/DIEA mediated single couplings with a 3-fold excess of amino acid derivatives. The Fmoc group was removed by 25% piperidine in DMF. For cleavage, the final peptide resin was treated with a mixture of TFA/TIS/H$_2$O (15 ml, v/v/v=95:2.5:2.5) at room temperature for 90 minutes. The resin was filtered and washed with TFA. The filtrate was evaporated in vacuo and the crude peptide (0.1 g, D-Phe-D-Phe-D-Leu-D-Orn-[4-(2-aminoethyl)-1-carboxymethyl-piperazine]-NH$_2$) was precipitated from diethyl ether.

For purification, the above crude peptide (0.1 g) was dissolved in 0.1% TFA in H$_2$O (50 ml) and the solution was loaded onto an HPLC column and purified using a TFA buffer system (buffers A=0.1% TFA in H$_2$O and B=0.1% TFA in 60% ACN/40% H$_2$O). The compound was eluted with a linear gradient of buffer B, 25% B to 75% B over 30 min, $t_R$=38% B. The fractions with purity exceeding 97% were pooled, frozen, and dried on a lyophilizer to yield the purified peptide as a white amorphous powder (36 mg). HPLC analysis: $t_R$=16.59, purity 99.5%, gradient 2% B to 22% B over 20 min; MS (M+H$^+$): expected molecular ion mass 708.5, observed 708.3.

Example 14

Synthesis of Compound (14): D-Phe-D-Phe-D-Leu-D-Orn-[N-(4-piperidinyl)-L-proline]-NH$_2$ (SEQ ID NO: 1)

The compound was prepared according to the procedure described in the synthesis of compound (13). The variation was the substitution of N-(1-Fmoc-piperidin-4-yl)-L-proline (NeoMPS) for Fmoc-4-(2-aminoethyl)-1-carboxymethyl-piperazine dihydrochloride in the attachment to Rink Amide AM resin. Final purified peptide: amorphous powder, 14 mg in yield in a synthesis scale of 0.3 mmol. HPLC analysis: $t_R$=18.13 min, purity 91.7%, gradient 10% B to 30% B over 20 min; MS (M+H$^+$): expected molecular ion mass 719.5, observed 719.3.

Example 15

Synthesis of Compound (15): D-Phe-D-Phe-D-Leu-D-Orn-[4-Amino-1-carboxymethyl-piperidine]-NH$_2$ (SEQ ID NO: 1)

The compound was prepared according to the procedure described in the synthesis of compound (13). The variation was the substitution of Fmoc-4-amino-1-carboxymethyl-piperidine (NeoMPS) for Fmoc-4-(2-aminoethyl)-1-carboxymethyl-piperazine dihydrochloride in the attachment to Rink Amide AM resin. Final purified peptide: amorphous powder, 65 mg in yield in a synthesis scale of 0.3 mmol. HPLC analysis: $t_R$=16.74 min, purity 99.7%, gradient 2% B to 22% B over 20 min; MS (M+H$^+$): expected molecular ion mass 679.4, observed 679.3.

Example 16

Synthesis of Compound (16): D-Phe-D-Phe-D-Leu-D-Orn-[4-Amidinohomopiperazine amide] (SEQ ID NO: 1)

Synthesis was initiated from 0.2 mmol of the peptide intermediate, Cbz-D-Phe-D-Phe-D-Leu-D-Orn(Cbz)-[homopiperazine amide], which was prepared during the synthesis of compound (19). For guanylation of the homopiperazine at C-terminus, the peptide was treated with a solution of 1H-Pyrazole-1-carboxamidine hydrochloride (0.4 g, 3.0 mmol) and DIEA (0.5 ml, 6 mmol) in DMF (3 ml) overnight at room temperature. Acetic acid and H$_2$O were added to quench the reaction and the solution was frozen and dried on a lyophilizer to give the desired protected peptide, Cbz-DPhe-DPhe-DLeu-DOrn(Cbz)-[4-Amidinohomopiperazine amide] (0.2 mmol). The subsequent deprotection/hydrolysis and HPLC purification were carried out according to the procedure described in the synthesis of compound (19). Final purified peptide: amorphous powder, 74 mg in yield. HPLC analysis: t$_R$=10.10 min, purity 98.7%, gradient 10% B to 30% B over 20 min; MS (M+H$^+$): expected molecular ion mass 664.4, observed 664.5.

Example 17

Synthesis of Compound (17): D-Phe-D-Phe-D-Leu-D-Orn-[4-(4,5-dihydro-1H-imidazol-2-yl)homopiperazine amide] (SEQ ID NO: 1)

Synthesis was initiated from 0.2 mmol of the peptide intermediate, Cbz-D-Phe-D-Phe-D-Leu-D-Orn(Cbz)-[homopiperazine amide], which was prepared during the synthesis of compound (19). For guanylation of the homopiperazine at C-terminus, the peptide was treated with a solution of 2-Methylthio-2-imidazoline hydroiodide (730 mg, 3.0 mmol; Aldrich) and DIEA (0.5 ml, 6 mmol) in DMF (3 ml) for 4 days at room temperature. Acetic acid and H$_2$O were added to quench the reaction and the solution was frozen and dried on a lyophilizer to give the desired protected peptide, Cbz-D-Phe-D-Phe-D-Leu-D-Orn(Cbz)-[4-(4,5-dihydro-1H-imidazol-2-yl)homopiperazine amide] (0.2 mmol). The subsequent deprotection/hydrolysis and HPLC purification were carried out according to the procedure described in the synthesis of compound (19). Final purified peptide: amorphous powder, 46 mg in yield. HPLC analysis: t$_R$=10.89 min, purity 100%, gradient 10% B to 30% B over 20 min; MS (M+H$^+$): expected molecular ion mass 690.4, observed 690.5.

Example 18

Synthesis of Compound (18): D-Phe-D-Phe-D-Leu-D-Orn-[4-ethylhomopiperazine amide] (SEQ ID NO: 1)

Synthesis was initiated from 0.3 mmol of the peptide intermediate, Cbz-D-Phe-D-Phe-D-Leu-D-Orn(Cbz)-[homopiperazine amide], which was prepared during the synthesis of compound (19). For ethylation of the homopiperazine at C-terminus, the peptide was treated with a solution of iodoethane (0.4 mmol; Aldrich) and DIEA (0.5 ml, 6 mmol) in DMF (3 ml) for 1 day at room temperature. The subsequent deprotection/hydrolysis and HPLC purification were carried out according to the procedure described in the synthesis of compound (19). Final purified peptide: amorphous powder, 75 mg in yield. HPLC analysis: t$_R$=10.43 min, purity 98.4%, gradient 10% B to 30% B over 20 min; MS (M+H$^+$): expected molecular ion mass 650.4, observed 650.3.

Example 19

Synthesis of Compound (19): D-Phe-D-Phe-D-Leu-D-Orn-[4-(N-methyl)amidinohomopiperazine amide] (SEQ ID NO: 1)

See FIG. 3 for the general synthetic scheme used to prepare compound (19). The compound was prepared by guanylation of the homopiperazine at C-terminus of Cbz-D-Phe-D-Phe-D-Leu-D-Orn(Cbz)-[homopiperazine amide], which was synthesized according to the procedure described below.

The guanylation reagent S-Methyl-N-methylisothiourea hydroiodide was prepared by reacting 1,3-dimethyl-2-thiourea with methyl iodide in anhydrous methanol. See McKay, A. F.; Hatton, W. G. Synthesis of Cyclic Guanidino Acids. *J. Am. Chem. Soc.* (1955), 78, 1618-1620 and Kennedy, K. J., et al. A Facile Route to Cyclic and Acyclic Alkyl-Arginines. *Synthetic Communications*, (1998), 28, 741-746.

For synthesis of Cbz-D-Phe-D-Phe-D-Leu-D-Orn(Cbz)-[homopiperazine amide], the amino acid derivatives used were Z-D-Phe-OH, Fmoc-D-Phe-OH, Fmoc-D-Leu-OH, and Fmoc-D-Orn(Cbz)-OH. The fully protected resin bound peptide was synthesized manually starting from p-nitrophenylcarbonate Wang resin (5.0 g, 4.4 mmol; Novabiochem). The attachment of homopiperazine to the resin was achieved by mixing a solution of homopiperazine (8.7 g, 87 mmol; Acros Organics) in DCM (100 ml) overnight at room temperature. The resin was washed with 3×DMF and 3×DCM. The subsequent peptide chain elongation was achieved by HBTU/DIEA-mediated single couplings with a 3-fold excess of amino acid derivatives. The Fmoc group was removed by 25% piperidine in DMF. For cleavage, the final peptide resin was treated with a mixture of TFA/DCM (100 mL, v/v=1:1) at room temperature for 2 hours. The resin was filtered and washed with DCM. The filtrate was evaporated in vacuo and the residue was dissolved in 0.1% TFA in 60% ACN/40% H$_2$O. The solution was frozen, and dried on a lyophilizer to give the crude peptide intermediate Cbz-D-Phe-D-Phe-D-Leu-D-Orn(Cbz)-homopiperazine (4.4 g). For purification, the crude peptide (4.4 g) was divided into two portions and each portion was dissolved in 0.1% TFA in 30% ACN (100 ml). Each solution was loaded onto an HPLC column and purified using a TFA buffer system (buffers A=0.1% TFA in H$_2$O and B=0.1% TFA in 60% ACN/40% H$_2$O). The compound was eluted with a linear gradient of buffer B, 40% B to 100% B over 25 min, t$_R$=87% B. The fractions with purity exceeding 97% were pooled, frozen, and dried on a lyophilizer to yield the purified peptide intermediate as a white amorphous powder (3.0 g).

For guanylation of the homopiperazine at C-terminus, the above peptide intermediate (210 mg, 0.3 mmol) was treated with a mixture of S-Methyl-N-methylisothiourea hydroiodide (1.4 g, 6 mmol) and DIEA (1.0 mL, 12 mmol) in DMF (4 mL) at room temperature for 18 days. The mixture was evaporated in vacuo and the residue was dissolved in 0.1% TFA in 30% ACN/70% H$_2$O and the solution was loaded onto an HPLC column and purified using a TFA buffer system (buffers A=0.1% TFA in H$_2$O and B=0.1% TFA in 60% ACN/40% H$_2$O). The compound was eluted with a linear gradient of buffer B, 70% B to 100% B over 30 min, t$_R$=85% B. The fractions with purity exceeding 97% were pooled, frozen, and dried on a lyophilizer to yield the purified peptide intermediate, Cbz-D-Phe-D-Phe-D-Leu-D-Orn(Cbz)-[N-methylhomopiperazine-1-carboximidamide amide], as white amorphous powder (100 mg).

For final deprotection/hydrolysis, the above purified peptide (100 mg) was treated with a mixture of TMSOTf/TFA/m-cresol (10 ml, v/v/v=2:7:1) at room temperature for 2 hours. The mixture was evaporated in vacuo and the crude peptide (100 mg) was precipitated from diethyl ether.

For purification, the above crude peptide (100 mg) was dissolved in 0.1% TFA in H$_2$O (50 ml) and the solution was loaded onto an HPLC column and purified using TFA buffer system (buffers A=0.1% TFA in H$_2$O and B=0.1% TFA in 60% ACN/40% H$_2$O). The compound was eluted with a linear gradient of buffer B, 25% B to 75% B over 25 min, $t_R$=43% B. The fractions with purity exceeding 97% were pooled, frozen, and dried on a lyophilizer to yield the purified product as white a amorphous powder (53 mg). HPLC analysis: $t_R$=17.99 min, purity 99.4%, gradient 2% B to 22% B over 20 min; MS (M+H$^+$): expected molecular ion mass 678.4, observed 678.5.

Example 20

Synthesis of Compound (20): D-Phe-D-Phe-D-Leu-(δ-iPr)D-Orn-[omega(4-Aminopiperidine-4-carboxylic acid)]-OH The amino acid derivatives used were Boc-D-Phe-OH, Fmoc-D-Phe-OH, Fmoc-D-Leu-OH, Fmoc-D-Orn(Aloc)-OH, and N-Boc-amino-(4-N-Fmoc-piperidinyl) carboxylic acid. The fully protected resin bound peptide was synthesized manually starting from 2-Chlorotrityl chloride resin (0.8 mmol). The attachment of N-Boc-amino-(4-N-Fmoc-piperidinyl) carboxylic acid to resin and subsequent couplings were carried out according to the procedure described in the synthesis of compound (1). The assembled peptide resin, Boc-D-Phe-D-Phe-D-Leu-D-Orn-omega(4-Aminopiperidine-4-carboxylic acid)-[2-Cl-Trt resin], was treated with Pd(PPh$_3$)$_4$ (4.5 mmol; Aldrich) in a mixture of CHCl$_3$/AcOH/NMM (80 ml, v/v/v=37:2:1) under Argon atmosphere at room temperature for 3 h for Aloc removal. Subsequent N-isopropylation was carried out according the procedure described in the synthesis of compound (22). Final cleavage and preparative HPLC purification were accomplished according to the procedure described in the synthesis of compound (1). Final purified peptide: amorphous powder, 336 mg in yield. HPLC analysis: $t_R$=18.88 min, purity 98.9%, gradient 5% B to 25% B over 20 min; MS (M+H$^+$): expected molecular ion mass 708.4, observed 708.4.

Example 21

Synthesis of Compound (21): D-Phe-D-Phe-D-Leu-(δ-Me)D-Orn-[4-Amidinohomopiperazine amide] (SEQ ID NO: 1)

See the scheme shown in FIG. 3. The amino acid derivatives used were Z-D-Phe-OH, Fmoc-D-Phe-OH, Fmoc-D-Leu-OH, and Fmoc-D-Orn(Aloc)-OH. The fully protected resin bound peptide was synthesized manually starting from p-nitrophenylcarbonate Wang resin (5.0 g, 4.4 mmol; Novabiochem). The attachment of homopiperazine to the resin was achieved by mixing it with a solution of homopiperazine (8.7 g, 87 mmol; Acros Organics) in DCM (100 mL) overnight at room temperature. The resin was washed with DMF and DCM and dried in vacuo. The resulting homopiperazine carbamate Wang resin (5.1 g; homopiperazine-[carbamate Wang resin]) was split into several portions and a portion of 1.1 g (1 mmol) was used to continue the peptide synthesis. DIC/HOBt mediated single couplings were performed with a 3-fold excess of amino acid derivatives. The Fmoc group was removed with 25% piperidine in DMF. Upon completion of peptide chain elongation, the resin was treated with Pd(PPh$_3$)$_4$ (3.5 g, 3.0 mmol; Aldrich) in a mixture of CHCl$_3$/AcOH/NMM (60 ml, v/v/v=37:2:1) under Argon atmosphere at room temperature for 3 h for Aloc removal. The resin was washed with DMF and DCM and dried in vacuo. The resulting peptide resin (1.8 g; Z-D-Phe-D-Phe-D-Leu-D-Orn-homopiperazine-[carbamate Wang resin]) was split again and a portion of 0.9 g (0.5 mmol) was used for subsequent derivatization (N-methylation).

Methylation of the omega-amino function of D-Orn at Xaa$_4$ was carried out in three steps: (i) [o-NBS Protection]: The resin-bound peptide (0.5 mmol) was first treated with a solution o-NBS-Cl (0.4 g, 2 mmol) and collidine (0.7 ml, 5 mmol) in NMP (7 ml) at room temperature for 30 min. The resin was then washed with NMP. (ii) [N-Methylation]: The resin-bound o-NBS protected peptide was then reacted with a solution of 1,8-diazabicyclo[5.4.0]undec-7-ene (0.5 ml, 3 mmol) and dimethylsulfate (1.0 ml, 10 mmol; Aldrich) in NMP (7 ml) at room temperature for 5 min. The resin was then washed with NMP and the N-methylation process was repeated once. (iii) [o-NBS Deprotection]: The peptide resin was treated with a solution of mercaptoethanol (0.7 ml, 10 mmol) and 1,8-diazabicyclo[5.4.0]undec-7-ene (0.8 ml, 5 mmol) in NMP (7 ml) at room temperature for 5 min. The resin was then washed with NMP and the deprotection process was repeated once.

To protect the resulting N-methyl secondary amine of D-Orn at Xaa$_4$, the resin-bound methylated peptide was reacted with a solution of Z-OSu (6 mmol) in DMF (7 ml). The resin was washed with DMF and DCM and dried in vacuo. The peptide was then cleaved from the resin by treatment with a solution of TFA/DCM (15 ml, v/v=1:1) at room temperature for 2 hours. The resin was then filtered and washed with TFA. The filtrate was evaporated in vacuo and the crude peptide (0.5 mmol; Z-D-Phe-D-Phe-D-Leu-D-Orn(Me,Z)-[homopiperazine amide]) was obtained as an oil.

For guanylation of the homopiperazine at the C-terminus, a portion of the above peptide (0.3 mmol) was treated with a solution of 1H-Pyrazole-1-carboxamidine hydrochloride (0.4 g, 3.0 mmol) and DIEA (0.5 ml, 6 mmol) in DMF (3 ml) overnight at room temperature. Acetic acid and H$_2$O were added to quench the reaction and the solution was frozen and dried on a lyophilizer to give the desired protected peptide, Z-D-Phe-D-Phe-D-Leu-D-Orn(Me,Z)-[4-Amidinohomopiperazine amide] (0.3 mmol).

For final deprotection/hydrolysis, the above peptide (0.3 mmol) was treated with a mixture of TMSOTf/TFA/m-cresol (10 ml, v/v/v=2:7:1) at room temperature for 2 hours. The mixture was evaporated affording the crude peptide (0.3 mmol) as an oil. The preparative HPLC purification of the crude peptide was carried out according to the procedure as described in the synthesis of compound (1). Final purified peptide: amorphous powder, 183 mg in yield. HPLC analysis: $t_R$=17.12 min, purity 98.9%, gradient 2% B to 22% B over 20 min; MS (M+H$^+$): expected molecular ion mass 678.4, observed 678.5.

Example 22

Synthesis of Compound (22): D-Phe-D-Phe-D-Leu-(δ-iPr)D-Orn-[4-Amidinohomopiperazine amide] (SEQ ID NO: 3)

Synthesis was initiated from 0.9 g (0.5 mmol) of the peptide-resin: Z-D-Phe-D-Phe-D-Leu-D-Orn-homopiperazine-[carbamate Wang resin], which was prepared during the synthesis of compound (21) described above.

For isopropylation of the omega-amino function of D-Orn at Xaa$_4$, the peptide resin was treated with a mixture of sodium triacetoxyborohydride (3 mmol) and acetone (6 mmol) in TMOF (10 mL) over night at room temperature. The peptide resin was then treated with a solution of Z-OSu (6 mmol) in DMF (7 ml) for Z protection. The resin was washed with DMF and DCM and dried in vacuo. The peptide was then cleaved from the resin by treatment with a solution of TFA/DCM (15 ml, v/v=1:1) at room temperature for 2 hours. The resin was filtered and washed with TFA. The filtrate was evaporated in vacuo and the crude peptide (0.5 mmol; Z-D-Phe-D-Phe-D-Leu-D-Orn(iPr,Z)-[homopiperazine amide]) was obtained as an oil.

A portion of the above peptide (0.3 mmol) was continued for subsequent guanylation, cleavage and purification steps, which were carried out according to the procedure described in the synthesis of compound (21). Final purified peptide: amorphous powder, 166 mg in yield. HPLC analysis: $t_R$=18.71 min, purity 99.4%, gradient 2% B to 22% B over 20 min; MS (M+H$^+$): expected molecular ion mass 706.5, observed 706.5.

Example 23

Synthesis of Compound (23): D-Phe-D-Phe-D-Leu-(-Me)D-Orn-[homopiperazine amide] (SEQ ID NO: 4)

Synthesis was initiated from 0.2 mmol of the peptide intermediate, Z-D-Phe-D-Phe-D-Leu-D-Orn(Me,Z)-[homopiperazine amide], which was prepared during the synthesis of compound (21). The peptide was hydrolyzed with a mixture of TMSOTf/TFA/m-cresol (10 ml, v/v/v=2:7:1) and the crude product was purified by preparative HPLC according to the procedure described in the synthesis of compound (19). Final purified peptide: amorphous powder, 98 mg in yield. HPLC analysis: $t_R$=16.38 min, purity 99.6%, gradient 2% B to 22% B over 20 min; MS (M+H$^+$): expected molecular ion mass 636.4, observed 636.5.

Example 24

Synthesis of Compound (24): D-Phe-D-Phe-D-Leu-(6-iPr)D-Orn-[homopiperazine amide] (SEQ ID NO: 3)

Synthesis was initiated from 0.2 mmol of the peptide intermediate, Z-D-Phe-D-Phe-D-Leu-D-Orn(iPr,Z)-[homopiperazine amide], which was prepared during the synthesis of compound (22). The peptide was hydrolyzed with a mixture of TMSOTf/TFA/m-cresol (10 ml, v/v/v=2:7:1) and the crude product was purified by preparative HPLC according to the procedure described in the synthesis of compound (19). Final purified peptide: amorphous powder, 87 mg in yield. HPLC analysis: $t_R$=18.41 min, purity 100%, gradient 2% B to 22% B over 20 min; MS (M+H$^+$): expected molecular ion mass 664.5, observed 664.5.

Confirmation of structures of synthetic peptide amides:

Table I shows the calculated molecular weight of the molecular ion, MH$^+$ for each compound and the actual molecular weight observed by mass spectrometry. Also shown is the type of synthetic phase used in the synthesis of each compound: solid phase, or mixed; and the type of resin used in the synthesis, whether a 2-chlorotrityl "2-Cl-Trt" resin, a hydrazinobenzoyl "hydrazine" resin, Rink AM or a p-nitrophenyl-carbonate (Wang) "carbonate" resin. The figure showing the relevant synthetic scheme for the synthesis of each compound is shown in the last column.

TABLE I

Synthesis and Confirmation of Compound Structures

| COMPOUND | CALC'D MW | OBSERVED MW | SYNTH PHASE | RESIN | FIGURE |
|---|---|---|---|---|---|
| 1 | 709.4 | 709.4 | solid | 2-Cl-Trt | 1 |
| 2 | 665.4 | 665.3 | solid | 2-Cl-Trt | 1 |
| 3 | 679.4 | 679.5 | solid | 2-Cl-Trt | 1 |
| 4 | 652.4 | 652.4 | solid | 2-Cl-Trt | 1 |
| 5 | 652.4 | 652.4 | solid | 2-Cl-Trt | 1 |
| 6 | 666.4 | 666.3 | solid | 2-Cl-Trt | 1 |
| 7 | 694.4 | 694.4 | solid | 2-Cl-Trt | 1 |
| 8 | 652.4 | 652.4 | solid | 2-Cl-Trt | 1 |
| 9 | 651.4 | 651.3 | solid | 2-Cl-Trt | 1 |
| 10 | 720.4 | 720.6 | solid | 2-Cl-Trt | 1 |
| 11 | 622.4 | 622.4 | solid | Carbonate | 2 |
| 12 | 693.4 | 693.3 | solid | 2-Cl-Trt | 1 |
| 13 | 708.3 | 708.3 | solid | Rink AM | 2 |
| 14 | 719.5 | 719.3 | solid | Rink AM | 2 |
| 15 | 679.4 | 679.3 | solid | Rink AM | 2 |
| 16 | 664.4 | 664.5 | mixed | Carbonate | 3 |
| 17 | 690.4 | 690.5 | mixed | Carbonate | 3 |
| 18 | 650.4 | 650.3 | mixed | Carbonate | 3 |
| 19 | 678.4 | 678.5 | mixed | Carbonate | 3 |
| 20 | 708.4 | 708.4 | solid | 2-Cl-Trt | 1 |
| 21 | 678.4 | 678.5 | mixed | Carbonate | 3 |
| 22 | 706.5 | 706.5 | mixed | Carbonate | 3 |
| 23 | 636.4 | 636.5 | solid | Carbonate | 3 |
| 24 | 664.5 | 664.5 | solid | Carbonate | 3 |

Example 25

Synthesis of Compound (25): D-Phe-D-Phe-D-Leu-D-Lys-[1,3-dioxolan-2-yl)methanamine amide] (SEQ ID NO: 5)

These syntheses were carried out according to the scheme shown in FIG. 4. The intermediates described below correspond to those shown in FIG. 4. To a suspension of Boc-D-Phe-OH intermediate I-1 (7.96 g, 30.0 mmol), D-Leu-OBn p-TsOH intermediate I-2 (11.80 g, 30.0 mmol), HOBt monohydrate (4.46 g, 33.0 mmol) and DIEA (8.53 g, 66.0 mmol) in anhydrous THF (250 mL) cooled in an ice-water bath was added EDCI (6.33 g, 33.0 mmol) in four portions over 20 minutes with 5 minutes between each addition. The suspension was stirred overnight from a starting temperature of 0° C. to room temperature. After evaporation of THF, the residue was dissolved in ethyl acetate and washed sequentially with 10% citric acid, saturated NaHCO$_3$ and water. The organic phase was dried over sodium sulfate and evaporated under reduced pressure. The residue was dissolved in DCM, passed through a silica gel plug and eluted with 20% ethyl acetate in hexanes. The eluant was evaporated to give the pure product, Boc-D-Phe-D-Leu-OBn, intermediate I-3 (12.40 g, 88%) as a clear oil. LC-MS: m/z=469 (M+H).

Intermediate I-3 (12.40 g, 26.5 mmol) was dissolved in DCM (50 mL). TFA (25 mL) was added and the solution was stirred at room temperature for 2 hours. After evaporation of DCM and TFA, the residue was azeotroped with toluene twice to give the TFA salt of D-Phe-Leu-OBn, intermediate I-4. This crude dipeptide was suspended in THF, to which Boc-D-Phe-OH (6.36 g, 24 mmol), HOBt monohydrate (4.04 g, 26.4 mmol) and DIEA (8.7 mL, 50.0 mmol) was added at 0° C. EDCI (6.33 g, 6.4 mmol) was added in four portions over 20 minutes with 5 minutes between each addition. The suspension was stirred from 0° C. to room temperature overnight. After evaporation of THF, the residue was dissolved in ethyl acetate and washed sequentially with 10% citric acid, saturated NaHCO$_3$ and water. The organic phase was dried over sodium sulfate and evaporated under reduced pressure. The residue was recrystalized from 400 mL acetone/hexanes (1:3) to give 9.1 g pure product. The mother liquor was evaporated and again recrystalized from acetone/hexanes (1:3) to give 2.0 g product. The total yield was 11.1 g (68% for two steps). LC-MS: m/z=616 (M+H).

In a flask flushed with nitrogen was added wet palladium on carbon (1.8 g) and a solution of Boc-D-Phe-D-Phe-D-Leu-OBn, intermediate I-5 (11.1 g, 18.05 mmol) in methanol (50 mL). The mixture was stirred under a hydrogen balloon overnight. After filtration through celite, methanol was evaporated under reduced pressure. The residue was dissolved in acetone (20 mL) and slowly added to 500 mL water with 25 mL of 1N HCl under vigorous stirring. Pure product Boc-D-Phe-D-Phe-D-Leu-OH, intermediate I-6 was obtained by filtration 9.4 g (99%). LC-MS: m/z=526 (M+H).

To a solution of intermediate I-6 (2.06 g, 3.90 mmol), D-Lys(Boc)-OAll hydrochloride (1.26 g, 3.90 mmol) and DIEA (1.7 ml, 9.8 mmol) in DMF was added TBTU (1.56 g, 4.88 mmol) in three portions over 15 min at 0° C. After stirring overnight from a starting temperature of 0° C. to room temperature, DMF was evaporated under high vacuum. The crude reaction mixture was precipitate in 400 ml ice water and filtered to collect the precipitate, Boc-D-Phe-D-Phe-D-Leu-D-Lys(Boc)-OAll intermediate I-7 (2.60 g), which was used without further purification for the next step.

To a solution of intermediate I-7 (2.60 g, 3.3 mmol) in MeCN (75 mL) was added pyrrolidine (1.1 ml, 13.3 mmol) and palladium tetrakis(triphenylphosphine) (400 mg, 0.35 mmol) at 0° C. The reaction mixture was stirred at room temperature for 3 hours and evaporated to dryness. The residue was purified by reverse phase column chromatography with 30% MeCN/water to 90% MeCN/water to give the pure acid, intermediate I-8 (2.0 g, 80%) after evaporation of acetonitrile/water. LC-MS: m/z=754 (M+H).

To a solution of the acid, intermediate I-8 (150 mg, 0.20 mmol), the amine $HNR_aR_b$, (1,3-dioxolan-2yl)methanamine (31 mg, 0.30 mmol) and DIEA (175 ul, 1.0 mmol) in DMF (5 mL) was added HBTU (113 mg, 3.0 mmol) at 0° C. After stirring overnight from a starting temperature of 0° C. to room temperature, DMF was evaporated under reduced pressure. The residue was stirred with 4N HCl in 1,4-dioxane (2.0 mL) at room temperature for 1 hour. After removal of dioxane, the residue was dissolved in water and purified by reverse phase column chromatography with a gradient of 10% MeCN/water to 60% MeCN/water in 30 minutes to give pure product, compound (25) (44 mg, 44% yield for the two steps) after evaporation of solvent. LC-MS: m/z=639 (M+H).

Example 26

Synthesis of Compound (26): D-Phe-D-Phe-D-Leu-D-Lys-[2-(piperazin-1-yl)pyrimidine amide] (SEQ ID NO: 5)

Compound (26) was prepared essentially as described in Example 25, except that 2-(piperazin-1-yl)pyrimidine was used in the amide coupling step. LC-MS: m/z=700 (M+H).

Example 27

Synthesis of Compound (27): D-Phe-D-Phe-D-Leu-D-Lys-[2-(piperazin-1-yl)pyrazine amide] (SEQ ID NO: 5)

Compound 27 was prepared essentially as described in Example 25, except that 2-(piperazin-1-yl)pyrazine was used in the amide coupling step. LC-MS: m/z=700 (M+H).

Example 28

Synthesis of Compound (28): D-Phe-D-Phe-D-Leu-D-Lys-[1-(pyridin-2-yl)piperazine amide] (SEQ ID NO: 5)

Compound (28) was prepared essentially as described in Example 25, except that 1-(pyridin-2-yl)piperazine was used in the amide coupling step. LC-MS: m/z=699 (M+H).

Example 29

Synthesis of Compound (29): D-Phe-D-Phe-D-Leu-D-Lys-[2-(piperazin-1-yl)thiazole amide] (SEQ ID NO: 5)

Compound 29 was prepared essentially as described in Example 25, except that 2-(piperazin-1-yl) thiazole was used in the amide coupling step. LC-MS: m/z=705 (M+H).

Example 30

Synthesis of Compound (30): D-Phe-D-Phe-D-Leu-D-Lys-[N,N-dimethylpiperazine-1-sulfonamide amide] (SEQ ID NO: 5)

Compound 30 was prepared essentially as described in Example 25, except that N,N-dimethyl-piperazine-1-sulfonamide was used in the amide coupling step. LC-MS: m/z=729 (M+H).

Example 31

Synthesis of Compound (31): D-Phe-D-Phe-D-Leu-D-Lys-[1-(methylsulfonyl)piperazine amide] (SEQ ID NO: 5)

Compound 31 was prepared essentially as described in Example 25, except that 1-(methylsulfonyl)piperazine was used in the amide coupling step. LC-MS: m/z=700 (M+H).

Example 32

Synthesis of Compound (32): D-Phe-D-Phe-D-Leu-D-Lys-[1-(phenylsulfonyl)piperazine amide] (SEQ ID NO: 5)

Compound 32 was prepared essentially as described in Example 25, except that 1-(phenylsulfonyl) piperazine was used in the amide coupling step. LC-MS: m/z=762 (M+H).

Example 33

Synthesis of Compound (33): D-Phe-D-Phe-D-Leu-D-Lys-[phenyl(piperazin-1-yl)methanone amide] (SEQ ID NO: 5)

Compound 33 was prepared essentially as described in Example 25, except that phenyl(piperazin-1-yl)methanone was used in the amide coupling step. LC-MS: m/z=726 (M+H).

Example 34

Synthesis of Compound (34): D-Phe-D-Phe-D-Leu-D-Lys-[thiolmorpholine-1,1-dioxide amide] (SEQ ID NO: 5)

Compound 34 was prepared essentially as described in Example 25, except that thiolmorpholine-1,1-dioxide was used in the amide coupling step. LC-MS: m/z=671 (M+H).

Example 35

Synthesis of Compound (35): D-Phe-D-Phe-D-Leu-D-Lys-[6-trifluoromethyl-3-aminomethyl pyridine amide] (SEQ ID NO: 5)

Compound 35 was prepared essentially as described in Example 25, except that 6-trifluoromethyl-3-aminomethylpyridine was used in the amide coupling step. LC-MS: m/z=712 (M+H).

Example 36

Synthesis of Compound (36): D-Phe-D-Phe-D-Leu-D-Lys-N-methyl-1-(tetrahydro-2H-pyran-4-yl) methanamine amide (SEQ ID NO: 5)

Compound 36 was prepared essentially as described in Example 25, except that (tetrahydro-2H-pyran-4-yl)methanamine was used in the amide coupling step. LC-MS: m/z=651 (M+H).

Example 37

Synthesis of Compound (37): D-Phe-D-Phe-D-Leu-D-Lys-[5-(aminomethyl)-1H-benzo[d]imidazol-2 (3H)-one amide] (SEQ ID NO: 5)

Compound (37) was prepared essentially as described in Example 25, except that 5-(aminomethyl)-1H-benzo[d]imidazol-2(3H)-one was used in the amide coupling step. LC-MS: m/z=699 (M+H).

Example 38

Synthesis of Compound (38): D-Phe-D-Phe-D-Leu-D-Lys-N-methyl-1-(5-methylpyrazin-2-yl)-methanamine amide) (SEQ ID NO: 5)

Compound 38 was prepared essentially as described in Example 25, except that (5-methyl-pyrazin-2-yl)-methanamine was used in the amide coupling step. LC-MS: m/z=659 (M+H).

Example 39

Synthesis of Compound (39)

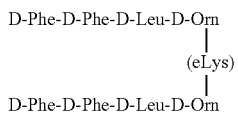

See the general scheme of FIG. 5 for the synthesis of compound (40). The amino acid derivatives used were Boc-D-Phe-OH, Fmoc-D-Phe-OH, Fmoc-D-Leu-OH, Boc-D-Leu-OH, Fmoc-D-Orn(Boc)-OH, and Fmoc-Lys(Dde)-OH. The fully protected resin bound peptide was synthesized manually starting from 2-Chlorotrityl chloride resin (0.3 mmol; Peptide International). The attachment of the first amino acid to the resin was achieved by treatment with a mixture of Fmoc-Lys(Dde)-OH (0.29 g, 0.5 mmol; Novabiochem) and DIEA (0.35 mL, 2 mmol) in DCM (7 ml) at room temperature for 4 hours. The resin was washed with 3×DCM/MeOH/DIEA (v/v/v=17:2:1) and then treated with 25% piperidine in DMF for Fmoc removal. The subsequent peptide chain elongation was achieved by PyBOP/DIEA mediated single couplings with a 3-fold excess of amino acid derivatives, Fmoc-D-Orn(Boc)-OH and Boc-D-Leu-OH. The resulting peptide resin, Boc-D-Leu-D-Orn(Boc)-Lys(Dde)-[2-Cl-Trt resin], was treated with 4% hydrazine in DMF three times for 3 min each to remove Dde. The subsequent peptide chain elongation was achieved by PyBOP/DIEA mediated single couplings with a 3-fold excess of amino acid derivatives, Fmoc-D-Orn(Boc)-OH, Fmoc-D-Leu-OH, Fmoc-D-Phe-OH, and Boc-D-Phe-OH. The Fmoc group was removed with 25% piperidine in DMF. The fully assembled peptide was cleaved from the resin by treatment with a mixture of TFA/TIS/H2O (15 ml, v/v/v=95:2.5:2.5) at room temperature for 90 min. The resin was filtered and washed with TFA. The filtrate was evaporated in vacuo and the crude peptide (0.3 mmol; D-Phe-D-Phe-D-Leu-D-Orn-[eLys(D-Orn-D-Leu-H)]-OH) was precipitated from diethyl ether.

For purification, the crude peptide (0.3 mmol) was dissolved in 2% acetic acid in H$_2$O (50 ml) and the solution was loaded onto an HPLC column and purified using TEAP buffer system with a pH 5.2 (buffers A=TEAP 5.2 and B=20% TEAP 5.2 in 80% ACN). The compound was eluted with a linear gradient of buffer B, 10% B to 40% B over 60 min. Fractions with purity exceeding 95% were pooled and the resulting solution was diluted with two volumes of water. The diluted solution was then loaded onto an HPLC column for salt exchange and further purification with a TFA buffer system (buffers A=0.1% TFA in H$_2$O and B=0.1% TFA in 80% ACN/20% H$_2$O) and a linear gradient of buffer B, 2% B to 75% B over 25 min. Fractions with purity exceeding 97% were pooled, frozen, and dried on a lyophilizer to yield the purified peptide as white amorphous powder (396 mg). HPLC analysis: t$_R$=13.63 min, purity 99.7%, gradient 10% B to 30% B over 20 min; MS (M+H$^+$): expected molecular ion mass 895.5, observed 895.6.

Example 40

Synthesis of Compound (40)

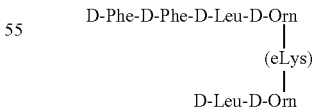

The compound was prepared according to the procedure described in the synthesis of compound (39) above. The variation was an additional amino acid residue D-Phe in the peptide resin intermediate, Boc-D-Phe-D-Leu-D-Orn(Boc)-Lys(Dde)-[2-Cl-Trt resin], The resin intermediate was prepared by attachment of Fmoc-Lys(Dde)-OH to 2-Chlorotrityl chloride resin followed by Fmoc removal and couplings of amino acid derivatives Fmoc-D-Orn(Boc)-OH, Fmoc-D-

Leu-OH, and Boc-D-Phe-OH. Final purified peptide: amorphous powder, 508 mg in yield in a synthesis scale of 0.3 mmol. HPLC analysis: $t_R$=18.90 min, purity 100%, gradient 10% B to 30% B over 20 min; MS (M+H$^+$): expected molecular ion mass 1042.4, observed 1042.7.

Example 41

Synthesis of Compounds (41)-(52)

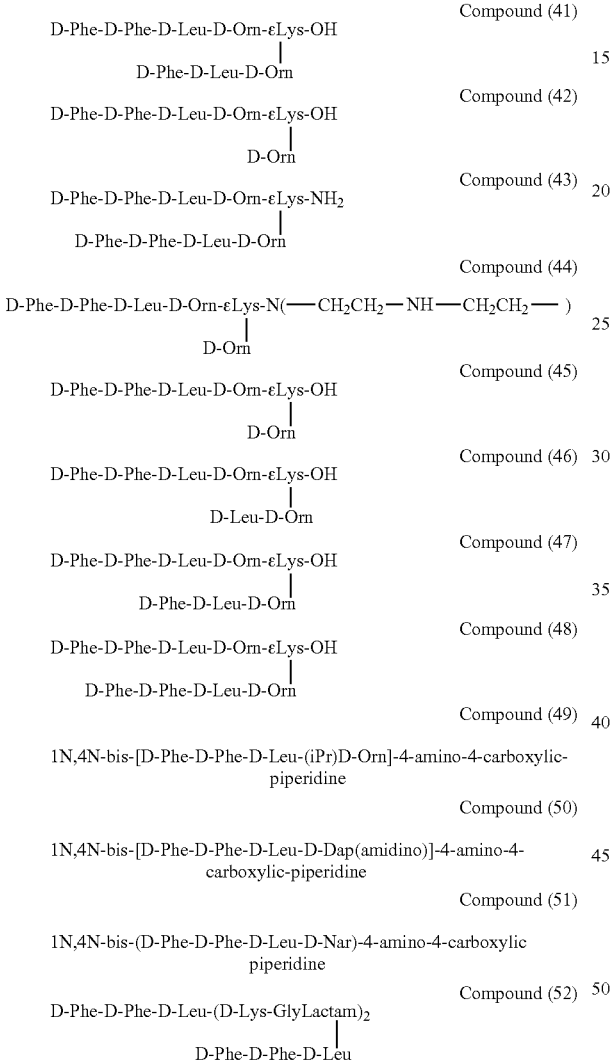

These compounds, (41)-(52) listed above, can be synthesized according to the general schemes shown in FIGS. 5, 6 and 7 by methods analogous to those used in the synthesis of compounds (39) and (40) described in detail above.

Example 42

Synthesis of Compound (53) D-Phe-D-Phe-D-Leu-D-Orn-[R/S-2-carboxymorpholine]-OH (SEQ ID NO: 1)

See the scheme of FIG. 8. The amino acid derivatives used were Boc-D-Phe-OH, Fmoc-D-Phe-OH, Fmoc-D-Leu-OH, Fmoc-D-Orn(Boc)-OH, and (R,S)-Fmoc-2-carboxymorpholine. The fully protected resin bound peptide was synthesized on a SYMPHONY Multiple Synthesizer (Protein Technology Inc.) starting from 2-Chlorotrityl chloride resin (0.4 mmol; Novabiochem). The attachment of the first amino acid to the resin was achieved by treatment with a mixture of (R,S)-Fmoc-2-carboxymorpholine (0.18 g, 0.5 mmol; NeoMPS) and DIEA (0.35 mL, 2 mmol) in DCM (7 ml) at room temperature for 4 hours. The resin was washed with 3× DCM/MeOH/DIEA (v/v/v=17:2:1) and 3×DCM. The subsequent peptide chain elongation was achieved by HBTU/DIEA mediated single couplings with a 3-fold excess of amino acid derivatives. The Fmoc group was removed by 25% piperidine in DMF. For cleavage, the final peptide resin was treated with a mixture of TFA/TIS/H2O (15 ml, v/v/v=95:2.5:2.5) at room temperature for 90 min. The resin was filtered and washed with TFA. The filtrate was evaporated in vacuo and the crude peptide (0.15 g, DPhe-DPhe-DLeu-DOrn-[R/S-2-carboxymorpholine]-OH) was precipitated from diethyl ether.

For purification, the above crude peptide (0.15 g) was dissolved in 0.1% TFA in H$_2$O (50 ml) and the solution was loaded onto an HPLC column and purified using TFA buffer system (buffers A=0.1% TFA in H$_2$O and B=0.1% TFA in 60% ACN/40% H$_2$O). The compound was eluted with a linear gradient of buffer B, 25% B to 75% B over 30 min, $t_R$=45% B. The fractions with purity exceeding 97% were pooled, frozen, and dried on a lyophilizer to give the purified peptide as white amorphous powder (84 mg). The compound was a mixture of diastereoisomers as no attempt was made to separate the two isomers, DPhe-DPhe-DLeu-DOrn-[R-2-carboxymorpholine]-OH and DPhe-DPhe-DLeu-DOrn-[S-2-carboxymorpholine]-OH. HPLC analysis: $t_R$=16.93 min (49.6%) and 17.34 min (50.4%), combined purity 100%, gradient 10% B to 30% B over 20 minutes.

FIG. 9 shows the general chemical scheme used in the synthesis of compound (53)

(SEQ ID NO: 1)::

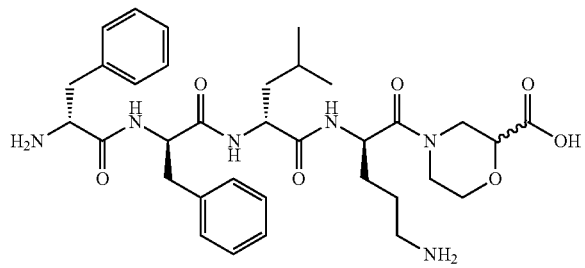

D-Phe-D-Phe-D-Leu-D-Orn-[R/S-2-carboxymorpholine]-OH

Example 43

Synthesis of Compounds (54)-(66)

Compounds (54)-(66) can be prepared by well known synthetic methods. For instance, compound (40), see below, can be prepared according to the chemical synthesis scheme of FIG. 9.

(SEQ ID NO: 1):

Compound (54)

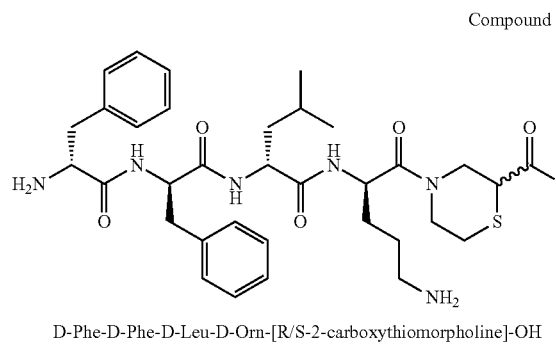

D-Phe-D-Phe-D-Leu-D-Orn-[R/S-2-carboxythiomorpholine]-OH

FIG. 9 shows the general chemical scheme used in the synthesis of compound (55).

(SEQ ID NO: 1)

Compound (55)

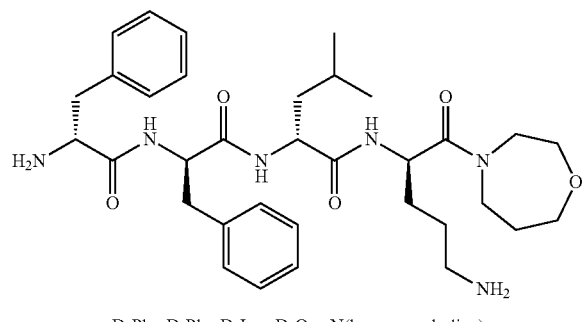

D-Phe-D-Phe-D-Leu-D-Orn-N(homomorpholine)

(SEQ ID NO: 1)

Compound (56)

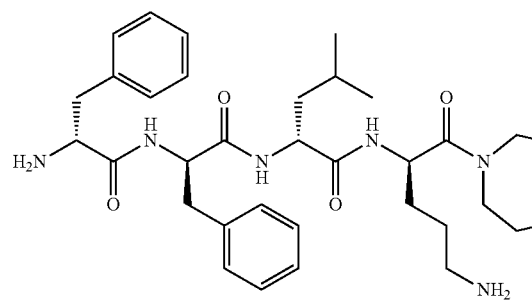

D-Phe-D-Phe-D-Leu-D-Orn-N(homothiomorpholine)

(SEQ ID NO: 8)

Compound (57)

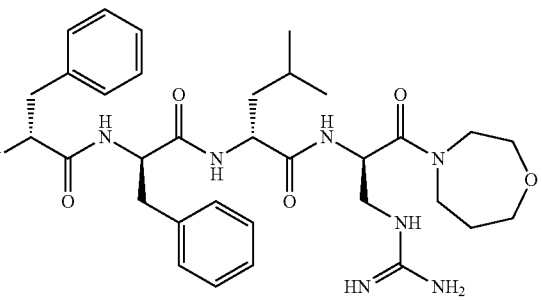

D-Phe-D-Phe-D-Leu-D-Dap(amidino)-[homomorpholine amide]

(SEQ ID NO: 8)

Compound (58)

D-Phe-D-Phe-D-Leu-D-Dap(amidino)-[homothiomorpholine amide]

(SEQ ID NO: 8)

Compound (59)

D-Phe-D-Phe-D-Nle-D-Dap(amidino)-[homomorpholine amide]

(SEQ ID NO: 8)

Compound (60)

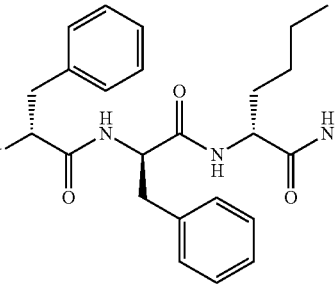

D-Phe-D-Phe-D-Nle-D-Dap(amidino)-[homothiomorpholine amide]

(SEQ ID NO: 7)

Compound (61)

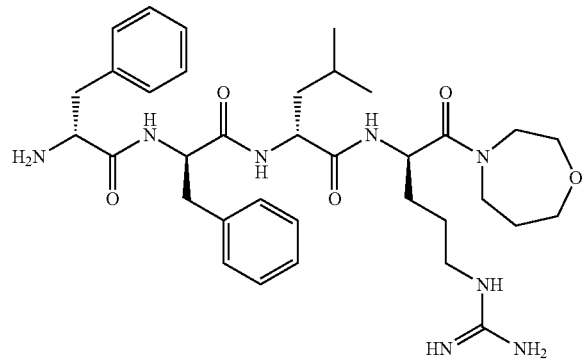

D-Phe-D-Phe-D-Leu-D-Arg-[homomorpholine amide]

(SEQ ID NO: 7)

Compound (62)

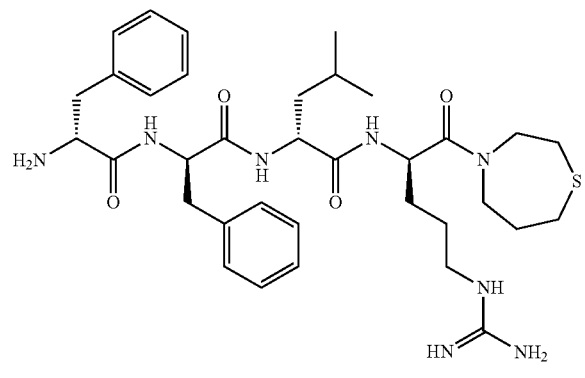

D-Phe-D-Phe-D-Leu-D-Arg-[homothiopiperazine amide]

(SEQ ID NO: 4)

Compound (63)

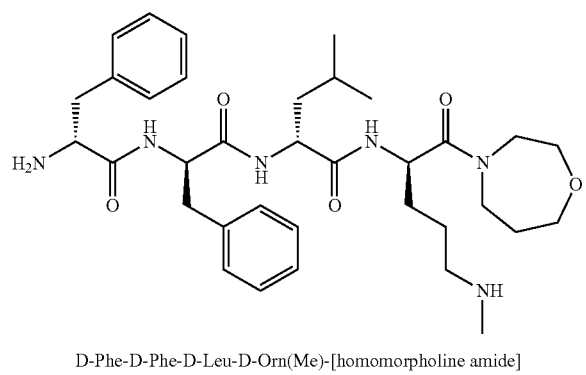

D-Phe-D-Phe-D-Leu-D-Orn(Me)-[homomorpholine amide]

(SEQ ID NO: 4)

Compound (64)

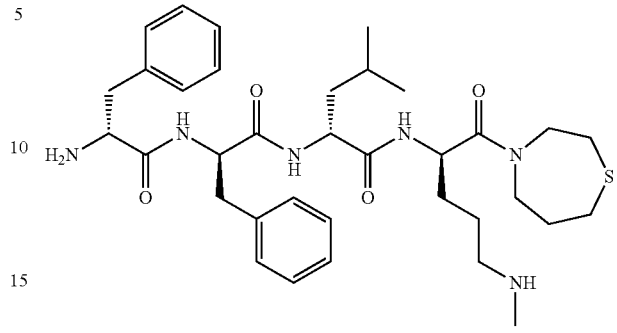

D-Phe-D-Phe-D-Leu-D-Orn(Me)-[homothiomorpholine amide]
(SEQ ID NO: 3)

Compound (65)

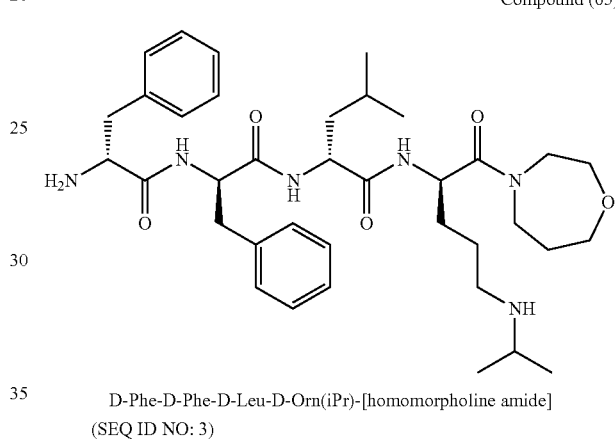

D-Phe-D-Phe-D-Leu-D-Orn(iPr)-[homomorpholine amide]
(SEQ ID NO: 3)

Compound (66)

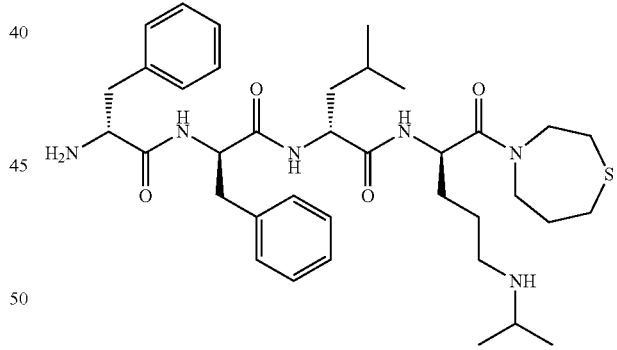

D-Phe-D-Phe-D-Leu-D-Orn(iPr)-[homothiomorpholine amide]

Example 44

Inhibition of cAMP Production by Stimulation of Endogenous Mouse Kappa-Opioid Receptor in R1.G1 Cells Potency of the synthetic peptide amides as kappa-opioid receptor agonists was determined by measuring the inhibition of forskolin-stimulated adenylate cyclase activity. R1.G1 cells (a mouse thymoma cell line that expresses only the kappa-opioid receptor and no other opioid receptor subtype) were first exposed to forskolin (to induce cAMP) plus the synthetic peptide amide at the test concentration. After incubation, the cAMP level in the challenged R1.G1 cells was determined using a time resolved fluorescence resonance energy transfer (TR-FRET)-based cAMP immunoassay (LANCE™, Perkin Elmer). The detailed method is described below:

Mouse R1.G1 cells (ATCC, Manassas, Va.) were grown in suspension in high glucose-DMEM (Dulbecco's Modified Eagle's Medium, Cellgro, Herndon, Va.) containing 10% horse serum and 2% glutaMax (Invitrogen, Carlsbad. Calif.) without added antibiotics. On the day of the experiment, cells were spun at 1,000 rpm for 5 minutes at room temperature and then washed once with HBSS (HEPES Buffered Saline Solution, Invitrogen, Carlsbad, Calif.). Cells were then spun again and resuspended in stimulation buffer (HBSS with 0.05% FAF-BSA (Fatty acid-free bovine serum albumin, Roche Applied Science, Indianapolis, Ind.), 5 mM HEPES) to 2 million cells per ml. Antibody supplied with the LANCE™ cAMP immunoassay kit was then added to the cells according to the manufacturer's instructions, and 12,000 cells per well were then added to the wells containing forskolin to a predetermined fixed final concentration (typically about 2.5 uM) and the previously determined amount of the synthetic peptide amide to be tested.

The synthetic peptide amides were tested in a range of concentrations to determine potency. Cells were incubated with the synthetic peptide amide plus forskolin for about 20 minutes at room temperature. After incubation, cells are lysed by adding 12 ul of detection mix as supplied with the LANCE™ kit, followed by incubation for one hour at room temperature. Time resolved fluorescence was read using a 330-380 nm excitation filter, a 665 nm emission filter, dichroic mirror 380, and Z=1 mm. A standard curve for cAMP concentration in this assay permitted determination of the amount of cAMP present in each well. A curve was produced by plotting synthetic peptide amide concentration against cAMP levels in the test cells, and subjected to non-linear regression using a four-parameter curve fitting algorithm to calculate the $EC_{50}$, the concentration of the synthetic peptide amide required to produce 50% of the maximal suppression of cAMP production by the synthetic peptide amide.

Example 45

Confirmation of Potency of the Synthetic Peptide Compounds on the Human Kappa Opioid Receptor Human Embryonic Kidney cells (HEK-293 cells, ATCC, Manassas, Va.) in 100 mm dishes were transfected with transfection reagent, Fugene6 (Roche Molecular Biochemicals) and DNA constructs in a 3.3 to 1 ratio. The DNA constructs used in the transfection were as follows: (i) an expression vector for the human kappa opioid receptor, (ii) an expression vector for a human chimeric G-protein, and (iii) a luciferase reporter construct in which luciferase expression is induced by the calcium sensitive transcription factor NFAT.

The expression vector containing the human kappa opioid receptor was constructed as follows: The human OPRK1 gene was cloned from human dorsal root ganglion total RNA by PCR and the gene inserted into expression vector pcDNA3 (Invitrogen, Carlsbad, Calif.) to construct human OPRK1 mammalian expression vector pcDNA3-hOPRK1.

To construct the human chimeric G-protein expression vector, the chimeric G-protein Gαqi5 was first constructed by replacing the last 5 amino acids of human Gαq with the sequence of the last 5 amino acids of Gαi by PCR. A second mutation was introduced to this human Gαqi5 gene at amino acid position 66 to substitute a glycine (G) with an aspartic acid (D) by site-directed mutagenesis. This gene was then subcloned into a mammalian expression vector pcDNA5/FRT (Invitrogen) to yield the human chimeric G-protein expression vector, pcDNA5/FRT-hGNAq-G66D-i5.

To prepare the luciferase reporter gene construct, synthetic response elements including 3 copies of TRE (12-O-tetradecanoylphorbol-13-acetate-responsive elements) and 3 copies of NFAT (nuclear factor of activated T-cells) were incorporated upstream of a c-fos minimal promoter. This response element and promoter cassette was then inserted into a luciferase reporter gene vector pGL3-basic (Promega) to construct the luciferase reporter gene plasmid construct pGL3b-3TRE-3NFAT-cfos-Luc.

The transfection mixture for each plate of cells included 6 micrograms pcDNA3-hOPRK1, 6 micrograms of pcDNA5/FRT-hGNAq-G66D-i5, and 0.6 micrograms of pGL3b-3TRE-3NFAT-cfos-Luc. Cells were incubated for one day at 37° C. in a humidified atmosphere containing 5% $CO_2$ following transfection, and plated in opaque 96-well plates at 45,000 cells per well in 100 microliters of medium. The next day, test and reference compounds were added to the cells in individual wells. A range of concentrations of test compounds was added to one set of wells and a similar range of concentrations of reference compounds was added to a set of control wells. The cells were then incubated for 5 hours at 37° C. At the end of the incubation, cells were lysed by adding 100 microliters of detection mix containing luciferase substrate (AMP (22 ug/ml), ATP (1.1 mg/ml), dithiothreitol (3.85 mg/ml), HEPES (50 mM final concentration), EDTA (0.2 mg/ml), Triton N-101 (4 ul/ml), phenylacetic acid (45 ug/ml), oxalic acid (8.5 ug/ml), luciferin (28 ug/ml), pH 7.8). Plates were sealed and luminescence read within 30 minutes. The concentration of each of the compounds was plotted against luminescence counts per second (cps) and the resulting response curves subjected to non-linear regression using a four-parameter curve-fitting algorithm to calculate the $EC_{50}$ (the concentration of compound required to produce 50% of the maximal increase in luciferase activity) and the efficacy (the percent maximal activation compared to full induction by any of the well-known kappa opioid receptor agonists, such as asimadoline (EMD-61753: See Joshi et al., 2000, *J. Neurosci.* 20(15):5874-9), or U-69593: See Heidbreder et al., 1999, *Brain Res.* 616(1-2):335-8).

Table II shows the $EC_{50}$ values obtained from the cAMP inhibition assay with the exemplified compounds synthesized according to the present invention and tested on mouse kappa opioid receptor (mKOR) with confirmatory replication of results on the human kappa opioid receptor (hKOR) by the above-described methods.

Synthetic peptide amides of the invention were tested in a similar assay for potency on the human mu opioid receptor. Each of the compounds tested had an $EC_{50}$ for the human mu opioid receptor greater than or equal to 1 uM.

TABLE II

Kappa Opioid Agonist Activities

| COMPOUND # | mKOR | | hKOR | |
|---|---|---|---|---|
| | $EC_{50}$ (nM) | Efficacy(%) | $EC_{50}$ (nM) | Efficacy(%) |
| 1 | 0.403 | 98 | 0.49 | 102 |
| 2 | 0.08 | 97 | 0.13 | 99 |
| 3 | 9.05 | 88 | nd | nd |
| 4 | 50.56 | 87 | nd | nd |
| 5 | 3.01 | 96 | nd | nd |

TABLE II-continued

Kappa Opioid Agonist Activities

| COMPOUND | mKOR | | hKOR | |
|---|---|---|---|---|
| # | $EC_{50}$ (nM) | Efficacy(%) | $EC_{50}$ (nM) | Efficacy(%) |
| 6 | 0.041 | 100 | 0.17 | 107 |
| 7 | 0.028 | 102 | 0.14 | 104 |
| 8 | 0.197 | 102 | 0.16 | 93 |
| 9 | 0.088 | 92 | 0.39 | 134 |
| 10 | 0.085 | 99 | 0.12 | 92 |
| 11 | 0.08 | 100 | 0.12 | 90 |
| 12 | 0.092 | 100 | 0.30 | 99 |
| 13 | 0.115 | 96 | 0.24 | 96 |
| 14 | 0.022 | 96 | 0.21 | 105 |
| 15 | 1.966 | 93 | nd | nd |
| 16 | 0.030 | 99 | 0.12 | 90 |
| 17 | 0.056 | 99 | 0.12 | 90 |
| 18 | 0.049 | 99 | 0.14 | 99 |
| 19 | 0.035 | 101 | 0.21 | 93 |
| 20 | 0.193 | 92 | 0.15 | 97 |
| 21 | 0.078 | 97 | nd | nd |
| 22 | 0.081 | 97 | nd | nd |
| 23 | 0.045 | 95 | nd | nd |
| 24 | 0.033 | 96 | nd | nd |
| 25 | 0.1472 | 85 | 0.021 | 98 |
| 26 | 0.12 (avg.) | 78 | 0.0073 | 98 |
| 27 | 0.0005 | 85 | 0.0293 | 100 |
| 28 | 0.0471 | 89 | 0.0059 | 100 |
| 29 | 0.084 | 85 | 0.031 | 92 |
| 30 | 0.1931 | 86 | 0.0194 | 101 |
| 31 | 0.2456 | 82 | 0.0073 | 100 |
| 32 | 0.530 | 87 | 0.011 | 101 |
| 33 | 0.3476 | 92 | 0.012 | 94 |
| 34 | 0.1916 | 89 | 0.0306 | 103 |
| 35 | 0.4849 | 85 | 0.0667 | 95 |
| 36 | 0.6327 | 89 | 0.0034 | 99 |
| 37 | 0.072 | 87 | 0.0063 | 99 |
| 38 | 0.1894 | 87 | 0.0165 | 100 |
| 39 | 67.3 | 35 | nd | nd |
| 40 | 1.07 | 96 | 0.26 | 83 |
| 41 | 0.05 | 100 | 0.2 | 89 |
| 42 | 0.24 | 97 | 0.27 | 95 |
| 43 | 0.08 | 101 | 0.13 | 94 |
| 44 | 1.30 | 91 | 0.25 | 93 |
| 45 | 0.05 | 96 | 0.28 | 96 |
| 46 | 0.12 | 95 | nd | nd |
| 47 | 0.05 | 91 | nd | nd |
| 48 | 0.34 | 85 | nd | nd |
| 49 | 1.83 | 50 | nd | nd |
| 50 | 56.66 | 77 | nd | nd |
| 51 | 95.78 | 60 | nd | nd |
| 52 | 13.81 | 76 | nd | nd |
| 53 | 0.178 | 100 | 0.16 | 100 | nd—not determined

The synthetic peptide amide (53) was tested in a similar assay for potency on the human mu opioid receptor. The compound had an $EC_{50}$ for the human mu opioid receptor greater than or equal to 1 uM.

Example 46

Membrane Permeability of the Synthetic Peptide Amides

The Caco-2 cell line is a human colon adenocarcinoma cell line that differentiates in culture and is used to model the epithelial lining of the human small intestine. Compounds of the present invention can be tested in a membrane permeability assay using the TC7 subclone of Caco-2 in a standard assay (Cerep, Seattle, Wash.). Briefly, the apparent permeability coefficient ($P_{app}$) can be determined in the apical-to-basolateral (A-B) direction across cell monolayers cultured on 96-well polycarbonate membrane filters.

For instance the compounds of the invention can be tested at a concentration of, say, 10 uM at pH 6.5 in 1% DMSO, with the recipient side maintained at pH 7.4. The assay plate is incubated for 60 minutes at 37° C. with gentle shaking. Samples are taken at time zero from the donor side and at the end of the incubation period from both the donor and recipient sides. Samples are preferably analyzed by HPLC-MS/MS. The $P_{app}$ value (expressed as $10^{-6}$ cm/sec) is then calculated based on the appearance rate of compound in the recipient side. Reference compounds such as labetalol, propranolol, ranitidine, and vinblastine can be tested concurrently to ensure the validity of the assay.

Example 47

Inhibition of Cytochrome $P_{450}$ Oxidases

Inhibition of cytochrome $P_{450}$ oxidase isozymes CYP1A, CYP2C9, CYP2C19, CYP2D6 and CYP3A4 by synthetic peptide amide compound (17) of the invention was determined according to the following methods performed by Cerep (Seattle, Wash.):

In the cytochrome $P_{450}$ CYP1A assay, human liver microsomes (0.2 mg/ml protein) were incubated for 15 minutes at 37° C. with 10 uM test compound, 1 uM ethoxyresorufin, 1.3 mM NADP, 3.3 mM glucose-6-phosphate and 0.4 U/ml glucose-6-phosphate dehydrogenase. In the absence of test compound, the dextromethorphan added as substrate is oxidized to resorufin, and in the presence of an inhibitor of the CYP isozyme, the amount of resorufin produced is reduced. Furafylline was used as a reference inhibitor. The cytochrome $P_{450}$ CYP2C9 assay reaction mixture containing human liver microsomes (0.2 mg/ml protein) was incubated for 15 minutes at 37° C. with 10 uM test compound, 10 uM tolbutamide, 1.3 mM NADP, 3.3 mM glucose-6-phosphate and 0.4 U/ml glucose-6-phosphate dehydrogenase. In the absence of test compound, the tolbutamide is oxidized to 4-hydroxytolbutamide, and in the presence of an inhibitor of the CYP isozyme, the amount of 4-hydroxytolbutamide produced is reduced. Sulfaphenazole ($IC_{50}$: 0.35 uM) was the reference inhibitor. For the cytochrome $P_{450}$ CYP2C19 assay, human liver microsomes (0.2 mg/ml protein) were incubated for 15 minutes at 37° C. with 10 uM test compound, 10 uM omeprazole, 1.3 mM NADP, 3.3 mM glucose-6-phosphate and 0.4 U/ml glucose-6-phosphate dehydrogenase. In the absence of test compound, the omeprazole is oxidized to 5-hydroxy-omeprazole, and in the presence of an inhibitor of the CYP isozyme, the amount of 4-hydroxy-tolbutamide produced is reduced. Oxybutinin ($IC_{50}$: 7.1 uM) was the reference inhibitor.

The cytochrome $P_{450}$ CYP2D6 assay reaction containing human liver microsomes (0.2 mg/ml protein) was incubated for 15 minutes at 37° C. with 10 uM test compound, 5 uM dextromethorphan, 1.3 mM NADP, 3.3 mM glucose-6-phosphate and 0.4 U/ml glucose-6-phosphate dehydrogenase. In the absence of test compound, the dextromethorphan is oxidized, and in the presence of an inhibitor of the CYP isozyme, the amount of oxidation product is reduced. Quinidine ($IC_{50}$: 0.093 uM) was the reference inhibitor. Recombinant human cytochrome $P_{450}$ CYP3A4 (20 µmol/ml) was incubated for 20 minutes at 37° C. with 10 uM test compound, 5 uM midazolam, 1.3 mM NADP, 3.3 mM glucose-6-phosphate and 0.4 U/ml glucose-6-phosphate dehydrogenase. In the absence of test compound, the midazolam is oxidized, and in the presence of an inhibitor of the recombinant isozyme, the amount of oxidation product is reduced. The oxidation product is determined from the area under the curve after HPLC-MS/MS separation. Ketoconazole ($IC_{50}$: 0.55 uM) was the reference inhibitor. In each assay, the percent inhibition of the cytochrome $P_{450}$ CYP $P_{450}$ isozyme was determined as one hundred times the ratio of (1−the amount of product in the sample in the presence of the test compound) divided by the amount of product in the sample containing untreated isozyme. The results of duplicate assays (expressed as percent remaining CYP activity) are shown in Table III.

TABLE III

Percent Activity of Cytochrome $P_{450}$ CYP Isozymes

| Compound | (17) | |
|---|---|---|
| $P_{450}$ isozyme | Expt 1 | Expt 2 |
| CYP1A | 97.1 | 95.8 |
| CYP2C9 | 99.2 | 98.2 |
| CYP2C19 | 94.1 | 97.8 |
| CYP2D6 | 98.4 | 98.2 |
| CYP3A4 | 94.7 | 95.9 |

Example 48

Pharmacokinetcs in Cynomolgus Monkeys

A single bolus of the synthetic peptide amide compound was administered by intravenous injection to cynomolgus monkeys (n=4 males, body wt 3-5 kg, SNBL USA, Ltd, Everett, Wash.), and plasma samples taken at 5, 10, 15, 20, 30 60, 90 120, and 180 minutes post-injection. The "half life" was determined as the time required for the plasma concentration to fall by 50% after maximum concentration in the plasma was achieved. Cynomolgus monkeys were injected with a single intravenous dose of synthetic peptide amide compound (19) according to the protocol detailed in Example 19, and the half life of plasma concentration determined. Results are shown in Table V.

TABLE V

In vivo half life of synthetic peptide amide compound (19) *

| | Cynomolgus Monkeys |
|---|---|
| Administration Route | intravenous |
| Half Life (min) | 69 |

* Compound (19) is: D-Phe-D-Phe-D-Leu-D-Orn-[4-(N-methyl)amidino-homopiperazine amide] (SEQ ID NO: 1).

Example 49

Acetic Acid-Induced Writhing Assay in Mice

This test identifies compounds which exhibit analgesic activity against visceral pain or pain associated with activation of low pH-sensitive nociceptors [see Barber and Gottschlich (1986) Med. Res. Rev. 12: 525-562; Ramabadran and Bansinath (1986) Pharm. Res. 3: 263-270]. Intraperitoneal administration of dilute acetic acid solution causes a writhing behaviour in mice. A writhe is defined as a contraction of the abdominal muscles accompanied by an extension of the forelimbs and elongation of the body. The number of writhes observed in the presence and absence of test compounds is counted to determine the analgesic activity of the compounds.

Each day a writhing assay was performed, a vehicle control group of mice (n=6-8) that were treated identically to the test group (except that test compound was omitted from the injection dose) was always included and the average total number of writhes in this group used as the absolute reference point defining 0% decrease in pain perception for all other mice receiving a test compound on that day. Specifically, the total number of writhes of each mouse receiving the test compound was converted to % decrease in pain perception according to the following equation:

$$\% \text{ decrease in pain perception} = \frac{(W_v - W_c)}{W_v} \times 100$$

Where $W_v$ is the mean number of writhes in vehicle-treated group and $W_c$ is the number of writhes in compound-treated mouse. The data were analyzed using the 2-parameter Hill's equation (a.k.a. Emax model), where Emax is assumed to be 100% antinociperception (i.e., no writhes over the 15 min post-acetic acid administration)

Male ICR mice, 23-37 grams in weight, were weighed and placed in individual observation chamber (usually a 4000 ml glass beaker) with a fine layer of SANI-CHIPS rodent bedding at the bottom. To determine the activity and potency of test compounds, different doses of the compound solution or vehicle were injected subcutaneously in the back of the neck 15 or 180 minutes prior to administration of acetic acid solution. After administration of the compound or vehicle control, mice were returned to their individual observation chambers awaiting the intraperitoneal administration of acetic acid solution. Fifteen minutes or three hours later, according to the interval time defined in each experiment between compound delivery and acetic acid injection, a dose corresponding to 10 ml/kg of a 0.6% (v/v) acetic acid solution was then injected into the right lower quadrant of the abdomen. Immediately after the injection, the mouse was returned to its observation chamber and the recording of the number of writhes begun immediately. The number of writhes was counted over a 15-min period starting from the time of acetic acid injection, the data being collected over three separate 5 minute time periods (0-5 min, 5-10 min, and 10-15 min).

The data were reported as $ED_{50}$, and Hill coefficient. The $ED_{50}$ is expressed either as mean±standard error of the mean (sem) ($ED_{50}$+/−sem) or as geometric mean with 95% confidence interval (95% CI) using t-score. The Hill coefficient is expressed as arithmetic mean±sem calculated from the values obtained from the animals. Results are shown in FIG. 10.

Example 50

Inhibition of Locomotion in Mice to Measure Sedation by Compounds after Subcutaneous Injection Compounds which exhibit sedative activity inhibit the spontaneous locomotion of mice in a test chamber. To determine the potential sedative effect of test compounds, the extent of locomotion after the administration of the test compound or vehicle control can be determined and compared with a specialized apparatus designed for this purpose (Opto-Varimex Activity Meter). At the start of each experiment, each mouse was weighed and examined to determine good health. To determine the activity and potency of compounds, different doses of the compound solution or vehicle were injected subcutaneously 15 or 180 minutes prior to initiation of data collection. The subcutaneous injection was performed in the back of the neck of the mouse, pinched in a "tent" to allow proper access for the syringe needle. After injection, each animal was placed individually in Plexiglas boxes (43 cm×43 cm) inside the Opto-Varimex Activity Meter apparatus. Before the animal was placed in the apparatus, a thin layer of SANI-CHIPS rodent bedding was placed on the bottom of the Plexiglas box to provide a comfortable environment. Each Opto-Varimex Activity Meter apparatus was then turned on and data acquisition begun by the ATM3 Auto-Track System. The data were processed and results expressed in the same way as described for the writhing assay data above.

Example 51

Analgesic Effect Vs. Sedative Effect of Synthetic Peptide Amide (17): D-Phe-D-Phe-D-Leu-D-Orn-[4-(4,5-dihydro-1H-imidazol-2-yl)homopiperazine amide] (SEQ ID NO: 1)

Inhibition of acetic acid-induced writhing is an indication of an analgesic effect (also called an antinociceptive effect). Similarly, a reduction in locomotion can be used as a measure of a general sedative effect. The $ED_{50}$ determined in the acetic acid-induced writhing assay in IRC mice was 74 ug/kg [with a 95% confidence interval of 49-99 ug/kg] when synthetic peptide amide (17) was delivered subcutaneously. The $ED_{50}$ value determined in the inhibition of locomotion assay was 3172 ug/kg [with a 95% confidence interval of 1810-4534 ug/kg] for the same synthetic peptide amide delivered subcutaneously. See FIG. 10. The therapeutic ratio of the analgesic effect over the sedative effect is the fold higher $ED_{50}$ required to achieve a sedative effect as compared to the $ED_{50}$ required to achieve an analgesic effect. Thus, compound (17) exhibits a (3172/74) fold ratio, i.e. 42.86 fold. Thus, the therapeutic ratio for compound (17) is approximately 43 fold.

Example 52

Synthetic Peptide Amide Compound Pharmacokinetcs in Monkeys

Samples were administered to male monkeys, *Macaca fascicularis* (SNBL USA, Ltd., Everett, Wash., purpose-bred cynomolgus monkeys. Closely related to humans, both phylogenetically and physiologically) aged 3-7 years and weighing 3-5 kilograms. Samples were administered in a superficial vein of the arm or leg (e.g. brachial, or saphenous) in 0.9% saline for injection, USP (Baxter Healthcare, Deerfield, Ill.) as follows: A cassette sample containing 0.4 mg of compound (19) of the present invention and 0.4 mg of each of nine other compounds (for a total dose of 4 mg) was prepared in 2 ml 0.9% saline for injection, providing a concentration of 0.2 mg/ml of each of the ten compounds. Exactly 2 ml was administered as an intravenous bolus to the test animal, resulting in a total dose level of 0.8 to 1.3 mg/kg depending on the body weight of the individual animal. The intravenous injection was followed by a 1 ml flush with 0.9% saline for injection. Blood samples of 0.6 ml were collected by venipuncture from a peripheral vein at 2, 5, 10, 15 and 30 minutes post dose injection, and then at 1, 2 and 4 hours. Each sample was placed in a pre-chilled glass test tube containing lithium heparin and immediately chilled on ice. Plasma was collected after centrifugation at 2,000 g for fifteen minutes at 2-8° C. The plasma layers of each sample were transferred to polypropylene tubes and stored frozen at −60° C. or lower until assayed. One hundred microliter aliquots of thawed plasma were spiked with 5 microliters of a 400 ng/ml solution of an appropriate internal standard (in this case a known synthetic peptide amide compound) in 0.1% TFA, and the proteins were precipitated with 100 microliters of 0.1% TFA in acetonitrile. The samples were centrifuged at 1000×g for 5 minutes and the supernatants analyzed by LC-MS. LC-MS analysis was performed on a Finnigan LCQ Deca mass spectrometer interfaced to a Surveyor HPLC system (Thermo Electron Corporation, Waltham, Mass., USA). HPLC analysis was performed on 2.1×150 mm C18 reversed phase columns with a gradient of 0.01% TFA in acetonitrile in 0.01% TFA in water. Mass detection was performed in the selected reaction monitoring mode (SRM). Quantitation was performed against a calibration curve of the analyte in blank cynomolgus monkey plasma using the same internal standard. Data analysis and the extraction of pharmacokinetic parameters were performed with the program PK Solutions 2.0 (Summit Research Services, Ashland, Ohio, USA). Results for compound (19): D-Phe-D-Phe-D-Leu-D-Orn-[4-(N-methyl)amidino-homopiperazine amide] (SEQ ID NO: 1) are shown in FIG. 11.

Example 53

Ocular Analgesia Induced by Synthetic Peptide Amides of the Invention

Ocular analgesia induced by the synthetic peptide amides of the invention can be evaluated by in vivo testing in rabbits as follows: Five volumes of the test compound, 50 microliters each in physiological saline, at the concentration to be tested are instilled into the right eye of naïve albino New Zealand strain rabbits within a period of twenty minutes. Fifteen minutes after the last instillation of the test compound, each animal is administered a single instillation of 30 microliters of 10 mg/ml capsaicin (33 mM) in the treated eye. Capsaicin is known to induce corneal pain. Corneal pain is evaluated by measurement of the palpebral opening measured in millimeters using a transparent ruler in the treated and untreated eyes. In this animal model, the reduction in size of the palpebral opening after instillation of capsaicin is an indication of the degree of induced pain. Thus, any observed restoration in size of the palpebral opening after treatment with test compound is taken as a measure of relief from capsaicin-induced ocular pain.

These evaluations are performed before treatment with the test compound (pre-test), immediately prior to the instillation of capsaicin, and then 1, 5, 10, 15, 20, 25, 30, 40, 50 and 60 minutes following the instillation of capsaicin. The mean of palpebral opening measurements can be expressed as percent of control over the period from 10-30 minutes after capsaicin instillation in rabbits pre-instilled with a kappa opioid agonist of the invention and after preinstillation with a standard concentration of a control compound such as Diltiazem, a benzothiazepine calcium channel blocker. See Gonzalez et al., (1993) *Invest. Ophthalmol. Vis. Sci.* 34: 3329-3335.

Example 54

Dose Response of Synthetic Peptide Amides of the Invention in Capsaicin-Induced Ocular Pain Ocular analgesia induced by the synthetic peptide amide to be tested is instilled at several concentrations into the right eye of naïve albino New Zealand strain rabbits and evaluated as described in Example 31, above. Results are compared with analgesia induced by 10 mg/ml morphine (a non-selective opioid agonist), and with 10 mM Diltiazem as control in the same experiment and under the same conditions.

The specifications of each of the U.S. patents and published patent applications, and the texts of the literature references cited in this specification are herein incorporated by reference in their entireties. In the event that any definition or description found in one or more of these references is in conflict with the corresponding definition or description herein, then the definition or description disclosed herein is intended.

The examples provided herein are for illustration purposes only and are not to be interpreted as limiting the scope of the invention, the full scope of which will be immediately recognized by those of skill in the art.

What is claimed is:

1. A method of treating, inhibiting or preventing kappa opioid receptor associated pain, or of inhibiting or treating kappa opioid receptor associated pancreatitis or pruritis in a mammal, the method comprising administering to the mammal a composition comprising an effective amount of a synthetic peptide amide having the formula:

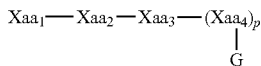

or a stereoisomer, mixture of stereoisomers, pharmaceutically acceptable salt, hydrate, acid salt hydrate, or N-oxide thereof, wherein each $Xaa_1$ is independently selected from the group consisting of (A)(A')D-Phe, (A)(A')(α-Me)D-Phe, D-Tyr, D-Tic, D-tert-leucine, D-neopentylglycine, D-phenylglycine, D-homophenylalanine, and β-(E)D-Ala, wherein each (A) and each (A') are phenyl ring substituents independently selected from the group consisting of —H, —F, —Cl, —NO$_2$, —CH$_3$, —CF$_3$, —CN and —CONH$_2$, and wherein each (E) is independently selected from the group consisting of cyclobutyl, cyclopentyl, cyclohexyl, pyridyl, thienyl and thiazolyl;

each $Xaa_2$ is independently selected from the group consisting of (A)(A')D-Phe, (A)(A')(α-Me)D-Phe, D-1Nal, D-2Nal, D-Tyr, (E)D-Ala, and D-Trp;

each $Xaa_3$ is independently selected from the group consisting of D-Nle, D-Phe, (E)D-Ala, D-Leu, (α-Me)D-Leu, D-Hle, D-Val, and D-Met;

each $Xaa_4$ is independently selected from the group consisting of (B)$_2$D-Arg, (B)$_2$D-Nar, (B)$_2$D-Har, ξ-(B)D-Hlys, D-Dap, ε-(B)D-Lys, ε-(B)$_2$-D-Lys, D-Amf, amidino-D-Amf, γ-(B)$_2$D-Dbu, δ-(B)$_2$α-(B')D-Orn, D-2-amino-3(4-piperidyl)propionic acid, D-2-amino-3(2-aminopyrrolidyl)propionic acid, D-α-amino-β-amidino-propionic acid, α-amino-4-piperidineacetic acid, cis-α,4-diaminocyclohexane acetic acid, trans-α,4-diaminocyclohexaneacetic acid, cis-α-amino-4-methyl-aminocyclo-hexane acetic acid, trans-α-amino-4-methylaminocyclohexane acetic acid, α-amino-1-amidino-4-piperidineacetic acid, cis-α-amino-4-guanidino-cyclohexane acetic acid, and trans-α-amino-4-guanidinocyclohexane acetic acid, wherein each (B) is independently selected from the group consisting of —H and C$_1$-C$_4$ alkyl, and (B') is —H or (α-Me), and p is zero or 1;

G is selected from one of the following moieties:

(i) G is

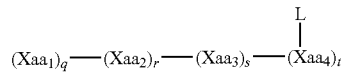

wherein
q is zero or 1;
r is zero or 1;
s is zero or 1;
p and t are each independently zero or 1, provided that at least one of q, r, s and t is 1;

and wherein either

A. (i) L is a linker selected from the group consisting of ε-D-Lys, ε-Lys, δ-D-Orn, ε-Orn, γ-aminobutyric acid, 8-aminooctanoic acid, 11-amino-undecanoic acid, 8-amino-3,6-dioxaoctanoic acid, 4-amino-4-carboxylic piperidine and (D-Lys-GlyLactam)$_2$, and (ii) the moieties $Xaa_1$-$Xaa_2$-$Xaa_3$-$(Xaa_4)_p$ and $(Xaa_1)_q$-$(Xaa_2)_r$-$(Xaa_3)_s$-$(Xaa_4)_t$ are different from one another, or B. L is a linker selected from the group consisting of γ-aminobutyric acid, 8-aminooctanoic acid, 11-aminoundecanoic acid, 8-amino-3,6-dioxaoctanoic acid, 4-amino-4-carboxylic piperidine and (D-Lys-Gly Lactam)$_2$, and (ii) G is

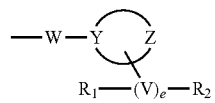

wherein p is 1;
and
the moiety

is an optionally substituted 6 or 7-membered heterocyclic ring moiety wherein Y is C or N and Z is C, N, O, S, SO, or SO$_2$; provided that Y and Z are separated by at least two ring atoms; and provided further that when such ring moiety is aromatic, then Y is C;

wherein W is selected from the group consisting of:
null, provided that when W is null, Y is N;
—NH—(CH$_2$)$_b$— with b equal to zero, 1, 2, 3, 4, 5, or 6; and
—NH—(CH$_2$)$_c$—O— with c equal to 2, or 3;

wherein V is C$_1$-C$_6$ alkyl, and e is zero or 1, wherein when e is zero, then V is null and, R$_1$ and R$_2$ are directly bonded to the same or different ring atoms;

wherein (a) R$_1$ is —H, —OH, halo, CF$_3$, —NH$_2$, —COOH, C$_1$-C$_6$ alkyl, amidino, C$_1$-C$_6$ alkyl-substituted amidino, aryl, optionally substituted heterocyclyl, Proamide, Pro, Gly, Ala, Val, Leu, Ile, Lys, Arg, Orn, Ser, Thr, CN, CONH$_2$, COR', SO$_2$R', CONR'R'', NHCOR', OR', or SO$_2$NR'R''; wherein said optionally substituted heterocyclyl is optionally singly or doubly substituted with substituents independently selected from the group consisting of $C_1$-$C_6$ alkyl, —$C_1$-$C_6$ alkoxy, oxo, —OH, —Cl, —F, —$NH_2$, —$NO_2$, —CN, —COOH, and amidino; wherein R' and R" are each independently —H, $C_1$-$C_8$ alkyl, aryl, heterocyclyl or R' and R" are combined to form a 4- to 8-membered ring, which ring is optionally substituted singly or doubly with substituents independently selected from the group consisting of $C_1$-$C_6$ alkyl, —$C_1$-$C_6$ alkoxy, —OH, —Cl, —F, —$NH_2$, —$NO_2$, —CN, —COOH and amidino; and $R_2$ is H, amidino, singly or doubly $C_1$-$C_6$ alkyl-substituted amidino, —CN, —$CONH_2$, —CONR'R", —NHCOR', —$SO_2$NR'R", or —COOH; or (b) $R_1$ and $R_2$ taken together can form an optionally substituted 4- to 9-membered heterocyclic monocyclic or bicyclic ring moiety which is bonded to a single ring atom of the Y and Z-containing ring moiety; or (c) $R_1$ and $R_2$ taken together with a single ring atom of the Y and Z-containing ring moiety can form an optionally substituted 4- to 8-membered heterocyclic ring moiety to form a spiro structure; or (d) $R_1$ and $R_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety;

wherein each of said optionally substituted 4- to 9-membered heterocyclic ring moieties comprising $R_1$ and $R_2$ is optionally singly or doubly substituted with substituents independently selected from the group consisting of $C_1$-$C_6$ alkyl, —$C_1$-$C_6$ alkoxy, optionally substituted phenyl, oxo, —OH, —Cl, —F, —$NH_2$, —$NO_2$, —CN, —COOH, and amidino;

provided that when the Y and Z-containing ring moiety is a six or seven membered ring comprising a single ring heteroatom and when one of Y and Z is C and the other of Y and Z is N, and e is zero, then $R_1$ is not —OH, and $R_1$ and $R_2$ are not both —H;

provided further that when the Y and Z-containing ring moiety is a six membered ring comprising two ring heteroatoms, both Y and Z are N, W is null, and —$V_e$($R_1$)($R_2$) is attached to Z, then —$V_e$($R_1$)($R_2$) is selected from the group consisting of amidino, $C_1$-$C_6$ alkyl-substituted amidino, dihydroimidazole, —$CH_2$COOH, and —$CH_2$C(O)$NH_2$; and lastly, provided that if the Y and Z-containing ring moiety is a six membered ring comprising an S or O ring heteroatom, or if the Y and Z-containing ring moiety is a six membered ring comprising two ring heteroatoms, wherein both Y and Z are N and W is null, or if the Y and Z-containing ring moiety is a six membered aromatic ring comprising a single ring heteroatom, which heteroatom is N, then, when e is zero, $R_1$ and $R_2$ are not both —H.

2. The method according to claim 1, wherein G is

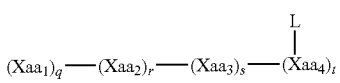

wherein p, q, r, s and t are each 1.

3. The method according to claim 1, wherein G is

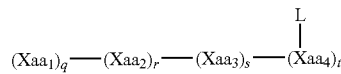

and L is a linker selected from the group consisting of ε-D-Lys, ε-Lys, δ-D-Orn, δ-Orn, 4-amino-4-carboxylic piperidine and (D-Lys-Gly lactam)$_2$.

4. The method according to claim 1, wherein W is null, Y is N and Z is C.

5. The method according to claim 1, wherein the Y and Z-containing ring moiety is a six-membered saturated ring comprising a single ring heteroatom.

6. The method according to claim 1, wherein Y and Z are both N and are the only ring heteroatoms in the Y and Z-containing ring moiety.

7. The method according to claim 1, wherein e is zero.

8. The method according to claim 1, wherein $R_1$ and $R_2$ taken together with one ring atom of the Y and Z-containing ring moiety comprise a 4- to 8-membered heterocyclic ring moiety which with the Y and Z-containing ring moiety forms a spiro structure and W is null.

9. The method according to claim 1, wherein e is zero and $R_1$ and $R_2$ are bonded directly to the same ring atom.

10. The method according to claim 1, wherein $R_1$ is H, OH, —$NH_2$, —COOH, $C_1$-$C_3$ alkyl, amidino, $C_1$-$C_3$ alkyl-substituted amidino, dihydroimidazole, Pro, Pro amide, or $CONH_2$ and wherein $R_2$ is H, or —COOH.

11. The method according to claim 1, wherein the moiety:

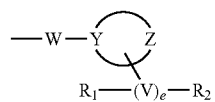

is selected from the group consisting of:

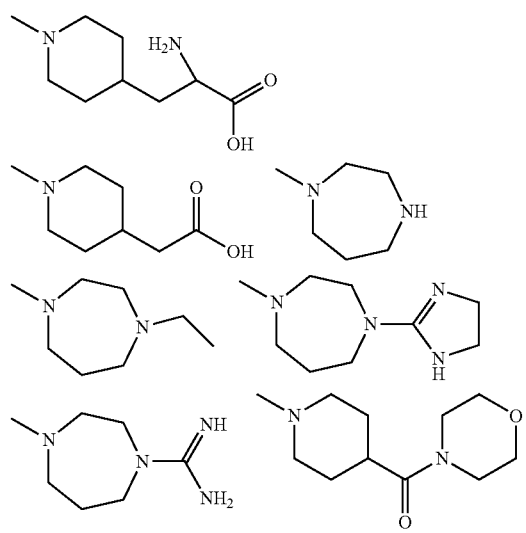

-continued
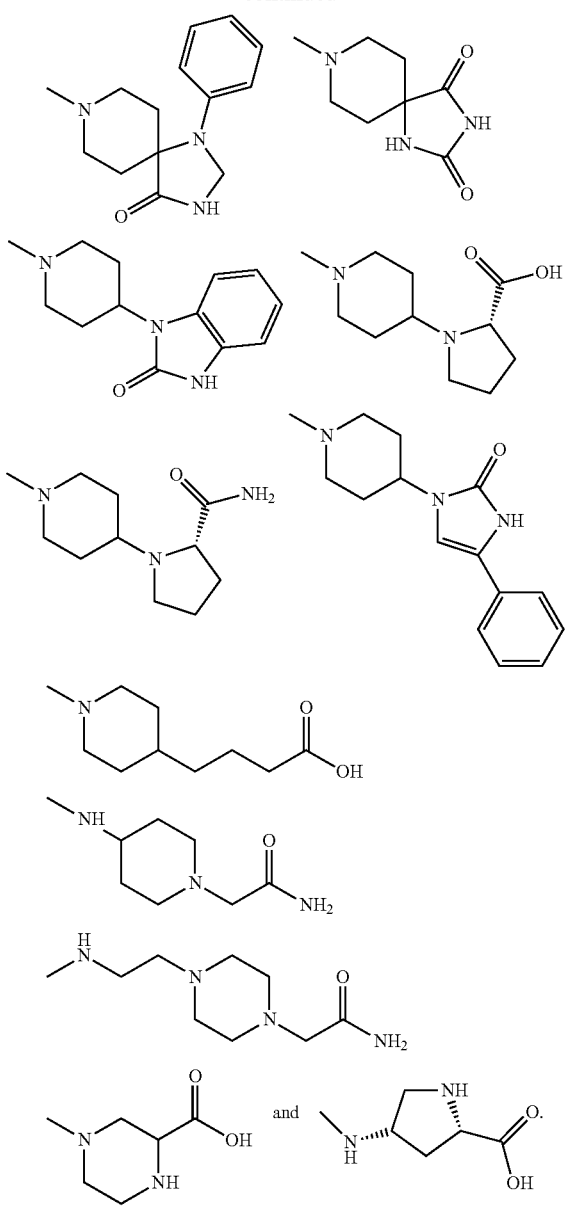
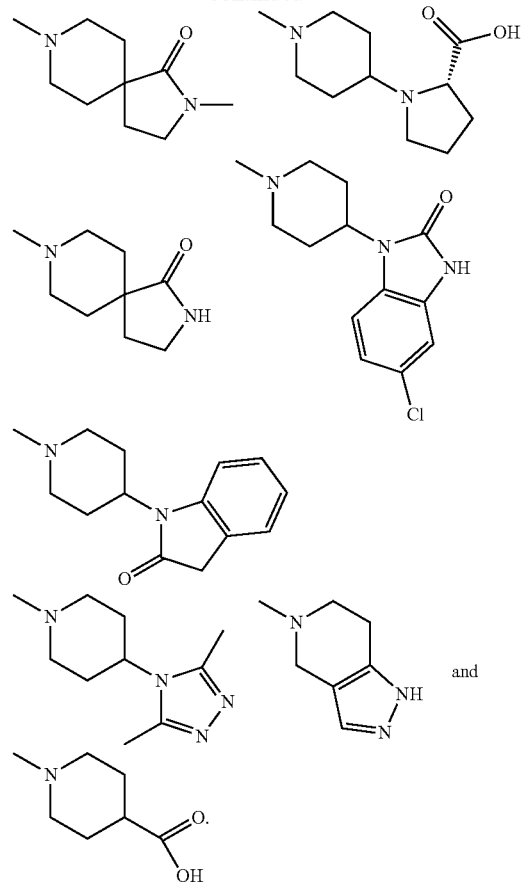
12. The method according to claim 1, wherein the moiety:
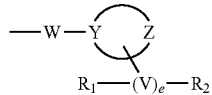
is selected from the group consisting of:
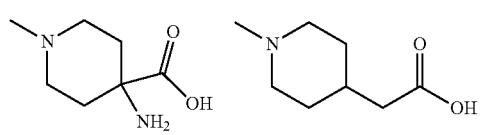
13. The method according to claim 1, wherein the synthetic peptide amide has a structure selected from the group consisting of:
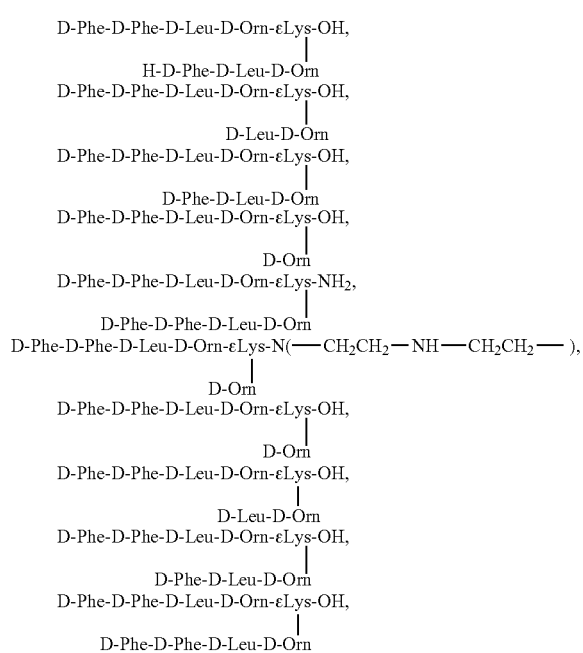

1N,4N-bis-[D-Phe-D-Phe-D-Leu-(iPr)D-Orn]-4-amino-4-carboxylic piperidine,
1N,4N-bis-[D-Phe-D-Phe-D-Leu-D-Dap(Amidino)]-4-amino-4-carboxylic piperidine,
1N,4N-bis-(D-Phe-D-Phe-D-Leu-D-Nar)-4-amino-4-carboxylic piperidine,
and

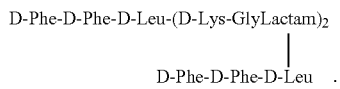

14. The method according to claim 1, wherein the moiety

is an optionally substituted 6- or 7-membered heterocyclic ring moiety wherein Y is nitrogen and Z is carbon, nitrogen, oxygen, sulfur, sulfoxide, or sulfonyl.

15. The method according to claim 1, wherein the synthetic peptide amide is administered to the mammal in a pharmaceutically acceptable excipient or carrier.

16. The method according to claim 1, comprising administering to the mammal a composition comprising an effective amount of the synthetic peptide amide by injection, infusion or by a pump.

17. The method according to claim 16, wherein the administration is intravenous, subcutaneous, intramuscular, intraperitoneal, intra-articular or intraocular.

18. The method according to claim 1, wherein the administration to the mammal is topical or local.

19. The method according to claim 18, wherein the composition is administered intranasally, transdermally, intravaginally, intrarectally or by an intrapulmonary route.

20. The method according to claim 18, wherein the composition is administered iontophoretically, or by a patch coated, diffused or impregnated with the synthetic peptide amide.

21. The method according to claim 18, wherein the composition is administered locally in an implant.

22. The method according to claim 18, wherein the composition is administered topically to a mucosal surface selected from the group consisting of a mouth, a esophagus, a larynx, a bronchus and a nasal passage.

23. The method according to claim 18, wherein the composition is administered topically to a vagina, a rectum or an anus.

24. The method according to claim 18, wherein the composition is administered in a sustained-release formulation.

25. The method according to claim 18, wherein the composition is administered in a tablet, a capsule, an ointment, a liquid, a powder or a gum.

26. The method according to claim 1, comprising administering the composition orally to the mammal.

27. The method according to claim 1, wherein the mammal is a human.

28. The method according to claim 1, wherein the disease or condition is pain.

29. A method of treating, inhibiting or preventing kappa opioid receptor associated pain, or of inhibiting or treating kappa opioid receptor associated pancreatitis or pruritis in a mammal, the method comprising administering to the mammal a composition comprising an effective amount of a synthetic peptide amide having the formula:

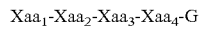

or a stereoisomer, mixture of stereoisomers, pharmaceutically acceptable salt, hydrate, acid salt hydrate, or N-oxide thereof, wherein:

$Xaa_1$ is independently selected from the group consisting of (A)(A')D-Phe, (A)(A')($\alpha$-Me)D-Phe, D-Tyr, D-Tic, D-tert-leucine, D-neopentylglycine, D-phenylglycine, D-homophenylalanine, and $\beta$-(E)D-Ala, $Xaa_2$ is independently selected from the group consisting of (A)(A')D-Phe, (A)(A')($\alpha$-Me)D-Phe, D-1Nal, D-2Nal, D-Tyr, (E)D-Ala, and D-Trp;

$Xaa_3$-$Xaa_4$- is selected from the group consisting of D-Nle-(B)$_2$D-Arg-, D-Leu-$\delta$-(B)$_2$$\alpha$-(B')D-Orn-, and ($\alpha$-Me)D-Leu-$\delta$(B)$_2$-$\alpha$(B')D-Orn-;

wherein each (A) and each (A') are phenyl ring substituents independently selected from the group consisting of —H, —F, —Cl, —NO$_2$, —CH$_3$, —CF$_3$, —CN, —CONH$_2$, and each (B) is independently selected from the group consisting of —H and C$_1$-C$_4$ alkyl, and (B') is —H or ($\alpha$-Me); and wherein each (E) is independently selected from the group consisting of cyclobutyl, cyclopentyl, cyclohexyl, pyridyl, thienyl and thiazolyl;

G is

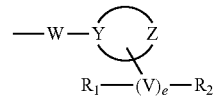

and the moiety

is an optionally substituted 4 to 8-membered heterocyclic ring moiety wherein all ring heteroatoms in said ring moiety are N; wherein Y and Z are each independently C or N; provided that when such ring moiety is a six, seven or eight-membered ring, Y and Z are separated by at least two ring atoms; and provided that when such ring moiety has a single heteroatom which is N, then such ring moiety is non-aromatic;

wherein W is selected from the group consisting of:
null, provided that when W is null, Y is N;
—NH—(CH$_2$)$_b$— with b equal to zero, 1, 2, 3, 4, 5, or 6; and
—NH—(CH$_2$)$_c$—O— with c equal to 2, or 3;

wherein V is C$_1$-C$_6$ alkyl, and e is zero or 1, wherein when e is zero, then V is null and, R$_1$ and R$_2$ are directly bonded to the same or different ring atoms;

wherein
(a) R$_1$ is —H, —OH, halo, CF$_3$, —NH$_2$, —COOH, C$_1$-C$_6$ alkyl, amidino, C$_1$-C$_6$ alkyl-substituted amidino, aryl, optionally substituted heterocyclyl, Pro-amide, Pro, Gly, Ala, Val, Leu, Ile, Lys, Arg, Orn, Ser, Thr, CN, CONH$_2$, COR', SO$_2$R', CONR'R", NHCOR', OR', or SO$_2$NR'R"; wherein said optionally substituted heterocyclyl is optionally singly or doubly substituted with substituents independently selected from the group consisting of C$_1$-C$_6$ alkyl, —C$_1$-C$_6$ alkoxy, oxo, —OH, —Cl, —F, —NH$_2$, —NO$_2$, —CN, —COOH, and amidino; wherein R' and R" are each independently —H, C$_1$-C$_8$ alkyl, aryl, heterocyclyl or R' and R" are combined to form a 4- to 8-membered ring, which ring is optionally substituted singly or doubly with substituents independently selected from the group consisting of C$_1$-C$_6$ alkyl, —C$_1$-C$_6$ alkoxy, —OH, —Cl, —F, —NH$_2$, —NO$_2$, —CN, —COOH and amidino; and R$_2$ is H, amidino, singly or doubly C$_1$-C$_6$ alkyl-substituted amidino, —CN, —CONH$_2$, —CONR'R", —NHCOR', —SO$_2$NR'R", or —COOH; or (b) R$_1$ and R$_2$ taken together can form an optionally substituted 4- to 9-membered heterocyclic monocyclic or bicyclic ring moiety which is bonded to a single ring atom of the Y and Z-containing ring moiety; or (c) R$_1$ and R$_2$ taken together with a single ring atom of the Y and Z-containing ring moiety can form an optionally substituted 4- to 8-membered heterocyclic ring moiety to form a spiro structure; or (d) R$_1$ and R$_2$ taken together with two or more adjacent ring atoms of the Y and Z-containing ring moiety can form an optionally substituted 4- to 9-membered heterocyclic monocyclic or bicyclic ring moiety fused to the Y and Z-containing ring moiety;

wherein each of said optionally substituted 4- to 9-membered heterocyclic ring moieties comprising R$_1$ and R$_2$ is optionally singly or doubly substituted with substituents independently selected from the group consisting of C$_1$-C$_6$ alkyl, —C$_1$-C$_6$ alkoxy, optionally substituted phenyl, oxo, —OH, —F, —NH$_2$, —NO$_2$, —CN, —COOH, and amidino;

provided that when the Y and Z-containing ring moiety is a six or seven membered ring comprising a single ring heteroatom and when one of Y and Z is C and the other of Y and Z is N, and e is zero, then R$_1$ is not —OH, and R$_1$ and R$_2$ are not both —H;

provided further that when the Y and Z-containing ring moiety is a six membered ring comprising two ring heteroatoms, both Y and Z are N, W is null, and —V$_e$(R$_1$)(R$_2$) is attached to Z, then —V$_e$(R$_1$)(R$_2$) is selected from the group consisting of amidino, C$_1$-C$_6$ alkyl-substituted amidino, dihydroimidazole, —CH$_2$COOH, and —CH$_2$C(O)NH$_2$; and and lastly, provided that if the Y and Z-containing ring moiety is a six membered ring comprising two ring heteroatoms, wherein both Y and Z are N and W is null, or if the Y and Z-containing ring moiety is a six membered aromatic ring comprising a single ring heteroatom, which heteroatom is N, then, when e is zero, R$_1$ and R$_7$ are not both —H.

30. The method according to claim 29, wherein W is null, Y is N and Z is C.

31. The method according to claim 29, wherein the Y and Z-containing ring moiety is a six-membered saturated ring comprising a single ring heteroatom.

32. The method according to claim 29, wherein Y and Z are both N and are the only ring heteroatoms in the Y and Z-containing ring moiety.

33. The method according to claim 29, wherein e is zero.

34. The method according to claim 29, wherein R$_1$ and R$_2$ taken together with one ring atom of the Y and Z-containing ring moiety comprise a 4- to 8-membered heterocyclic ring moiety which with the Y and Z-containing ring moiety forms a spiro structure and W is null.

35. The method according to claim 29, wherein e is zero and R$_1$ and R$_2$ are bonded directly to the same ring atom.

36. The method according to claim 29, wherein R$_1$ is H, OH, —NH$_2$, —COOH, C$_1$-C$_3$ alkyl, amidino, C$_1$-C$_3$ alkyl-substituted amidino, dihydroimidazole, Pro, Pro amide, or CONH$_2$ and wherein R$_2$ is H, or —COOH.

37. The method according to claim 29, wherein the moiety:

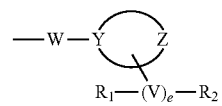

is selected from the group consisting of:

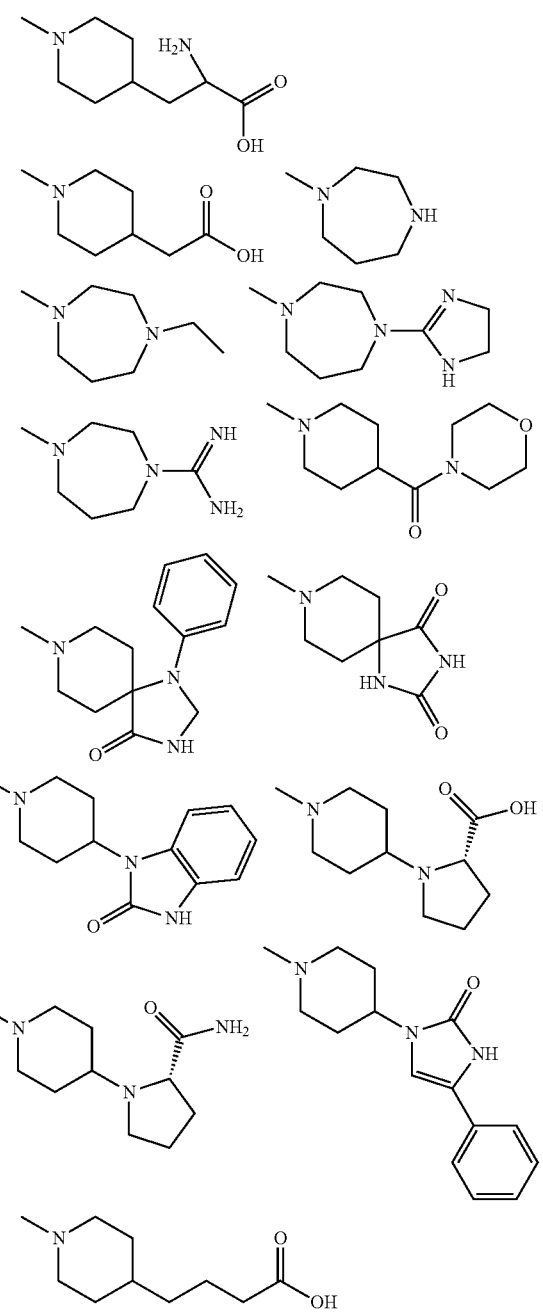

-continued
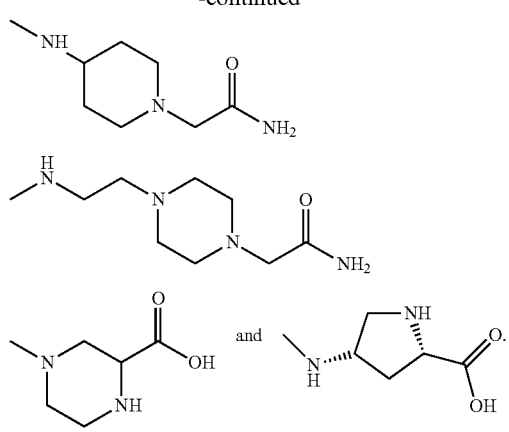
38. The method according to claim 29, wherein the moiety:
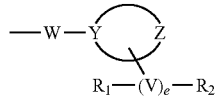
is selected from the group consisting of:
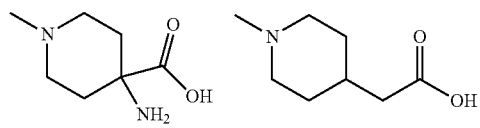
-continued
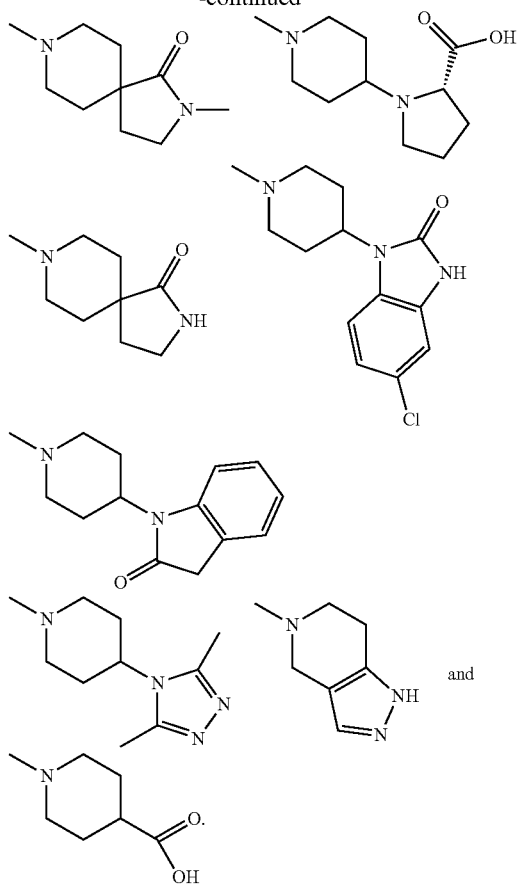
* * * * *